US010752699B2

(12) United States Patent
Harris et al.

(10) Patent No.: US 10,752,699 B2
(45) Date of Patent: Aug. 25, 2020

(54) ANTI-APOBEC3 ANTIBODIES AND METHODS OF MAKING AND USING

(71) Applicant: Regents of the University of Minnesota, Minneapolis, MN (US)

(72) Inventors: Reuben S. Harris, St. Paul, MN (US); William Brown, Shoreview, MN (US); Michael Carpenter, Minneapolis, MN (US); Emily Law, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/738,664

(22) PCT Filed: Jun. 29, 2016

(86) PCT No.: PCT/US2016/040011
§ 371 (c)(1),
(2) Date: Dec. 21, 2017

(87) PCT Pub. No.: WO2017/004151
PCT Pub. Date: Jan. 5, 2017

(65) Prior Publication Data
US 2018/0171029 A1   Jun. 21, 2018

Related U.S. Application Data

(60) Provisional application No. 62/186,109, filed on Jun. 29, 2015.

(51) Int. Cl.
*C07K 16/40* (2006.01)
*G01N 33/574* (2006.01)
*C07K 16/18* (2006.01)
*A61P 37/06* (2006.01)

(52) U.S. Cl.
CPC .............. *C07K 16/40* (2013.01); *A61P 37/06* (2018.01); *C07K 16/18* (2013.01); *G01N 33/574* (2013.01); *C07K 2317/14* (2013.01); *C07K 2317/56* (2013.01); *C07K 2317/565* (2013.01); *G01N 2333/978* (2013.01)

(58) Field of Classification Search
None
See application file for complete search history.

(56) References Cited

U.S. PATENT DOCUMENTS

| 6,444,638 | B2 | 9/2002 | Schwartz et al. |
| 7,429,487 | B2 | 9/2008 | Pytela et al. |
| 2005/0250719 | A1 | 11/2005 | Menne et al. |
| 2007/0293525 | A1 | 12/2007 | Djung et al. |
| 2009/0105187 | A1 | 4/2009 | Grant et al. |
| 2009/0191194 | A1 | 7/2009 | Menne et al. |
| 2010/0197768 | A1 | 8/2010 | Smith et al. |
| 2011/0143946 | A1 | 6/2011 | Gehrmann et al. |
| 2012/0252026 | A1 | 10/2012 | Harris et al. |
| 2015/0023955 | A1 | 1/2015 | Tavazoie et al. |
| 2015/0111836 | A1 | 4/2015 | Kottler et al. |
| 2018/0171029 | A1 | 6/2018 | Harris et al. |
| 2018/0185302 | A1 | 7/2018 | Harris et al. |
| 2019/0085405 | A1 | 3/2019 | Harris |

FOREIGN PATENT DOCUMENTS

| DE | 10244453 A1 | 4/2004 |
| EP | 1 639 141 B1 | 3/2006 |
| EP | 2338498 A1 | 6/2011 |
| WO | WO 2004/028516 A2 | 4/2004 |
| WO | WO 2008/144753 A2 | 11/2008 |
| WO | WO 2010/006214 A1 | 1/2010 |
| WO | WO 2013/112601 A1 | 8/2013 |
| WO | WO 2014/060785 A2 | 4/2014 |
| WO | WO 2015/032800 A2 | 3/2015 |
| WO | WO 2016/008976 A1 | 1/2016 |
| WO | WO 2016/009017 A1 | 1/2016 |
| WO | WO 2016/083791 A1 | 6/2016 |
| WO | WO 2017/004151 A1 | 1/2017 |
| WO | WO 2017/004165 A1 | 1/2017 |
| WO | WO 2017/004181 A1 | 1/2017 |
| WO | WO 2017/165629 A1 | 9/2017 |

OTHER PUBLICATIONS

Abnova, 2014, APOBEC3B mouse monoclonal antibody (hybridoma).*
Han et al (2008, PLoS Pathogens, 4(7):e1000095).*
Abnova, 2014, APOBEC3B mouse monoclonal antibody (hybridoma)[online].*
Jin et al (Oncology Reports, 2014, 32:1867-1872).*
Leenaars et al (ILAR Journal, 2005, 46:269-279).*
Lipman et al (ILAR Journal, 2005, 46:258-268).*
Wissing et al (J Biological Chemistry, 2011, 286:36427-36437).*
Emens, "The interplay of immunotherapy and chemotherapy: harnessing potential synergies" 2015 *Cancer Immunol Res.*, 3(5):436-43.
Ming, "First-In-Class Small Molecule Inhibitors of the Single-Strand DNA Cytosine Deaminase APOBEC3G" 2012 ACS Chemical Biology, 7(3):506-517.
Nan, "TPCA-1 Is a Direct Dual Inhibitor of STAT3 and NF-Band Regresses Mutant EGFR-Associated Human Non-Small Cell Lung Cancers 11" 2014 Molecular Cancer Therapeutics, 13(3):617-629.
Olsen, "Development of small molecule inhibitors of the breast cancer oncoprotein APOBEC3B," Division of Medicinal Chemistry Scientific Abstracts for the 248th National Meeting and Exposition (Abstract MEDI 309), 2014, pp. 1-394.
Brown, "A rabbit monoclonal antibody against the antiviral and cancer genomic DNA mutating enzyme APOBEC3B" Jan. 2019 *bioRxiv.* Online: https://www.biorxiv.org/content/biorxiv/early/2019/01/07/513341.full-text.pdf. 32 pages.

(Continued)

*Primary Examiner* — Laura B Goddard
(74) *Attorney, Agent, or Firm* — Mueting Raasch Group

(57) ABSTRACT

Hybridoma cell lines produce monoclonal antibodies that specifically bind to an APOBEC3 protein. The antibodies can be used in various methods. In some aspects, an anti-APOBEC3 antibody may be immobilized to a substrate. In another aspect, this disclosure provides a vector that includes a nucleic acid sequence encoding antibody produced by a hybridoma cell line that produces an antibody that specifically binds to an APOBEC3 protein.

9 Claims, 11 Drawing Sheets
Specification includes a Sequence Listing.

(56) References Cited

OTHER PUBLICATIONS

Carpenter, "Methylcytosine and normal cytosine deamination by the foreign DNA restriction enzyme APOBEC3A" Oct. 2012 *J. Biol Chem.*, 287(41):34801-8.
Harris, "Molecular mechanism and clinical impact of APOBEC3B-catalyzed mutagenesis in breast cancer" Jan. 2015 *Breast Cancer Res.*, 17:8. 10 pgs.
Lackey, "Subcellular localization of the APOBEC3 proteins during mitosis and implications for genomic DNA deamination" Mar. 2013 *Cell Cycle*, 12(5):762-72.
U.S. Appl. No. 62/186,462, filed Jun. 30, 2015, Harris et al.
U.S. Appl. No. 62/186,109, filed Jun. 29, 2015, Harris et al.
U.S. Appl. No. 62/186,228, filed Jun. 29, 2015, Harris et al.
U.S. Appl. No. 62/187,643, filed Jul. 1, 2015, Harris et al.
U.S. Appl. No. 62/187,623, filed Jul. 1, 2015, Harris et al.
U.S. Appl. No. 62/312,115, filed Mar. 23, 2016, Harris et al.
International Patent Application No. PCT/US2016/040011, filed Jun. 29, 2016; International Search Report / Written Opinion, dated Dec. 12, 2016; 16 pgs.
International Patent Application No. PCT/US2016/040011, filed Jun. 29, 2016; International Preliminary Report on Patentability, dated Jan. 11, 2018; 11 pgs.
International Patent Application No. PCT/US2016/040032, filed Jun. 25, 2016; International Search Report / Written Opinion, dated Sep. 22, 2016; 13 pgs.
International Patent Application No. PCT/US2016/040032, filed Jun. 29, 2016; International Preliminary Report on Patentability, dated Jan. 2, 2018; 6 pgs.
International Patent Application No. PCT/US2016/040060, filed Jun. 29, 2016; International Search Report / Written Opinion, dated Jan. 11, 2018; 9 pgs.
International Patent Application No. PCT/US2016/040060, filed Jun. 29, 2016; International Preliminary Report on Patentability, dated Oct. 4, 2016; 15 pgs.
International Patent Application No. PCT/US2017/023783, filed Mar. 23, 2017; International Search Report / Written Opinion, dated Jun. 15, 2017; 18 pgs.
International Patent Application No. PCT/US2017/023783, filed Mar. 23, 2017; International Search Report / Written Opinion International Preliminary Report on Patentability, dated Oct. 4, 2018; 9 pgs.
A2780. Online: https://www.phe-culturecollections.org.uk. Accessed: Dec. 12, 2018. 6 pgs.
AEB071 (Medchemexpress, Monmouth Junction, NJ), Online: https://www.abcam.com/sotrastaurin-ab219867.html. Retrieved Sep. 18, 2018. 1 pg.
Alexandrov, "Signatures of mutational processes in human cancer" 2013 *Nature*, 500:415-21.
American Type Culture Collection, "ATCC No. ATCC CRL-1500," (ZR-75-1). Online: https://www.atcc.org/~/ps/CRL-1500.ashx. Retrieved on Dec. 12, 2018. 3 pgs.
American Type Culture Collection, "ATCC No. ATCC CRL-3216," (293T) organism: *Homo sapiens*, human; Manassas, VA. Retrieved on Dec. 14, 2018. Online: https://www.atcc.org/products/all/CRL-3216.aspx; 3 pgs.
American Type Culture Collection, "ATCC No. ATCC CRL-7920," (DoTc2 4510). Online: https://www.atcc.org/~/ps/CRL-7920.ashx. Retrieved on Dec. 14, 2018. 3 pgs.
American Type Culture Collection, "ATTC No. ATCC CRL-10317," (MCF10A) organism: *Homo sapiens*, human; Manassas, VA. Retrieved on Dec. 14, 2018. Online: https://www.atcc.org/Products/All/CRL-10317.aspx. 3 pgs.
American Type Culture Collection, "ATTC No. ATCC HCC1569," (CRL-2330) organism: *Homo sapiens*, human; Manassas, VA. Retrieved on Sep. 17, 2018. Online: https://atcc.org/~/ps/CRL-2330.ashx. 3 pgs.
American Type Culture Collection, "ATTC No. ATCC HCC1806," (CRL-2335) organism: *Homo sapiens*, human; Manassas, VA. Retrieved on Sep. 18, 2018. Online: https://atcc.org/~/ps/CRL-2335.ashx. 3 pgs.
American Type Culture Collection, "ATTC No. ATCC HTB-1," (J82) organism: *Homo sapiens*, human; Manassas, VA. Retrieved on Dec. 14, 2018. Online: https://atcc.org/~/ps/HTB-1.ashx. 3 pgs.
American Type Culture Collection, "ATTC No. ATCC HTB-2," (RT4) organism: *Homo sapiens*, human; Manassas, VA. Retrieved on Sep. 18, 2018. Online: https://www.atcc.org/~/ps/HTB-2.ashx. 3 pgs.
American Type Culture Collection, "ATTC No. ATCC HTB-4," (T24) organism: *Homo sapiens*, human; Manassas, VA. Retrieved on Dec. 14, 2018. Online: https://www.atcc.org/products/all/HTB-4.aspx. 3 pgs.
American Type Culture Collection, "ATTC No. ATCC HTB-5," (TCCSUP) organism: *Homo sapiens*, human; Manassas, VA. Retrieved on Sep. 18, 2018. Online: https://www.atcc.org/~/ps/HTB-5.ashx. 3 pgs.
American Type Culture Collection, "ATCC No. ATCC HTB-96," (U-2 OS) Retrieved on Dec. 14, 2018. Online: https://www.atcc.org/products/all/HTB-96.aspx. 3 pgs.
American Type Culture Collection, "ATTC No. ATCC HTB-131D," (MDA-MB-453) organism: *Homo sapiens*, human; Manassas, VA. Retrieved on Sep. 18, 2018. Online: https://www.atcc.org/~/ps/HTB-131.ashx. 3 pgs.
American Type Culture Collection, "ATTC No. ATCC HTB-132," (MBA-MB-468) organism: *Homo sapiens*, human; Manassas, VA. Retrieved on Dec. 14, 2018. Online: https://www.atcc.org/Products/All/HTB-132.aspx. 3 pgs.
Bast, "The biology of ovarian cancer: new opportunities for translation" 2009 *Nat Rev Cancer*, 9:415-28.
Burns, "APOBEC3B is an enzymatic source of mutation in breast cancer" 2013 *Nature*, 494:366-70.
Burns, "Evidence for APOBEC3B mutagenesis in multiple human cancers" 2013 *Nat Genet.*, 45:977-83.
Burns, "APOBEC3B: pathological consequences of an innate immune DNA mutator" Mar. 2015 *Biomedical Journal*, 38:102-10.
Cancer Genome Atlas Network, "Comprehensive genomic characterization of head and neck squamous cell carcinomas" Jan. 28, 2015 *Nature* 517(7536):576-582.
Cancer Genome Atlas Research Network, "Integrated genomic analyses of ovarian carcinoma" 2011 *Nature*, 474:609-15 (including Erratum dated Oct. 2012).
Carita, "Dual inhibition of protein kinase C and p53-MDM2 or PKC and mTORC1 are novel efficient therapeutic approaches for uveal melanoma" May 22, 2016 *Oncotarget*, 7(23):33542-56.
Caval, "A prevalent cancer susceptibility APOBEC3A hybrid allele bearing APOBEC3B 3'UTR enhances chromosomal DNA damage" Oct. 9, 2014 *Nat Commun.*, 5:5129.
Cescon, "APOBEC3B expression in breast cancer reflects cellular proliferation, while a deletion polymorphism is associated with immune activation" 2015 *PNAS*, 112:2841-6 (published online Feb. 17, 2015).
Chan, "An APOBEC3A hypermutation signature is distinguishable from the signature of background mutagenesis by APOBEC3B in human cancers" 2015 *Nat Genet.*, 47:1067-72 (published online Aug. 10, 2015).
Chen, "Combined PKC and MEK inhibition in uveal melanoma with GNAQ and GNA11 mutations" Sep. 2014 *Oncogene*, 33(39):4724-34 (published online Oct. 21, 2013).
Coligan, *Current Protocols in Immun*. Wiley: Hoboken, NJ; 1992. Cover page, title page, sections 2.4-2.10.
Conticello, "The AID/APOBEC family of nucleic acid mutators" 2008 *Genome Biol.*, 9:229;10 pgs.
Ding, "APOBEC3G promotes liver metastasis in an orthotopic mouse model of colorectal cancer and predicts human hepatic metastasis" 2011 *J Clin Invest.*, 121:4526-36.
Di Noia, "Molecular mechanisms of antibody somatic hypermutation" 2007 *Annu Rev Biochem.*, 76:1-22.

(56) References Cited

OTHER PUBLICATIONS

Evenou, "The potent protein kinase C-selective inhibitor AEB071 (sotrastaurin) represents a new class of immunosuppressive agents affecting early T-cell activation" 2009 *J Pharmacol Exp Ther.*, 330(3):792-801.

Foxwell, "Efficient adenoviral infection with IκBα reveals that macrophage tumor necrosis factor aproduction in rheumatoid arthritis is NF-κB dependent" 1998 *PNAS*, 95:8211-5.

National Center for Biotechnology Information, National Library of Medicine, National Institutes of Health, GenBank Accession No. AAI26417.1 APOBEC3A (A3A), "apolipoprotein B mRNA editing enzyme catalytic subunit 3A [ *Homo sapiens* (human)]," [online]. Bethesda, MD [retrieved on Dec. 18, 2018]. Retrieved from the Internet: www.ncbi.nlm.nih.gov/gene?Db=gene&Cmd=DetailsSearch &Term=200315; 12 pgs.

National Center for Biotechnology Information, National Library of Medicine, National Institutes of Health, GenBank Accession No. APOBEC3B (A3B) GenBank: AAW31743.1. Online: https://www.ncbi.nlm.nih.gov/protein/56900900. Accessed: Dec. 12, 2018. 1 pg.

National Center for Biotechnology Information, National Library of Medicine, National Institutes of Health, GenBank Accession No. APOBEC3C (A3C) GenBank: AAH11739.1. Online: https://www.ncbi.nlm.nih.gov/protein/AAH11739.1. Accessed: Dec. 14, 2018. 2 pgs.

National Center for Biotechnology Information, National Library of Medicine, National Institutes of Health, GenBank Accession No. APOBEC3D (A3D) GenBank: AIC57731.1. Online: https://www.ncbi.nlm.nih.gov/protein/649129716/. Accessed: Dec. 12, 2018. 1 pg.

National Center for Biotechnology Information, National Library of Medicine, National Institutes of Health, GenBank Accession No. APOBEC3F (A3F) GenBank: AAZ38720.1. Online: https://www.ncbi.nlm.nih.gov/protein/AAZ38720.1. Accessed Dec. 12, 2018. 1 pg.

National Center for Biotechnology Information, National Library of Medicine, National Institutes of Health, GenBank Accession No. APOBEC3G (A3G) GenBank: AAZ38722.1. Online: https://www.ncbi.nlm.nih.gov/protein/AAZ38722.1. Accessed: Dec. 12, 2018. 1 pg.

National Center for Biotechnology Information, National Library of Medicine, National Institutes of Health, GenBank Accession No. APOBEC3H (A3H) GenBank: ACK77774.1. Online: https://www.ncbi.nlm.nih.gov/protein/ACK77774.1 Accessed: Dec. 14, 2018; 1 pg.

Gö6976 (Enzo Life Sciences, Inc., Farmingdale, NY). Online: http://www.enzolifesciences.com/BML-EI269/g-6976/. Retrieved Sep. 18, 2018. 2 pgs.

Gö6983 (Cayman Chemical Co., Ann Arbor, MI). Online: https://www.caymanchem.com/product/13311. Retrieved Sep. 18, 2018. 5 pgs.

Griner, "Protein kinase C and other diacylglycerol effectors in cancer" 2007 *Nat Rev Cancer*, 7(4):281-94.

Gschwendt, "Inhibition of protein kinase C mu by various inhibitors. Differentiation from protein kinase c isoenzymes" 1996 *FEBS Lett.*, 392:77-80.

Gyorffy, "Implementing an online tool for genome-wide validation of survival-associated biomarkers in ovarian-cancer using microarray data from 1287 patients" 2012 *Endocr Relat Cancer*, 19:197-208.

Hanahan, "Hallmarks of cancer: the next generation" 2011 *Cell*, 144(5):646-74.

Harlow, *Antibodies: A laboratory manual*. Cold Spring Harbor Laboratory. 1988. ISBN 0-87969-314-2. Title page, copyright page, and table of contents.

Harris, "RNA editing enzyme APOBEC1 and some of its homologs can act as DNA mutators" 2002 *Mol Cell*, 10(5): 1247-53.

Harris, "The restriction factors of human immunodeficiency virus" 2012 *Journal of Biological Chemistry*, 287:40875-83.

Henderson, "APOBEC-mediated cytosine deamination links PIK3CA helical domain mutations to human papillomavirus-driven tumor development" 2014 *Cell Rep.*, 7:1833-41.

Hu, "Lymphotoxin β receptor mediates caspase-dependent tumor cell apoptosis in vitro and tumor suppression in vivo despite induction of NF-κB activation" 2013 *Carcinogenesis*, 34(5): 1105-1114.

Hultquist, "Human and rhesus APOBEC3D, APOBEC3F, APOBEC3G, and APOBEC3H demonstrate a conserved capacity to restrict Vif-deficient HIV-1" 2011 *Journal of Virology*, 85:11220-34.

Jemal, "Global cancer statistics" 2011 *CA Cancer J Clin.*, 61(2):69-90.

Knutson, "Regulatory T cells, inherited variation, and clinical outcome in epithelial ovarian cancer" 2015 *Cancer Immunol Immunother*., 64:1495-1504 (published online Aug. 23, 2015).

Köhler, "Continuous cultures of fused cells secreting antibody of predefined specificity" 1975 *Nature*, 256:495-497.

Koning, "Defining APOBEC3 expression patterns in human tissues and hematopoietic cell subsets" 2009 *Journal of Virology*, 83:9474-85.

Kuong, "APOBEC3B mutagenesis in cancer" Sep. 2013 *Nat Genet.*, 45(9):964-965.

Kwok, "The anti-inflammatory natural product parthenolide from the medicinal herb Feverfew directly binds to and inhibits IκB kinase" 2001 *Chemistry & Biology*, 8(8), 759-766.

Lackey, "APOBEC3B and AID have similar nuclear import mechanisms" 2012 *J. Mol. Bio.*, 419(5):301-14.

Lawrence, "Mutational heterogeneity in cancer and the search for new cancer-associated genes" 2013 *Nature*, 499(7457):214-8.

Lee, "Reduction of a 4-pyrrole phenylacyl-containing peptide with trifluoroacetic acid-triisopropylsilane-phenol-H2O during solid-phase peptide synthesis and its protein kinase C α inhibitory activity" 2005 *Bioorg. Med. Chem. Lett.*, 15(9):2271-4.

Leonard, "APOBEC3B upregulation and genomic mutation patterns in serous ovarian carcinoma" 2013 *Cancer Res.*, 73 (24): 7222-31.

Leonard, "The PKC-NFκB Signaling Pathway Induces APOBEC3B Expression in Multiple Human Cancers" 2015 *Cancer Res.*, 75(21):4538-4547 (published online Sep. 29, 2015).

Leonard, "APOBEC3G expression correlates with T cell infiltration and improved clinical outcomes in high-grade serous ovarian carcinoma" Sep. 2016 *Clin Cancer Res.*, 22(18): 4746-4755 (published online Mar. 25, 2016).

Li, "Inhibiting NF-κb-inducing kinase (NIK): Discovery, structure-based design, synthesis, structure-activity relationship, and co-crystal structures" 2013 *Bioorganic & Medicinal Chemistry Letters*, 23 (5): 1238-1244.

Liddament, "APOBEC3F properties and hypermutation preferences indicate activity against HIV-1 in vivo" 2004 *Curr Biol.*, 14:1385-91.

Liu, "TNF-α gene expression in macrophages: regulation by NF-κB is independent of c-Jun or C/EBPβ" 2000 *J Immunol.*, 164:4277-85.

Llona-Minguez, "Small-molecule inhibitors of IκB kinase (IKK) and IKK-related kinases" 2013 *Pharm. Pat. Analyst*, 2(4):481-498.

Lo, "The melanoma revolution: from UV carcinogenesis to a new era in therapeutics" Nov. 21, 2014 *Science*, 346(6212):945-9.

Love, "Moderated estimation of fold change and dispersion for RNAseq data with DESeq2" Dec. 5, 2014 *Genome Biol.*, 15(12):550.

Lucifora, "Specific and nonhepatotoxic degradation of nuclear hepatitis B virus cccDNA" Mar. 14, 2014 *Science*, 343:1221-1228.

Lukashev, "Targeting the Lymphotoxin-β Receptor with Agonist Antibodies as a Potential Cancer Therapy" 2006 *Cancer Res.*, 66(19):6917-6924.

Mackay, "Targeting the protein kinase C family: are we there yet?" 2007 *Nat Rev Cancer*, 7(7):554-62.

Madsen, "Psoriasis upregulated phorbolin-1 shares structural but not functional similarity to the mRNA-editing protein Apobec-1" 1999 *J Invest Dermatol.*, 113(2):162-9.

Martiny-Baron, "Selective inhibition of protein kinase C isozymes by the indolocarbazole Gö 6976" 1993 *J Biol Chem.*, 268(13):9194-7.

Maruyama, "Oligo-capping: a simple method to replace the cap structure of eukaryotic mRNAs with oligoribonucleotides" 1994 *Gene*, 138(1-2):171-4.

(56) References Cited

OTHER PUBLICATIONS

Mehta, "IFN-α and lipopolysaccharide upregulate APOBEC3 mRNA through different signaling pathways" 2012 *J Immunol.*, 189(8):4088-103.
Monks, "Feasibility of a High-Flux Anticancer Drug Screen Using a Diverse Panel of Cultured Human Tumor Cell Lines" 1991 *J. Natl. Cancer Inst.*, 83(11):757-766.
Musi, "The phosphoinositide 3-kinase a selective inhibitor BYL719 enhances the effect of the protein kinase C inhibitor AEB071 in GNAQ/GNA11-mutant uveal melanoma cells" 2014 *Mol Cancer Ther.*, 13(5):1044-53 (published online Feb. 21, 2014).
Nabel, "Nucleic acid determinants for selective deamination of DNA over RNA by activation-induced deaminase" 2013 *PNAS*, 110(35): 14225-30.
Nielsen, "CD20+ tumor-infiltrating lymphocytes have an atypical CD27- memory phenotype and together with CD8+ T cells promote favorable prognosis in ovarian cancer" 2012 *Clin Cancer Res.*, 18:3281-92.
NIH AIDS Reagent Program, Data Sheet for Reagent "Anti-human APOBEC3B (5210-87-13)," Cat. # 12397 from Dr. Reuben Harris, Last Updated: Jan. 12, 2016; 2 pgs.
Nik-Zainal, "Mutational processes molding the genomes of 21 breast cancers" 2012 *Cell*, 149(5):979-93.
Nik-Zainal, "Association of a germline copy number polymorphism of APOBEC3A and APOBEC3B with burden of putative APOBEC-dependent mutations in breast cancer" 2014 *Nat Genet.*, 46:487-91.
Periyasamy, "APOBEC3B-Mediated Cytidine Deamination Is Required for Estrogen Receptor Action in Breast Cancer" Oct. 6, 2015 *Cell Rep.*, 13:108-21.
Pierce, " Novel inhibitors of cytokine-induced IκBα phosphorylation and endothelial cell adhesion molecule expression show anti-inflammatory effects in vivo" 1997 *J Biol Chem.*, 272(34):21096-21103.
Piperno-Neumann, "Phase I dose-escalation study of the protein kinase C (PKC) inhibitor AEB071 in patients with metastatic uveal melanoma" 2014 *J Clin Oncol.*, 32:9030.
Podolin, "Attenuation of murine collagen-induced arthritis by a novel, potent, selective small molecule inhibitor of IkappaB Kinase 2, TPCA-1 (2-[(aminocarbonyl)amino]-5-(4-fluorophenyl)-3-thiophenecarboxamide), occurs via reduction of proinflammatory cytokines and antigen-induced T cell Proliferation" Jan. 2005 *J Pharmacol Exp Ther.*, 312(1):373-381.
Poon, "Genome-wide mutational signatures of aristolochic acid and its application as a screening tool" 2013 *Sci Transl Med.*, 5(197):197ra101; 10 pgs.
Preston, "The ratios of CD8+ T cells to CD4+CD25+ FOXP3+ and FOXP3- T cells correlate with poor clinical outcome in human serous ovarian cancer" 2013 *PLoS One*, 8:e80063; 10 pgs.
Rathore, "The local dinucleotide preference of APOBEC3G can be altered from 5'-CC to 5'-TC by a single amino acid substitution" 2013 *J Mol Biol.*, 425(22):4442-54.
Rauert-Wunderlich, "The IKK inhibitor Bay 11-7082 induces cell death independent from inhibition of activation of NFκB transcription factors" 2013 *PLoS One*, 8(3):e59292; 10 pgs.
Refsland, "Quantitative profiling of the full APOBEC3 mRNA repertoire in lymphocytes and tissues: implications for HIV-1 restriction" 2010 *Nucleic Acids Res.*, 38(13):4274-84.
Refsland, "Endogenous origins of HIV-1 G-to-A hypermutation and restriction in the nonpermissive T cell line CEM2n" 2012 *PLoS Pathog.*, 8(7):e1002800; 12 pgs.
Refsland, "The APOBEC3 family of retroelement restriction factors" 2013 *Curr Top Microbiol Immunol.*, 371:1-27.
Robbiani, "Chromosome translocation, B cell lymphoma, and activation-induced cytidine deaminase" 2013 *Annu Rev Pathol.*, 8:79-103.
Roberts, "An APOBEC cytidine deaminase mutagenesis pattern is widespread in human cancers" 2013 *Nat Genet.*, 45:970-76.
Roberts, "Clustered mutations in yeast and in human cancers can arise from damaged long single-strand DNA regions" 2012 *Mol Cell*, 46(4):424-35.
Roberts, "Hypermutation in human cancer genomes: footprints and mechanisms" Nov. 24,2014 *Nat Rev Cancer*, 14:786-800 (including Erratum dated Sep. 28, 2015).
Rosse, "PKC and the control of localized signal dynamics" 2010 *Nat Rev Mol Cell Biol.*, 11(2):103-12.
Sabek, "Quantitative detection of T-cell activation markers by real-time PCR in renal transplant rejection and correlation with histopathologic evaluation" 2002 *Transplantation*, 74:701-7.
Sagoo, "Combined PKC and K inhibition for treating metastatic uveal melanoma" 2014; *Oncogene*, 33(39):4722-3 (published online Jan. 13, 2014).
Saraconi, "The RNA editing enzyme APOBEC1 induces somatic mutations and a compatible mutational signature is present in esophageal adenocarcinomas" Jul. 31, 2014 *Genome Biol.*, 15(7):417.
Sato, "Intraepithelial CD8+ tumor-infiltrating lymphocytes and a high CD8+/regulatory T cell ratio are associated with favorable prognosis in ovarian cancer" 2005 *Proc Natl Acad Sci USA*, 102:18538-43.
Schuyer, "Reduced expression of BAX is associated with poor prognosis in patients with epithelial ovarian cancer: a multifactorial analysis of TP53, p21, BAX and BCL-2" 2001 *Br J Cancer*, 85:1359-67.
Schwartz, "T cell anergy" 2003 *Annu Rev Immunol.*, 21:305-34.
Seidman, "The histologic type and stage distribution of ovarian carcinomas of surface epithelial origin" 2004 *Int J Gynecol Pathol.*, 23:41-4.
Sieuwerts, "Elevated APOBEC3B correlates with poor outcomes for estrogen-receptor-positive breast cancers" 2014 *Horm Cancer*, 5:405-13.
Snyder, "Genetic basis for clinical response to CTLA-4 blockade in melanoma" 2014 *N Engl J Med.*, 371:2189-99.
Sohn, "Somatic hypermutation and outcomes of platinum based chemotherapy in patients with high grade serous ovarian cancer" 2012 *Gynecol Oncol.*, 126:103-8.
Spitaler, "Protein kinase C and beyond" 2004 *Nat Immunol.*, 5:785-90.
Stenglein, "APOBEC3 proteins mediate the clearance of foreign DNA from human cells" 2010 *Nat Struct Mot Biol.*, 17(2):222-9.
Straus, "TNFα and IL-17 cooperatively stimulate glucose metabolism and growth factor production in human colorectal cancer cells" 2013 *Molecular Cancer*, 12:78; 13 pgs.
Strickson, "The anti-inflammatory drug BAY 11-7082 suppresses the MyD88-dependent signalling network by targeting the ubiquitin system" 2013 *Biochem J.*, 451:427-37.
Swanton, "APOBEC enzymes: mutagenic fuel for cancer evolution and heterogeneity" 2015 *Cancer Discovery*, 5:704-12 (published online Jun. 19, 2015).
Thielen, "Innate immune signaling induces high levels of TC-specific deaminase activity in primary monocytederived cells through expression of APOBEC3A isoforms" 2010 *Journal of Biological Chemistry*, 285(36):27753-66.
Toullec, "The bisindolylmaleimide GF 109203X is a potent and selective inhibitor of protein kinase C" 1991 *Journal of Biological Chemistry*, 266:15771-81.
Towbin, "Electrophoretic transfer of proteins from polyacrylamide gels to nitrocellulose sheets: procedure and some applications" 1979 *Proc Natl Acad Sci USA*, 76(9):4350-4.
Trapnell, "Differential gene and transcript expression analysis of RNA-seq experiments with TopHat and Cufflinks" 2012 *Nat Protoc.*, 7(3):562-78.
Tsuboi, APOBEC3B high expression status is associated with aggressive phenotype in Japanese breast cancers. 2016 *Breast Cancer*, 23(5):780-8 (published online Oct. 17, 2015).
Vallabhapurapu, "Regulation and function of NF-kappaB transcription factors in the immune system" 2009 *Annu Rev Immunol.*, 27:693-733.
Van Raamsdonk, "Frequent somatic mutations of GNAQ in uveal melanoma and blue naevi" 2009 *Nature*, 457:599-602.
Van Raamsdonk, "Mutations in GNA11 in uveal melanoma" 2010 *N Engl J Med.*, 363(23):2191-9.
Verschuere, "Cigarette smoking alters epithelial apoptosis and immune composition in murine GALT" 2011 *Lab Invest.*, 91:1056-67.

(56) References Cited

OTHER PUBLICATIONS

Vieira, "Human papillomavirus E6 triggers upregulation of the antiviral and cancer genomic DNA deaminase APOBEC3B" Dec. 23, 2014 *mBio* 5(6):e02234-1; 8 pgs.

Voller, "New serological test for malaria antibodies" 1975 *Br Med J.*, 1:659-61.

Wagner, "Discovery of 3-(1H-indol-3-yl)-4-[2-(4-methylpiperazin-1-yl)quinazolin-4-yl]pyrrole-2,5-dione (AEB071), a potent and selective inhibitor of protein kinase C isotypes" 2009 *J Med Chem.*, 52:6193-6.

Wagner, "Structure-activity relationship and pharmacokinetic studies of sotrastaurin (AEB071), a promising novel medicine for prevention of graft rejection and treatment of psoriasis" 2011 *J Med Chem.*, 54(17):6028-39.

Warren, "APOBEC3A functions as a restriction factor of human papillomavirus" Jan. 2015 *Journal of Virology*, 89(1):688-702 (published online Oct. 29, 2014).

Weichselbaum, " Radioresistant tumor cells are present in head and neck carcinomas that recur after radiotherapy" 1988, *Int. J. Radiat. Oncol. Biol. Phys.*, 15:575-579.

Wichkham, ggplot2: elegant graphics for data analysis. New York: Springer Publishing Company; 2009.

Wilchek, "Affinity chromatography" 1984 Methods Enzymol., 104:3-55. Review. PMID:6371446.

Wu, "Protein kinase C inhibitor AEB071 targets ocular melanoma harboring GNAQ mutations via effects on the PKC/Erk1/2 and PKC/NF-κB pathways" Sep. 2012 Mol Cancer Ther., 11(9): 1905-14.

Xu, "High APOBEC3B expression is a predictor of recurrence in patients with low-risk clear cell renal cell carcinoma" Aug. 2015 Urol Oncol., 33:340.e1-8 (published online Jun. 4, 2015).

Xu, "SN52, a novel nuclear factor-κB inhibitor, blocks nuclear import of RelB:p52 dimer and sensitizes prostate cancer cells to ionizing radiation" 2008 *Mol. Cancer Ther.*, 7(8):2367-2376.

Yuen, "Phase I Study of an Antisense Oligonucleotide to Protein Kinase C-a (ISIS 3521/CGP 64128A) in Patients with Cancer" 1999 *Clinical Cancer Research*, 5(11):3357-3363.

Zhang, "The roles of APOBEC3B in gastric cancer" May 15, 2015 *Int J Clin Exp Pathol.*, 8:5089-96 (published online May 1, 2015).

Zhang, "Intratumoral T cells, recurrence, and survival in epithelial ovarian cancer" 2003 *N Engl J Med.*, 348:203-13.

Zheng, "Molecular regulation of T-cell anergy" 2008 *EMBO Rep.*, 9:50-5.

Boiehard, "High expression of PD-1 ligands is associated with kataegis mutational signature and APOBEC3 alterations" Jan. 2017 *Oncoimmunology*, 6(3):e1284719.

Gao et al., "Molecular Cloning of a Proteolytic Antibody Light Chain," 1994, *The Journal of Biological Chemistry*, 269(51):32389-93.

Gonzalez-Guerrico, "Phorbol Ester-induced Apoptosis in Prostate Cancer Cells via Autocrine Activation of the Extrinsic Apoptotic Cascade: a key role for protein kinase c[delta]" 2005 *Journal of Biological Chemistry*, 280(47):38982-38991.

Jing, "Combined immune checkpoint protein blockade and low dose whole body irradiation as immunotherapy for myeloma" Jan. 20, 2015 *Journal for ImmunoTherapy of Cancer, Biomed Central Ltd*, London, UK, 3(1):2 (15 pages).

Laune et al., "Systematic Exploration of the Antigen Binding Activity of Synthetic Peptides Isolated from the Variable Regions of Immunoglobulins," 1997, *The Journal of Biological Chemistry*, 272(49):30937-44.

Maruyama, "Classical NF-κB pathway is responsible for APOBEC3B expression in cancer cells" 2016 *Biochemical and Biophysical Research Communications*, 478(3):1466-1471 (published online Aug. 27, 2016).

Monnet et al., "Synthetic Peptides Derived from the Variable Regions of an Anti-CD4 Monoclonal Antibody Bind to CD4 and Inhibit HIV-1 Promoter Activation in Virus-infected Cells," 1999, *The Journal of Biological Chemistry*, 274(6):3789-96.

Qiu et al, "Small antibody mimetics comprising two complementary-determining regions and a framework region for tumor targeting," 2007, *Nature Biotechnology*, 25(8):921-29.

Quiocho, "Protein engineering: Making of the minibody," 1993, *Nature*, 362:293-94.

Rizvi, "Mutational landscape determines sensitivity to PD-1 blockade in non-small cell lung cancer" 2015 *Science*, 348(6230):124-128 (published online Mar. 12, 2015; corrected Feb. 11, 2016) + Supplementary Materials (31 pages).

Tahara, "Activation of Protein Kinase C by Phorbol 12-Myristate 13-Acetate suppresses the growth of lung cancer cells through KLF6 induction" 2009 *Cancer Biology & Therapy*, 8(9):801-807.

Vaughan et al., "Of Minibody, Camel and Bacteriophage," 2001, *Combinatorial Chemistry & High Throughput Screening*, 4(5):417-30.

European Patent Application No. 17 77 1143.9, filed Mar. 23, 2017; Supplementary European Search Report dated Oct. 25, 2019 (11 pages).

Lan et al., "APOBEC3G expression is correlated with poor prognosis in colon carcinoma patients with hepatic metastasis" Int J Clin Exp Med, 2014; 7(3):665-72.

Wang et al., "Mucosal immunization in macaques upregulates the innate APOBEC 3G anti-viral factor in CD4+ memory T cells" Vaccine, Feb. 5, 2009; 27(6):870-81. Epub Dec. 11, 2008.

Xia, "Effector pathway of the antiviral effect of interferons in Hepatitis B Virus: infection Table of contents" Jul. 1, 2013; pp. 1-150. Retrieved online: <push-zb.helmholtz-muenchen.de/deliver.php?id=7115>.

Yan et al., "Increased APOBEC3B Predicts Worse Outcomes in Lung Cancer: A Comprehensive Retrospective Study" J Cancer, Mar. 19, 2016; 7(6):618-25. eCollection 2016.

\* cited by examiner

ANTI-APOBEC3 ANTIBODIES AND METHODS OF MAKING AND USING

CROSS-REFERENCE TO RELATED APPLICATION

This application is the § 371 U.S. National Stage of International Application No. PCT/US2016/040011, filed Jun. 29, 2016, which claims priority to U.S. Provisional Application No. 62/186,109, filed Jun. 29, 2015, each of which is incorporated herein by reference in its entirety.

SEQUENCE LISTING

This application contains a Sequence Listing electronically submitted via EFS-Web to the United States Patent and Trademark Office as an ASCII text file entitled "2016-06-23-SequenceListing_ST25.txt" having a size of 72 kilobytes and created on Jun. 23, 2016. The information contained in the Sequence Listing is incorporated by reference herein.

BACKGROUND

APOBEC3B is an antiviral enzyme that has been implicated in cancer mutagenesis. APOBEC3B is one of seven human cytidine deaminases in the APOBEC3 (A3) family. The A3 family includes APOBEC3A (A3A); APOBEC3B (A3B); APOBEC3C (A3C); APOBEC3D (A3D) APOBEC3F (A3F); APOBEC3G (A3G); APOBEC3H (A3H).

SUMMARY

This disclosure describes antibodies that specifically bind to an APOBEC3 protein. In some embodiments, the antibody can specifically bind APOBEC3B.

In some embodiments, the antibody can be a monoclonal antibody. In some of these embodiments, the monoclonal antibody is produced by hybridoma cell line 5206-235-07. In other embodiments, the monoclonal antibody is produced by hybridoma cell line 5210-76-29. In other embodiments, the monoclonal antibody is produced by hybridoma cell line 5210-08-15. In other embodiments, the monoclonal antibody is produced by hybridoma cell line 5211-110-19. In other embodiments, the monoclonal antibody is produced by hybridoma cell line 5211-142-12. In other embodiments, the monoclonal antibody is produced by hybridoma cell line 5210-55-19. In other embodiments, the monoclonal antibody is produced by hybridoma cell line 5210-87-13.

In some embodiments, the antibody can include at least one of the amino acid sequences SEQ ID NO:8, SEQ ID NO:9, SEQ ID NO:10, SEQ ID NO:11, SEQ ID NO:12, SEQ ID NO:13, or SEQ ID NO:14.

In some embodiments, the antibody can include at least one of the amino acid sequences SEQ ID NO:22, SEQ ID NO:23, SEQ ID NO:24, SEQ ID NO:25, SEQ ID NO:26, SEQ ID NO:27, or SEQ ID NO:28.

In some embodiments, the monoclonal antibody can include a heavy chain and a light chain, wherein the light chain includes three complementarity determining regions (CDRs), and further wherein the first light chain CDR (CDR1) comprises at least one of the amino acid sequences QSVYNNND (SEQ ID NO:29), QSLYRNKN (SEQ ID NO:32), QNIYSN (SEQ ID NO:35), QSVYNNKN (SEQ ID NO:38), HSVYNNNW (SEQ ID NO:40), QSVYKNKN (SEQ ID NO:42), or ESVFKKNW (SEQ ID NO:44).

In some embodiments, the monoclonal antibody includes a heavy chain and a light chain, wherein the light chain includes three complementarity determining regions (CDRs), and further wherein the second light chain CDR (CDR2) includes at least one of the amino acid sequences RAS (SEQ ID NO:30), YAS (SEQ ID NO:33), or GAS (SEQ ID NO:36).

In some embodiments, the monoclonal antibody includes a heavy chain and a light chain, wherein the light chain includes three complementarity determining regions (CDRs), and further wherein the third light chain CDR (CDR3) includes at least one of the amino acid sequences LGSYDDDVDTCA (SEQ ID NO:31), QGEFSCSSADCFA (SEQ ID NO:34), QSYVYSSSTADT (SEQ ID NO:37), LGEFYCSSIDCLV (SEQ ID NO:39), QGGYSSGDGIA (SEQ ID NO:41), LGEFSCHSVDCLA (SEQ ID NO:43), or AGAFDGNIYP (SEQ ID NO:45).

In some embodiments, the monoclonal antibody includes a heavy chain and a light chain, wherein the heavy chain includes three complementarity determining regions (CDRs), and further wherein the first heavy chain CDR (CDR1) includes at least one of the amino acid sequences GFDFSS (SEQ ID NO:46), GFSFSRG (SEQ ID NO:49), GFSFSDG (SEQ ID NO:52), GFSLSS (SEQ ID NO:55), or GFSISS (SEQ ID NO:61).

In some embodiments, the monoclonal antibody comprises a heavy chain and a light chain, wherein the heavy chain includes three complementarity determining regions (CDRs), and further wherein the second heavy chain CDR (CDR2) includes at least one of the amino acid sequences including YIDPVFG (SEQ ID NO:47), DMNIIAD (SEQ ID NO:50), CIYDASG (SEQ ID NO:53), FINSDN (SEQ ID NO:56), IISSSG (SEQ ID NO:58), or SISSGG (SEQ ID NO:61).

In some embodiments, the monoclonal antibody includes a heavy chain and a light chain, wherein the heavy chain includes three complementarity determining regions (CDRs), and further wherein the third heavy chain CDR (CDR3) includes at least one of the amino acid sequences FCARST (SEQ ID NO:48), FCVSGS (SEQ ID NO:51), FCVKTD (SEQ ID NO:54), FCATYR (SEQ ID NO:57), FCAREG (SEQ ID NO:59), or FCGS (SEQ ID NO:62).

In another aspect, this disclosure describes methods that involve using any of the antibodies summarized above. Some of these methods involve using the antibody as research reagent. Other methods involve using the antibody for at least one of a diagnostic test and a prognostic test.

In some embodiments, the method can include detecting expression of one or more APOBEC3 (A3) proteins. In some of these embodiments, the method can include detecting expression of APOBEC3B (A3B).

In some embodiments, the method can include performing at least one of enzyme-linked immunosorbent assays (ELISA), immunoblotting (IB), immunoprecipitation (IP), immunohistochemistry (IHC), immunofluorescent microscopy (IF), and flow cytometry (FLOW).

In another aspect, this disclosure describes a method of producing an antibody. Generally, the method includes immunizing a host animal with at least one of WYKFDENYAFLHRTLKEILRYLMD (SEQ ID NO:63) and PFQPWDGLEEHSQALSGRLRAILQNQGN (SEQ ID NO:64), and harvesting a cell that produces an antibody that specifically binds to one or more members of the APOBEC3 family. In some embodiments, the method can involve immunizing the host animal with both WYKFDENYAFLHRTLKEILRYLMD (SEQ ID NO:63) and PFQPWDGLEEHSQALSGRLRAILQNQGN (SEQ ID NO:64).

In another aspect, this disclosure describes a device that includes any embodiment of antibody summarized above immobilized to a substrate.

In another aspect, this disclosure describes hybridoma cell lines that produce an antibody that specifically binds to an APOBEC3 protein.

In another aspect, this disclosure describes a vector that includes a nucleic acid sequence encoding antibody produced by a hybridoma cell line that produces an antibody that specifically binds to an APOBEC3 protein.

As used herein, an "antibody" and "antibodies" (immunoglobulins) refer to at least one of a monoclonal antibody (including a full-length monoclonal antibody), a polyclonal antibody preparation, a multispecific antibody (e.g., bispecific antibodies) formed from at least two intact antibodies, a human antibody, a humanized antibody, a camelized antibody, a chimeric antibody, a single-chain Fv (scFv), a single-chain antibody, a single domain antibody, a domain antibody, an antibody fragment including, without limitation, an Fab fragment, an F(ab')$_2$ fragment, an antibody fragment that exhibits the desired biological activity, a disulfide-linked Fv (sdFv), an intrabody, or an epitope-binding fragment of any of the above. In particular, antibody includes an immunoglobulin molecule and an immunologically active fragment of an immunoglobulin molecule, i.e., a molecule that contains an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

A "monoclonal antibody," as used herein, refers to an antibody, as defined above, obtained from a population of substantially homogeneous antibodies, i.e., the individual antibodies included in the population are identical except for possible naturally occurring mutations that may be present in minor amounts. Monoclonal antibodies are highly specific, being directed against a single antigenic site. Furthermore, in contrast to polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by immortal hybridoma cells that are uncontaminated by other immunoglobulin producing cells. Alternatively, the monoclonal antibody may be produced by cells stably or transiently transfected with the heavy and light chain genes encoding the monoclonal antibody. The modifier "monoclonal" indicates the character of the antibody, as defined above, as being obtained from a substantially homogeneous population of antibodies, and is not to be construed as requiring engineering of the antibody by any particular method. The term "monoclonal" is used herein to refer to an antibody, as defined above, that is derived from a clonal population of cells, including any eukaryotic, prokaryotic, or phage clone, and not the method by which the antibody was engineered.

An "antigen" and variations thereof refer to any material capable of raising an immune response in a subject challenged with the material. In various embodiments, an antigen may raise a cell-mediated immune response, a humoral immune response, or both. Suitable antigens may be synthetic or occur naturally and, when they occur naturally, may be endogenous (e.g., a self-antigen) or exogenous. Suitable antigenic materials include but are not limited to peptides or polypeptides (including a nucleic acid, at least a portion of which encodes the peptide or polypeptide); lipids; glycolipids; polysaccharides; carbohydrates; polynucleotides; prions; live or inactivated bacteria, viruses, fungi, or parasites; and bacterial, viral, fungal, protozoal, tumor-derived, or organism-derived immunogens, toxins or toxoids. An antigen may include one or more epitopes.

"Epitope" refers to a chemical moiety that exhibits specific binding to an antibody.

"Isolated" and variations thereof refer to a polypeptide that has been removed from its natural environment to any degree. For instance, an isolated polypeptide is a polypeptide that has been removed from a cell, and many of the other polypeptides, nucleic acids, and other cellular material of its natural environment are no longer present. The term "isolated" does not convey any specific degree to which the other cellular components are removed.

"Protein" refers to any sequence of two or more amino acid residues without regard to the length of the sequence, as well as any complex of two or more separately translated amino acid sequences. Protein also refers to amino acid sequences chemically modified to include a carbohydrate, a lipid, a nucleotide sequence, or any combination of carbohydrates, lipids, and/or nucleotide sequences. As used herein, "protein," "peptide," and "polypeptide" are used interchangeably.

"Purified" and variations thereof refer to preparations in which the presence of a particular component is enriched, to any degree, relative to the unpurified starting material. Purification may be stated in any suitable terms such as, for example, increasing the concentration of the particular component in the preparation, increasing the molecular or weight/weight ratio of the particular component compared to a second component, etc.

"Specific" and variations thereof refer to having a differential or a non-general affinity, to any degree, for a particular target. As used herein, antibody that can "specifically bind" a polypeptide is antibody that interacts with an epitope of an antigen that induced the synthesis of the antibody, or interacts with a structurally related epitope. Accordingly, in describing an antibody, the terms "specific" and "specifically binds" do not imply or require that the antibody binds to one and only one target molecule.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each

BRIEF DESCRIPTION OF THE FIGURES

FIG. 8 shows the alignment of anti-human A3B hybridoma Ig light chain sequences. (A) A ClustalW alignment of anti-human A3B hybridoma Ig light chain nucleotide sequences including the Ig light chain nucleotide sequence from hybridoma cell line 5206-235-7 (SEQ ID NO:1), the Ig light chain nucleotide sequence from hybridoma cell line 5210-76-29 (SEQ ID NO:2), the Ig light chain nucleotide sequence from hybridoma cell line 5210-8-15 (SEQ ID NO:3), the Ig light chain nucleotide sequence from hybridoma cell line 5211-110-19 (SEQ ID NO:4); the Ig light chain nucleotide sequence from hybridoma cell line 5211-142-12 (SEQ ID NO:5), the Ig light chain nucleotide sequence from hybridoma cell line 5210-55-19 (SEQ ID NO:6), and the Ig light chain nucleotide sequence from hybridoma cell line 5210-87-13 (SEQ ID NO:7). The peptide number indicates the peptide that was used in the original immunization; A3 binding specificity is listed on the right. (B) A ClustalW alignment of anti-human A3B hybridoma Ig light chain protein sequences including the Ig light chain protein sequence from hybridoma cell line 5206-235-7 (SEQ ID NO:8), the Ig light chain protein sequence from hybridoma cell line 5210-76-29 (SEQ ID NO:9), the Ig light chain protein sequence from hybridoma cell line 5210-8-15 (SEQ ID NO:10), the Ig light chain protein sequence from hybridoma cell line 5211-110-19 (SEQ ID NO:11), the Ig light chain protein sequence from hybridoma cell line 5211-142-12 (SEQ ID NO:12), the Ig light chain protein sequence from hybridoma cell line 5210-55-19 (SEQ ID NO:13), the Ig light chain protein sequence from hybridoma cell line 5210-87-13 (SEQ ID NO:14). The alignment shows framework (FR) domains and complementarity determining regions (CDR). Identical amino acids (*) and similar amino acids (:) are indicated below the sequence. The peptide number indicates the peptide that was used in the original immunization A3 binding specificity is listed on the right.

FIG. 9 shows the alignment of anti-human A3B hybridoma Ig heavy chain sequences. (A) A ClustalW alignment of anti-human A3B hybridoma Ig heavy chain nucleotide sequences including the Ig heavy chain nucleotide sequence from hybridoma cell line 5206-235-7 (SEQ ID NO:15), the Ig light heavy nucleotide sequence from hybridoma cell line 5210-76-29 (SEQ ID NO:16), the Ig heavy chain nucleotide sequence from hybridoma cell line 5210-8-15 (SEQ ID NO:17), the Ig heavy chain nucleotide sequence from hybridoma cell line 5211-110-19 (SEQ ID NO:18); the Ig heavy chain nucleotide sequence from hybridoma cell line 5211-142-12 (SEQ ID NO:19), the Ig heavy chain nucleotide sequence from hybridoma cell line 5210-55-19 (SEQ ID NO:20), and the Ig heavy chain nucleotide sequence from hybridoma cell line 5210-87-13 (SEQ ID NO:21). The peptide number indicates the peptide that was used in the original immunization; A3 binding specificity is listed on the right. (B) A ClustalW alignment of anti-human A3B Ig heavy chain protein sequences including the Ig heavy chain protein sequence from hybridoma cell line 5206-235-7 (SEQ ID NO:22), the Ig heavy chain protein sequence from hybridoma cell line 5210-76-29 (SEQ ID NO:23), the Ig heavy chain protein sequence from hybridoma cell line 5210-8-15 (SEQ ID NO:24), the Ig heavy chain protein sequence from hybridoma cell line 5211-110-19 (SEQ ID NO:25), the Ig heavy chain protein sequence from hybridoma cell line 5211-142-12 (SEQ ID NO:26), the Ig heavy chain protein sequence from hybridoma cell line 5210-55-19 (SEQ ID NO:27), the Ig heavy chain protein sequence from hybridoma cell line 5210-87-13 (SEQ ID NO:28). The alignment shows framework (FR) domains, complementarity determining regions (CDR), diversity (D) and joining (JH) domains. Identical amino acids (*) and similar amino acids (:) are indicated below the sequence; A3 binding specificity is listed on the right.

DETAILED DESCRIPTION OF ILLUSTRATIVE EMBODIMENTS

Figure 1:
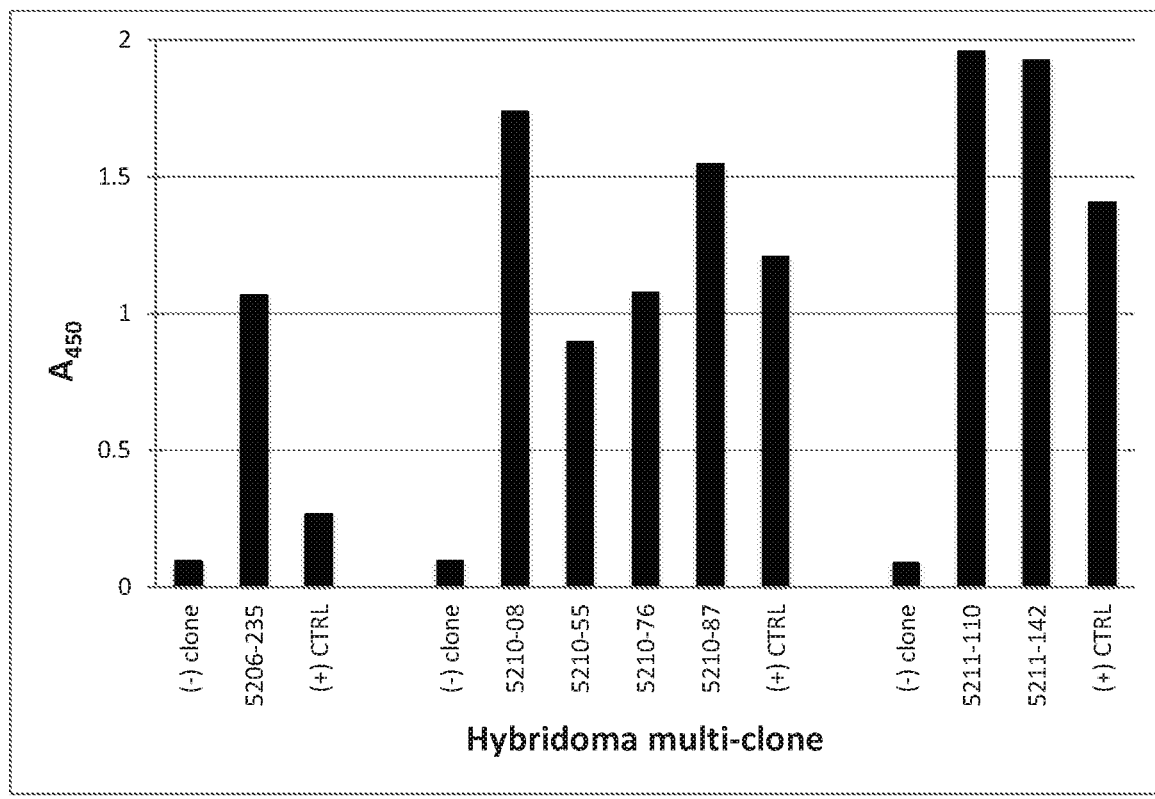
FIG. 1 shows an ELISA screen of mAb-containing supernatants from hybridoma clones. Cell media supernatant from hybridoma clones (5206-235, 5210-08, 5210-55, 5210-76, 5210-87, 5211-110, and 5210-142) was assayed for binding to A3Bctd-myc-(HIS)$_6$ purified protein (A3B-CTD) in a standard ELISA assay. Binding was detected with an anti-rabbit HRP secondary antibody (1:5000), visualized with tetramethylbenzidine (TMB) and quantified by spectroscopy at 450 nm. The negative control in this assay was cell-free media supernatant from a hybridoma clone that did not express anti-A3B, and the positive control was a rabbit anti-A3G antibody (NIH AIDS Reagent Program 10201).

This disclosure describes antibodies that bind to cytidine deaminases in the APOBEC3 (A3) family, in particular APOBEC3B; hybridomas that produce such antibodies; and methods of making antibodies that bind to members of the APOBEC3 (A3) family, in particular APOBEC3B. APOBEC3B is an antiviral enzyme that has been implicated in cancer mutagenesis and is one member of a family of cytidine deaminases in APOBEC3 (A3) family. APOBEC3B is a difficult protein to purify, and this difficulty and its homology to related APOBEC3 family members have previously made the development of antibodies specific for APOBEC3B difficult. The antibodies described herein provide valuable reagents for studying the enzymes of the APOBEC3 (A3) family, in particular APOBEC3B.

This disclosure also describes methods of making antibodies that specifically bind to one or more members of the APOBEC3 (A3) family, in particular APOBEC3B. One embodiment is a method of using epitopes specific to APOBEC3B for the generation of antibodies that specifically bind to APOBEC3B.

This disclosure further describes methods of using antibodies that specifically bind to one or more members of the APOBEC3 (A3) family, in particular APOBEC3B.

Antibodies that Bind APOBEC3 Proteins

In some embodiments, the antibodies described herein bind members of the APOBEC3 (A3) family, in particular APOBEC3B. In some embodiments, the antibodies bind to primate APOBEC3 (A3) proteins, including, for example, human APOBEC3 (A3) proteins, including, for example, human APOBEC3B (A3B).

In one embodiment, an antibody that binds to members of the APOBEC3 (A3) family, in particular APOBEC3B, may have one or more sequences present in the heavy and light chains of the antibodies produced by one or more of the following hybridomas: 5206-235-07, 5210-76-29, 5210-08-15, 5211-110-19, 5211-142-12, 5210-55-19, and 5210-87-13. The amino acid sequences for the light chains of each hybridoma are identified as SEQ ID NO:8, SEQ ID NO:9, SEQ ID NO:10, SEQ ID NO:11, SEQ ID NO:12, SEQ ID NO:13, and SEQ ID NO:14, respectively. The amino acid sequences for the heavy chains of each hybridoma are identified as SEQ ID NO:22, SEQ ID NO:23, SEQ ID NO:24, SEQ ID NO:25, SEQ ID NO:26, SEQ ID NO:27, and SEQ ID NO:28, respectively.

Figure 8:
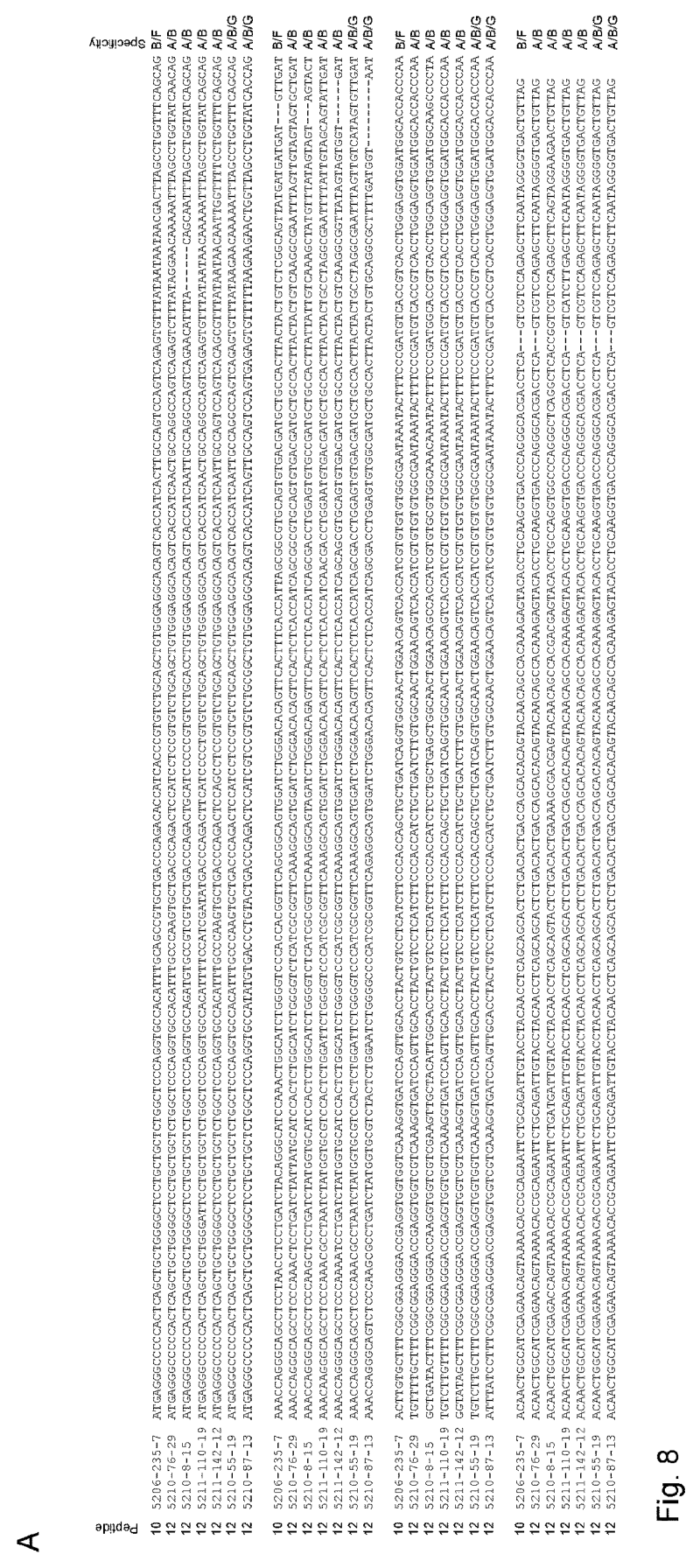
Figure 8:
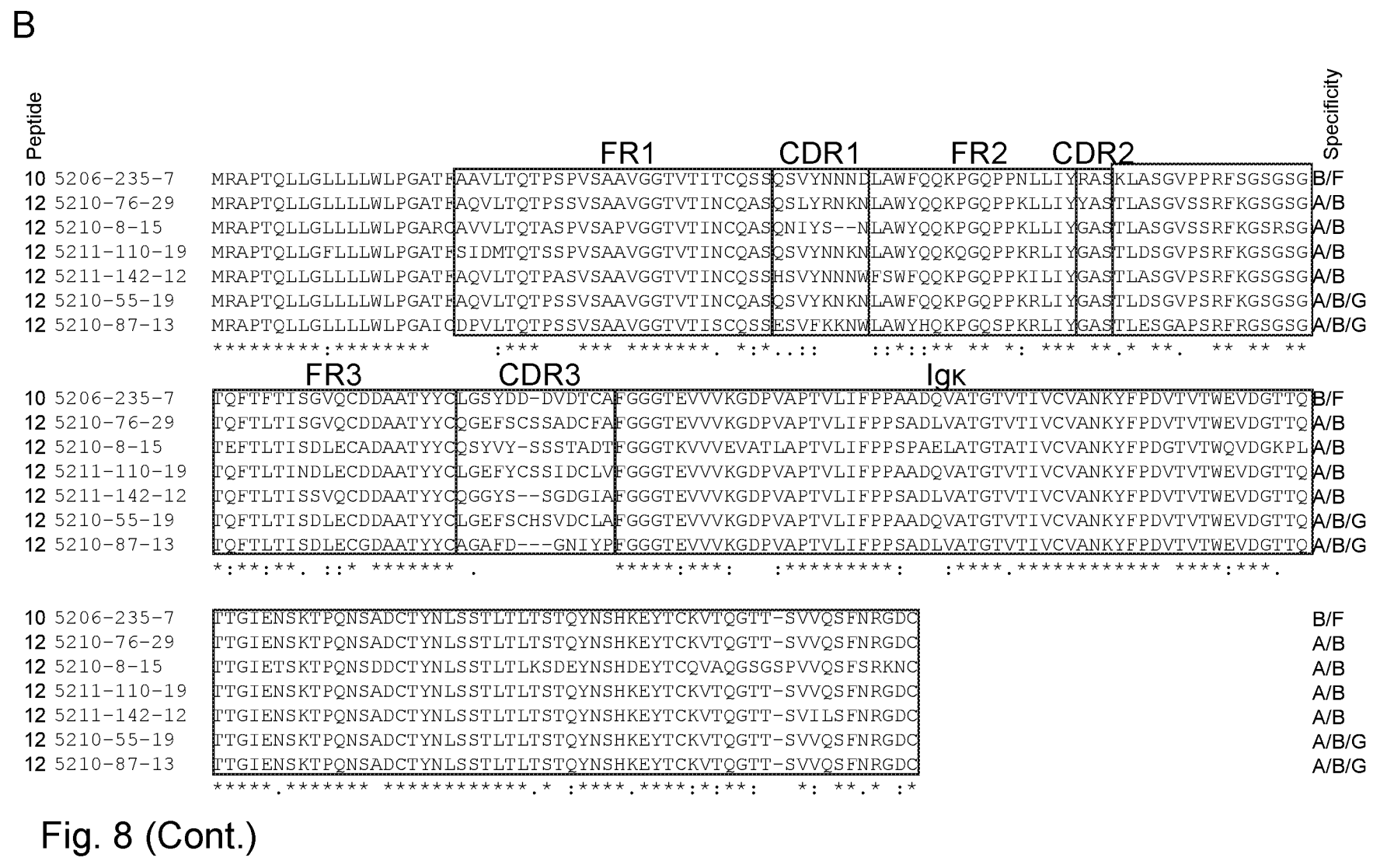
Figure 9:
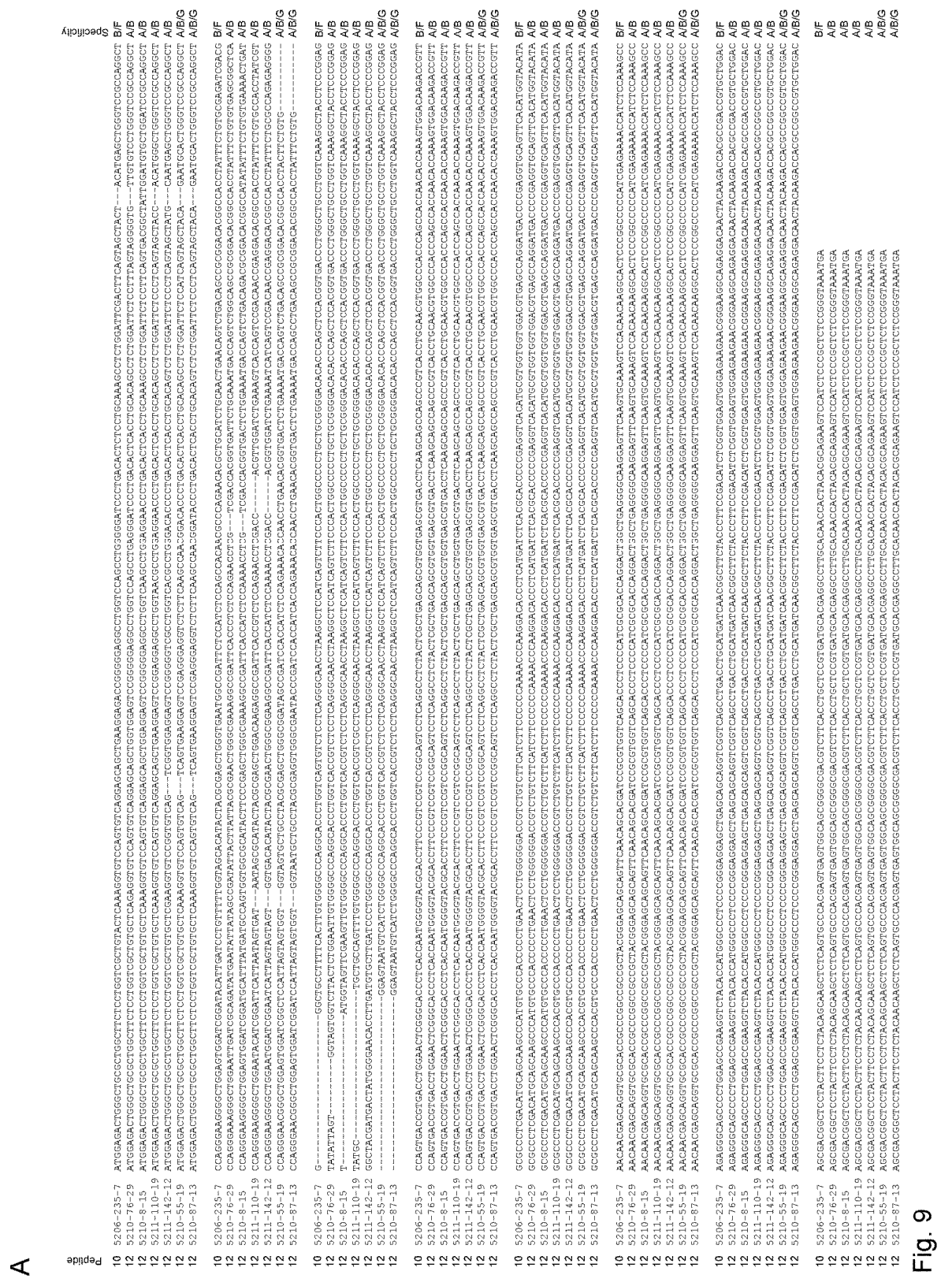
Figure 9:
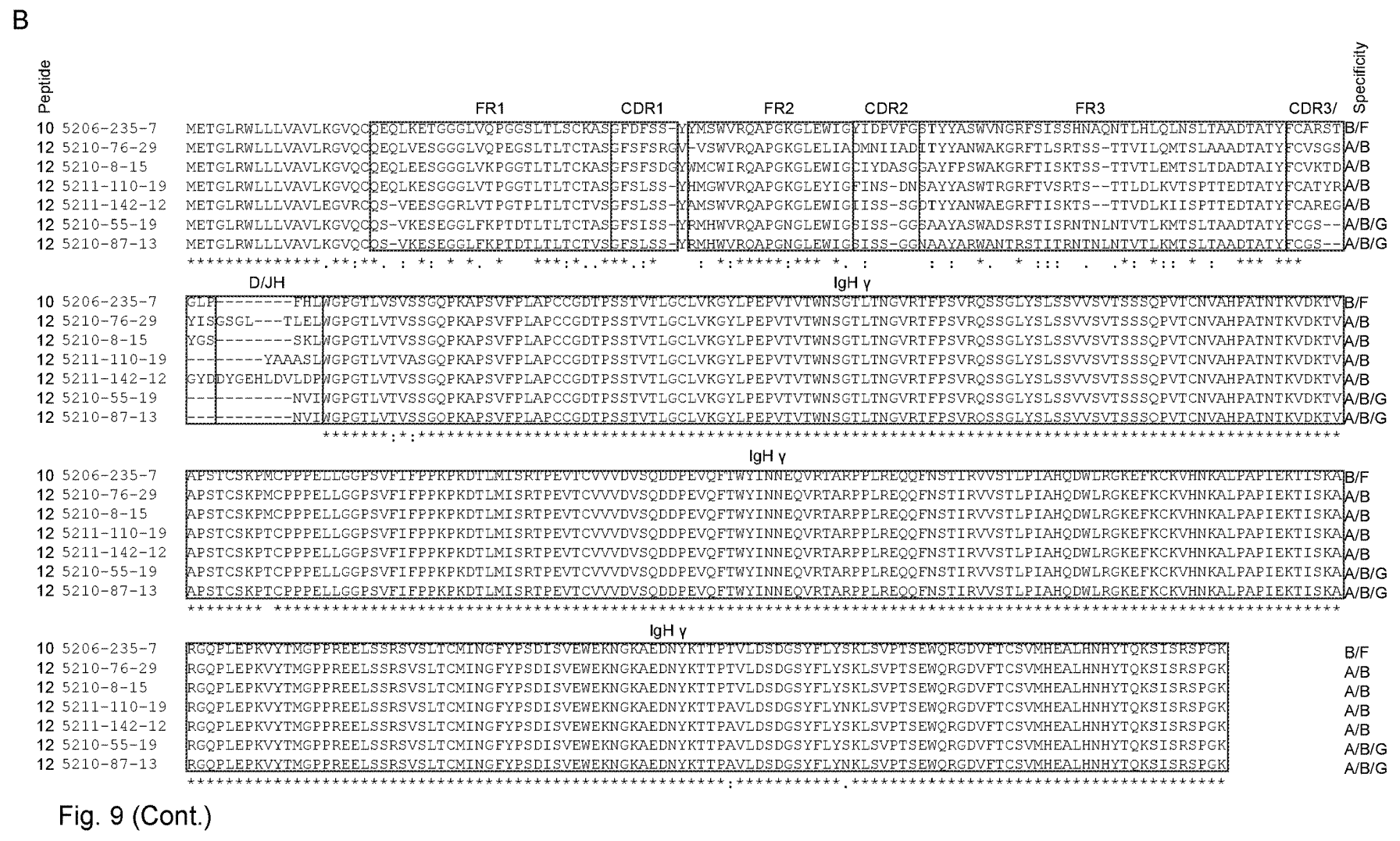

In some embodiments, the antibody includes one or more Complementarity Determining Regions (CDRs) present in the heavy and light chains of the antibodies produced by one or more of the following hybridomas: 5206-235-07, 5210-76-29, 5210-08-15, 5211-110-19, 5211-142-12, 5210-55-19, and 5210-87-13 (FIGS. 8B and 9B). The antibody may include CDRs present in the heavy and light chains of the antibodies produced by the same hybridoma and/or different hybridomas.

The antibody may include one or more CDRs present in the light chains of the antibodies produced by hybridoma cell line 5206-235-07 including, for example, the amino acid sequences QSVYNNND (SEQ ID NO:29) (CDR1), RAS (SEQ ID NO:30) (CDR2), and/or LGSYDDDVDTCA (SEQ ID NO:31) (CDR3).

The antibody may include one or more CDRs present in the light chains of the antibodies produced by hybridoma cell line 5210-76-29 including, for example, the amino acid sequences QSLYRNKN (SEQ ID NO:32) (CDR1), YAS (SEQ ID NO:33) (CDR2), and/or QGEFSCSSADCFA (SEQ ID NO:34) (CDR3).

The antibody may include one or more CDRs present in the light chains of the antibodies produced by hybridoma cell line 5210-08-15 including, for example, the amino acid sequences QNIYSN (SEQ ID NO:35) (CDR1), GAS (SEQ ID NO:36) (CDR2), and/or QSYVYSSSTADT (SEQ ID NO:37) (CDR3).

The antibody may include one or more CDRs present in the light chains of the antibodies produced by hybridoma cell line 5211-110-19 including, for example, the amino acid sequences QSVYNNKN (SEQ ID NO:38) (CDR1), GAS (SEQ ID NO:36) (CDR2), and/or LGEFYCSSIDCLV (SEQ ID NO:39) (CDR3).

The antibody may include one or more CDRs present in the light chains of the antibodies produced by hybridoma cell line 5211-142-12 including, for example, the amino acid sequences HSVYNNNW (SEQ ID NO:40) (CDR1), GAS (SEQ ID NO:36) (CDR2), and/or QGGYSSGDGIA (SEQ ID NO:41) (CDR3).

The antibody may include one or more CDRs present in the light chains of the antibodies produced by hybridoma cell line 5210-55-19 including, for example, the amino acid sequences QSVYKNKN (SEQ ID NO:42) (CDR1), GAS (SEQ ID NO:36) (CDR2), and/or LGEFSCHSVDCLA (SEQ ID NO:43) (CDR3).

The antibody may include one or more CDRs present in the light chains of the antibodies produced by hybridoma cell line 5210-87-13 including, for example, the amino acid sequences ESVFKKNW (SEQ ID NO:44) (CDR1), GAS (SEQ ID NO:36) (CDR2), and/or AGAFDGNIYP (SEQ ID NO:45) (CDR3).

The antibody may include one or more CDRs present in the heavy chains of the antibodies produced by hybridoma cell line 5206-235-07 including, for example, the amino acid sequences GFDFSS (SEQ ID NO:46) (CDR1), YIDPVFG (SEQ ID NO:47) (CDR2), and/or FCARST (SEQ ID NO:48) (CDR3).

The antibody may include one or more CDRs present in the heavy chains of the antibodies produced by hybridoma cell line 5210-76-29 including, for example, the amino acid sequences GFSFSRG (SEQ ID NO:49) (CDR1), DMNIIAD (SEQ ID NO:50) (CDR2), and/or FCVSGS (SEQ ID NO:51) (CDR3).

The antibody may include one or more CDRs present in the heavy chains of the antibodies produced by hybridoma cell line 5210-08-15 including, for example, the amino acid sequences GFSFSDG (SEQ ID NO:52) (CDR1), CIYDASG (SEQ ID NO:53) (CDR2), and/or FCVKTD (SEQ ID NO:54) (CDR3).

The antibody may include one or more CDRs present in the heavy chains of the antibodies produced by hybridoma cell line 5211-110-19 including, for example, the amino acid sequences GFSLSS (SEQ ID NO:55) (CDR1), FINSDN (SEQ ID NO:56) (CDR2), and/or FCATYR (SEQ ID NO:57) (CDR3).

The antibody may include one or more CDRs present in the heavy chains of the antibodies produced by hybridoma cell line 5211-142-12 including, for example, the amino acid sequences GFSLSS (SEQ ID NO:55) (CDR1), IISSSG (SEQ ID NO:59) (CDR2), and/or FCAREG (SEQ ID NO:60) (CDR3).

The antibody may include one or more CDRs present in the heavy chains of the antibodies produced by hybridoma cell line 5210-55-19 including, for example, the amino acid sequences GFSISS (SEQ ID NO:60) (CDR1), SISSGG (SEQ ID NO:61) (CDR2), and/or FCGS (SEQ ID NO:62) (CDR3).

The antibody may include one or more CDRs present in the heavy chains of the antibodies produced by hybridoma cell line 5210-87-13 including, for example, the amino acid sequences GFSLSS (SEQ ID NO:55) (CDR1), SISSGG (SEQ ID NO:61) (CDR2), and/or FCGS (SEQ ID NO:62) (CDR3).

Figure 3:
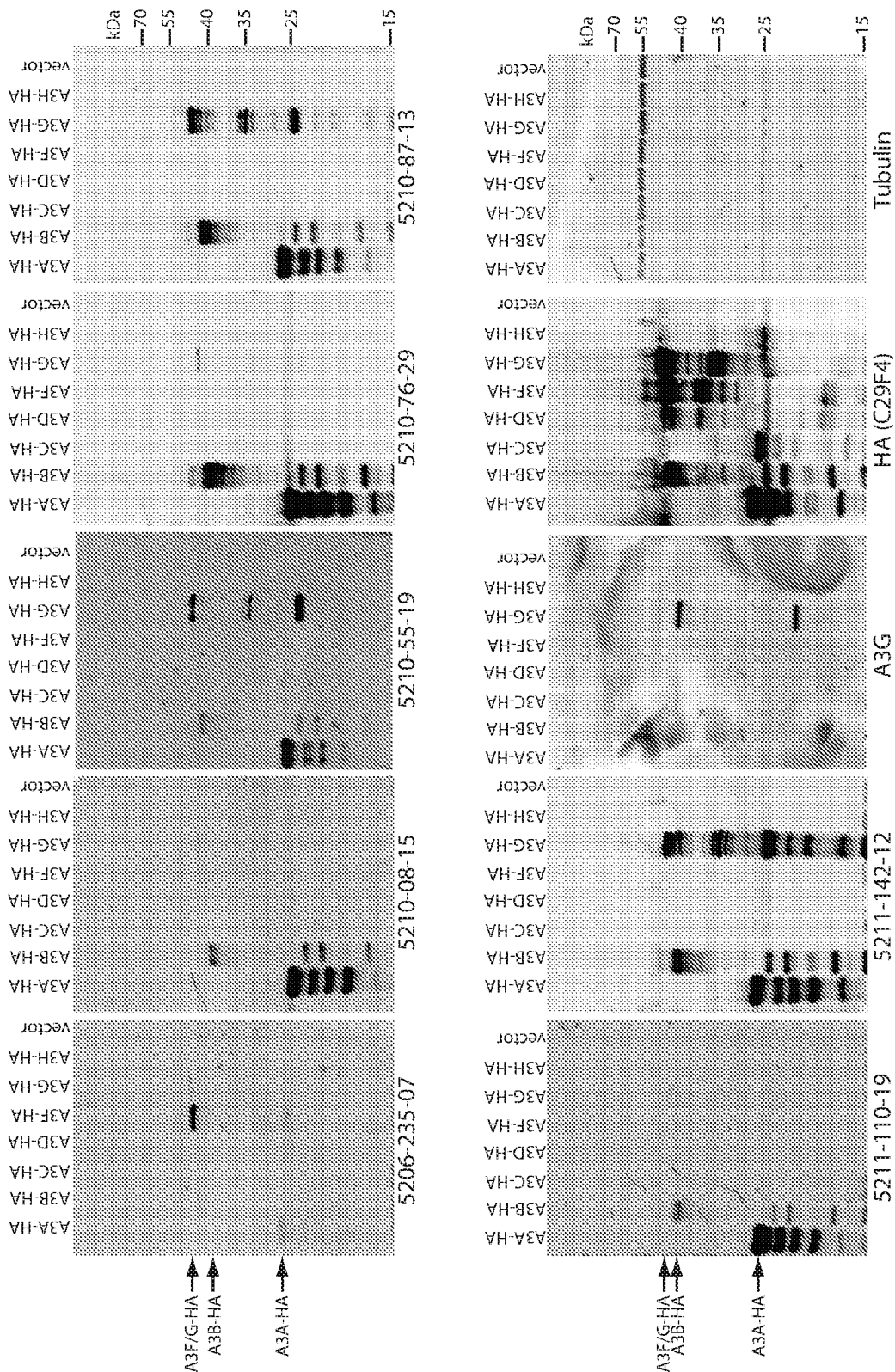
FIG. 3 shows an immunoblot of each anti-A3B monoclonal antibody against the 7-membered APOBEC3 family. Cell lysates from 293T cells transiently transfected with each HA-tagged APOBEC3 protein (A3A-HA, A3B-HA, A3C-HA, A3D-HA, A3F-HA, A3G-HA, A3H-HA) or the expression vector alone were resolved by 12% SDS-PAGE and transferred to PVDF membrane. Membranes were probed with supernatant from each hybridoma cell line (5206-235-07, 5210-08-15, 5210-55-19, 5210-76-29, 5210-87-13, 5211-110-19, and 5211-142-12) at 1/3 dilution, anti-A3G (60100, ProteinTech, Chicago, Ill.) 1/1000, anti-HA (C29F4, Rabbit mAb 3724, Cell Signaling Technology, Danvers, Mass.) 1/1000, or anti-tubulin (MMS-407R, Covance, Emeryville, Calif.) 1/20,000. Membranes were further probed with the appropriate secondary antibodies including anti-rabbit IgG IR800CW (Odyssey 926-32211, LI-COR Biosciences, Lincoln, Nebr.) 1/20,000 or anti-mouse IgG IR800CW (Odyssey 827-08364, LI-COR Biosciences, Lincoln, Nebr.) 1/20,000 in 50% Blok (WBAVDP001, Millipore, Darmstadt, Germany) in PBS-T, (PBS, 0.1% Tween-20) and images were generated using LI-COR imaging (LI-COR Biosciences, Lincoln, Nebr.).

In some embodiments, antibody that specifically binds to one family member of the APOBEC3 family will also specifically bind to other members of the APOBEC3 family, including, for example, APOBEC3A (A3A); APOBEC3B (A3B); APOBEC3C (A3C); APOBEC3D (A3D) APOBEC3F (A3F); APOBEC3G (A3G); and/or APOBEC3H (A3H) (FIG. 3). For example, antibodies from hybridoma cell line 5210-08-15, hybridoma cell line 5210-76-29, hybridoma cell line 5211-110-19, and hybridoma cell line 5211-142-12 can recognize A3A and A3B; antibodies from hybridoma cell line 5206-235-07 can recognize A3B and A3F; antibodies from hybridoma cell line 5210-55-19, and hybridoma cell line 5210-87-13 can recognize A3A, A3B, and A3G. (FIG. 3, FIG. 8B, and FIG. 9B)

Methods of Making Antibodies that Bind APOBEC3 Proteins

In one or more embodiments, epitopes specific to APOBEC3B may be used to generate antibodies that specifically bind to APOBEC3B. For example, WYKFDENYA-FLHRTLKEILRYLMD (SEQ ID NO:63), representing A3B residues 171-194 and/or PFQPWDGLEEHSQALSGRL-RAILQNQGN (SEQ ID NO:64), representing A3B residues 355-382, may be used to immunize a mammal to generate antibody-producing cells. The route and schedule of the host animal or cultured antibody-producing cells therefrom are generally in keeping with established and conventional techniques for antibody stimulation and production. The host animal may be, for example, a rabbit, mouse, or any other mammalian subject including human subjects or antibody-producing cells obtained therefrom. In some embodiments, an antigen, an epitope, or a fragment containing the target amino acid sequence may be conjugated to a protein that is immunogenic in the species to be immunized, for example, keyhole limpet hemocyanin, serum albumin, bovine thyroglobulin, ovalbumin, etc. In addition, those of skill in the art will know of various techniques common in the immunology arts for purification and concentration of polyclonal antibodies, as well as monoclonal antibodies.

The preparation of monoclonal antibodies also is well-known to those skilled in the art See, e.g., Kohler & Milstein, *Nature* 1975, 256:495; Coligan et al., sections 2.5.1-2.6.7; and Harlow et al., ANTIBODIES: A LABORATORY MANUAL, page 726 (Cold Spring Harbor Pub. 1988). Briefly, monoclonal antibodies can be obtained by injecting an animal including, for example, a mouse or a rabbit, with a composition including an antigen, verifying the presence of antibody production by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein A Sepharose, size exclusion chromatography, and ion exchange chromatography.

In some embodiments, antibodies may be produced by host cells and isolated cells. In particular embodiments, the cell is a hybridoma cell. In some additional embodiments, the hybridoma cell line is 5206-235-07, 5210-76-29, 5210-08-15, 5211-110-19, 5211-142-12, 5210-55-19, and/or 5210-87-13.

In some embodiments, antibodies may also be made by recombinant DNA methods. DNA encoding the monoclonal antibodies may be readily isolated and sequenced using conventional procedures (e.g., by using oligonucleotide probes that are capable of binding specifically to genes encoding the heavy and light chains of murine antibodies). Hybridoma cells or hybridoma cell lines may serve as a source of such DNA. Once isolated, the DNA may be placed into expression vectors, which are then transfected into host cells such as, for example, 293F cells, simian COS cells, Chinese hamster ovary (CHO) cells, myeloma cells that do not otherwise produce immunoglobulin protein, etc., to obtain the synthesis of monoclonal antibodies in the recombinant host cells. The DNA also may be modified, for example, by substituting the coding sequence for human heavy and light chain constant domains in place of homologous sequences or by covalently joining to the immunoglobulin coding sequence all or part of the coding sequence for a non-immunoglobulin polypeptide.

In some embodiments, an expression vector includes a nucleic acid sequence encoding antibody produced by hybridoma cell line 5206-235-07, hybridoma cell line 5210-76-29, hybridoma cell line 5210-08-15, hybridoma cell line 5211-110-19, hybridoma cell line 5211-142-12, hybridoma cell line 5210-55-19, and/or hybridoma cell line 5210-87-13.

An antibody fragment can be prepared by proteolytic hydrolysis of an intact antibody or by the expression of a nucleic acid encoding the fragment. An antibody fragment can be obtained by pepsin or papain digestion of an intact antibody by conventional methods. For example, an antibody fragment can be produced by enzymatic cleavage of an antibody with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. In some cases an enzymatic cleavage using pepsin can be used to produce two monovalent Fab' fragments and an Fc fragment directly.

Other methods of cleaving antibodies, such as separation of heavy chains to form monovalent light heavy chain fragments, further cleavage of fragments, or other enzymatic, chemical, or genetic techniques may also be used to provide fragments that retain some ability to bind (e.g., selectively bind) its epitope.

The antibodies provided herein can be substantially pure. The term "substantially pure" as used herein with reference to an antibody means the antibody is substantially free of other polypeptides, lipids, carbohydrates, and nucleic acids with which it is naturally associated. Thus, a substantially pure antibody is any antibody that is removed from its natural environment and is at least 60 percent pure. A substantially pure antibody can be at least about 65 percent pure, at least about 70 percent pure, at least about 75 percent pure, at least about 80 percent pure, at least about 85 percent pure, at least about 90 percent pure, at least about 95 percent pure, or at least about 99 percent pure.

Methods of Using Antibodies that Bind APOBEC3 (A3) Proteins

Antibodies that specifically bind to one or more members of the APOBEC3 (A3) family, in particular APOBEC3B, may be used in a wide variety of applications including, for example, as research reagents for molecular biology, immunology, and/or cancer biology and as clinical reagents for diagnostic and/or prognostic tests for APOBEC3B expression. Antibodies may be used for, for example, enzyme-linked immunosorbent assays (ELISA), immunoblotting (IB), immunoprecipitation (IP), immunohistochemistry (IHC), immunofluorescence (IF), and/or flow cytometry, etc.

Assays may be quantitative and/or qualitative, and may detect expression of one or more APOBEC3 (A3) family members in a variety of locations including, for example, in cells, on cell membranes, in tissues, and in bodily fluids. Assays may be used, for example, to determine normal and/or abnormal levels of protein expression.

In some embodiments, a device can include antibody that specifically binds to one or more APOBEC3 (A3) proteins. In some embodiments, the device includes immobilizing one or more antibodies that specifically bind to one or more APOBEC3 (A3) proteins to a substrate. In some embodiments, the antibody or antibodies may be immobilized on a substrate as part of an antibody microarray, antibody chip, and/or protein chip.

The present invention is illustrated by the following examples. It is to be understood that the particular examples, materials, amounts, and procedures are to be interpreted broadly in accordance with the scope and spirit of the invention as set forth herein.

EXAMPLES

Epitope Selection

The full protein sequences of the seven human APOBEC3 (A3) enzymes were obtained from GenBank: APOBEC3A (A3A) GenBank: AAI26417.1; APOBEC3B (A3B) GenBank: AAW31743.1; APOBEC3C (A3C) GenBank: AAH11739.1; APOBEC3D (A3D) GenBank: AIC57731.1; APOBEC3F (A3F) GenBank: AAZ38720.1; APOBEC3G (A3G) GenBank: AAZ38722.1; APOBEC3H (A3H) GenBank: ACK77774.1.

ClustalW was used to identify regions unique to APOBEC3B (A3B). Two regions were selected for synthesis of peptide immunogens. Peptides were synthesized by Epitomics, Inc. (Burlingame, CA). Peptide 10, WYKFDENYAFLHRTLKEILRYLMD (SEQ ID NO:63), represents A3B residues 171-194. Peptide 12, CPFQPWDGLEEHSQALSGRLRAILQNQGN (SEQ ID NO:64, with an N-terminal cysteine residue), represents A3B residues 354-382. Although unique to A3B, extensive homology between family members was unavoidable; peptide 10 shared 20/24 residues with A3F and peptide 12 shared 27/28 residues with A3A and 25/28 residues with A3G (Table 1).

TABLE 1

Homology of immunization peptides to APOBEC3 proteins

| Peptide | Length | A3A | A3B | A3C | A3D | A3F | A3G | A3H |
|---|---|---|---|---|---|---|---|---|
| Peptide 10 | <u>24</u> | 5 | <u>24</u> | 7 | 19 | 20 | 11 | 5 |
| Peptide 12 | <u>28</u> | 27 | <u>28</u> | 7 | 7 | 9 | 25 | 6 |

Immunization and Hybridoma Creation

Two rabbits were immunized with each peptide immunogen (contracted to Epitomics, Inc., Burlingame, Calif.). The rabbits were given three injections using KLH-conjugated peptide, then two further injections with OVA-conjugated peptide, over the course of 10-12 weeks. Test bleeds from the rabbits were screened for anti-A3B expression by immunoblot (TB) (Towbin et al. *Proc. Nat'l Acad. Sci. USA.* 1979; 76(9):4350-4).

Lysates from 293T cells that expressed A3-HA proteins were resolved by SDS-PAGE, transferred to PVDF membrane and immunoblotted with the test bleeds at a dilution of 1/1000 in 50% BLOK (Millipore, Darmstadt, Germany), 0.1% Tween-20 in phosphate buffered saline (PBS).

The bleeds were further screened by immunofluorescence microscopy (IF) of HeLa cells expressing A3B-GFP proteins. Hela cells were fixed in 4% paraformaldehyde (PFA), permeabilized with 0.01% Triton X-100 and then incubated in the rabbit sera (1:200) in 5% goat serum, 1% BSA, 0.2% Triton X-100 in 1×PBS. A3B binding was visualized with anti-rabbit-TRITC (1:500).

Three anti-A3B positive rabbits (5206, 5210, 5211) were selected for a final immunization boost before the spleens were harvested for B cell isolation and hybridoma production. Hybridoma fusions of 40×96-well plates with lymphocytes from the selected rabbits were performed by Epitomics, Inc. (Burlingame, Calif.). Hybridoma supernatants were screened for reactive anti-A3B antibodies by ELISA screening against recombinant A3Bctd-myc-(HIS)$_6$ purified protein (Burns et al., 2013, *Nature* 494(7437):366-370). Representative data are shown in FIG. 1. Candidate hybridomas were expanded.

Hybridoma Screening
Immunoblot

Culture media supernatants from ELISA-positive single-clone hybridomas were screened by immunoblot. Lysates from 293T cells that expressed A3-HA proteins (Hultquist et al. *J. Virol.* 2011; 85, 11220-34) were resolved by SDS-PAGE, transferred to PVDF membrane and immunoblotted with the hybridoma cell media supernatant (1:3) in 50% BLOK (Millipore, Darmstadt, Germany), 0.1% Tween 20 in PBS, detected with anti-rabbit IgG IR800CW secondary antibody (LI-COR Biosciences, Lincoln, Nebr.) and imaged by LI-COR imaging (LI-COR Biosciences, Lincoln, Nebr.). Representative data are shown in FIG. 3.

Immunofluorescence

Figure 4:
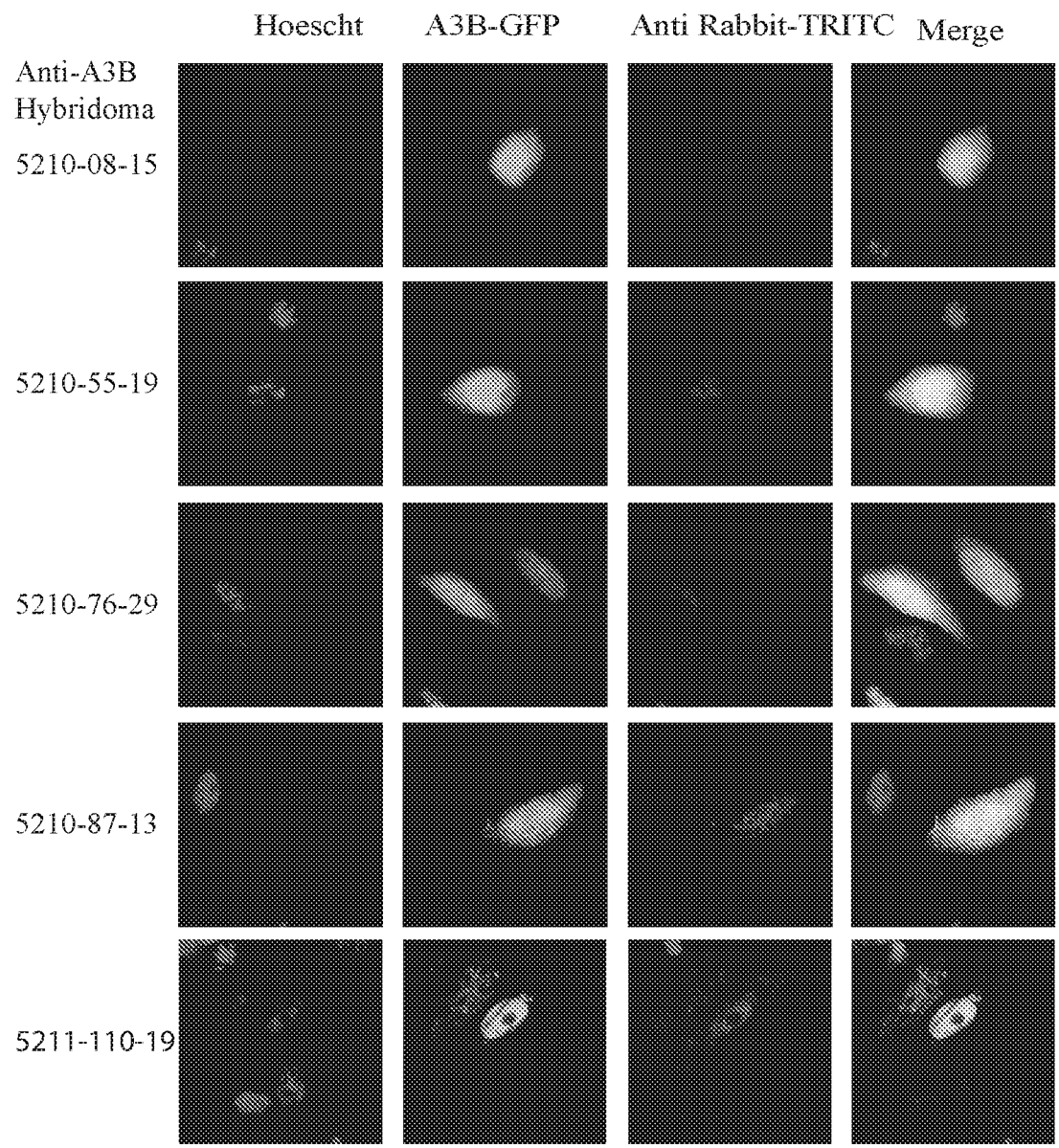
FIG. 4 shows the immunofluorescence of over-expressed A3B-GFP in HeLa cells detected by anti-A3B hybridoma supernatants. HeLa cells were plated at 250,000/well in a 6 well plate. Cells were transfected with 200 ng of A3B-GFP construct (Lackey et al. J. Mol. Bio. 2012; 419(5):301-14). 16 hours later, cells were plated at 30,000 cells/chamber in an eight-chambered slide. 24 hours post plating, cells were fixed in 4% paraformaldehyde (PFA) for 1 hour, washed, and incubated in supernatant from hybridoma cell line 5210-08-15, hybridoma cell line 5210-55-19, hybridoma cell line 5210-76-29, hybridoma cell line 5210-87-13, or hybridoma cell line 5211-110-19 overnight at room temperature. Cells were washed five times with 1×PBS and incubated in anti-rabbit-TRITC (1:500) (111095144, Jackson ImmunoResearch Laboratories Inc., West Grove, Pa.) for one hour at 37° C., then allowed to return to room temperature for two hours. Following five 1×PBS washes, nuclei were strained with Hoescht for 15 minutes at room temperature. Following two washes with 1×PBS, slides were stored submerged in 1×PBS at 4° C. Images taken at 60× magnification, with a 1 second TRITC exposure time (to normalize), cropped to 900×900 pixels and scaled down to 10% size.

Culture media supernatant from ELISA-positive single-clone hybridomas were screened by immunofluorescence microscopy. HeLa cells expressing fluorescent A3 proteins were fixed in 4% paraformaldehyde, permeabilized with 0.01% Triton X-100 and then incubated in cell media supernatant (1:5) in 5% goat serum, 1% BSA, 0.2% Triton X-100 in 1×PBS. A3B binding was visualized with anti-rabbit-TRITC (1:500). Representative data are shown in FIG. 4.

Hybridoma Expansion

Seven single-clone hybridomas expressing the strongest, most specific anti-A3B sera (5206-235-07, 5210-08-15, 5210-55-19, 5210-76-29, 5210-87-13, 5211-110-19, 5211-142-12) were identified, expanded, and stocks were frozen down.

ELISA

Figure 2:
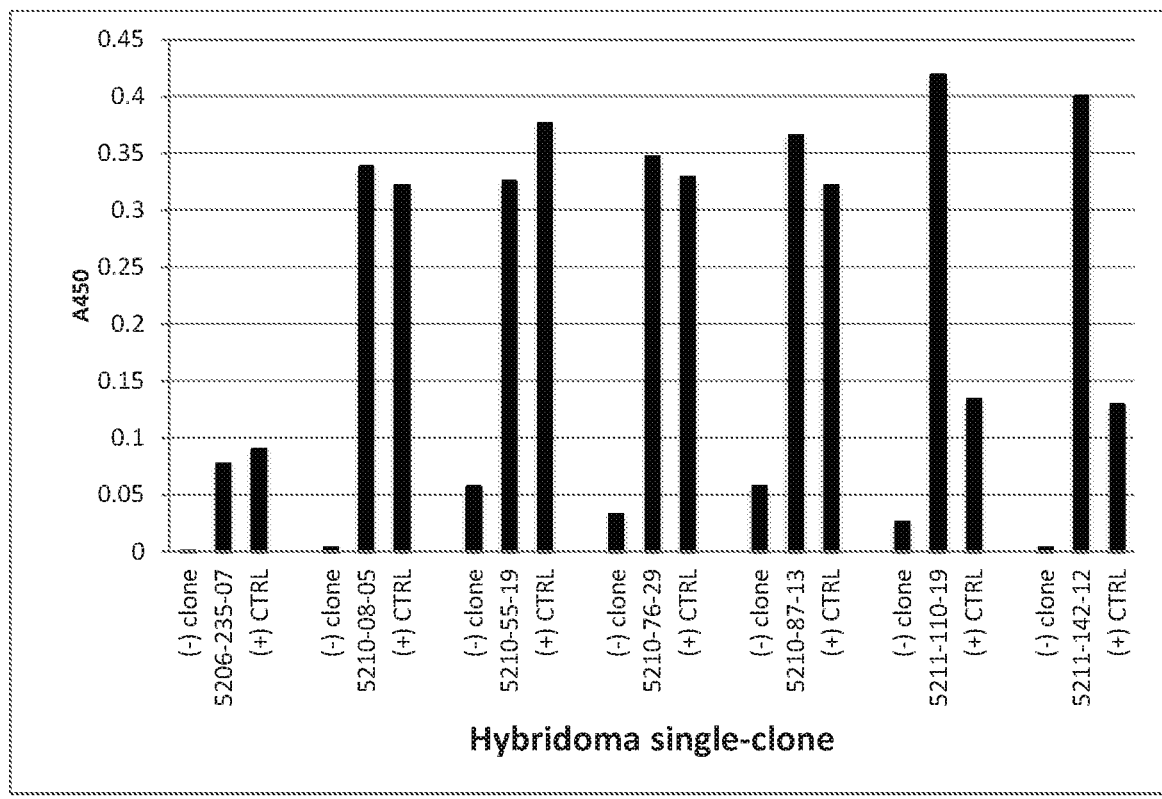
FIG. 2 shows an ELISA screen of mAb-containing supernatants from individual hybridoma clones. Cell-free supernatants from hybridoma single-clones (5206-235-07, 5210-08-15, 5210-55-19, 5210-76-29, 5210-87-13, 5211-110-19, and 5211-142-12) were assayed for binding to A3B-CTD in a standard ELISA assay. Binding was detected with an anti-rabbit HRP secondary antibody (1:5000), visualized with tetramethylbenzidine (TMB) and quantified by spectroscopy at 450 nm. The negative control in this assay was cell-free media supernatant from a hybridoma clone that did not express anti-A3B, and the positive control was a rabbit anti-A3G antibody (NIH AIDS Reagent Program 10201).

Pure hybridoma clones expressing anti-A3B mAbs were identified by ELISA screening against A3Bctd-myc-(His)$_6$ purified protein (Burns et al., 2013, *Nature* 494(7437):366-370). A3Bctd-myc-(His)$_6$ purified protein (20 ng/well) was immobilized on 96-well ELISA plates through hydrophilic and hydrophobic interactions with the polystyrene plate. Each plate was blocked with 3% BSA, then incubated with undiluted cell media supernatant from the hybridoma clones. Binding was detected with an anti-rabbit HRP secondary antibody (1:5000), visualized with tetramethylbenzidine (TMB) and quantified by spectroscopy at 450 nm. Representative data are shown in FIG. 2.

Monoclonal Antibody (mAb) Purification

Seven anti-human A3B hybridomas were expanded to 1 L, then switched to serum-free media for one week. The media was clarified by centrifugation to remove the cells before it was passed over a Protein A to bind IgG (Boca Scientific Inc., Boca Raton, Fla.) (Wilchek et al. *Methods Enzymol.* 1984; 104:3-55). The monoclonal antibodies were eluted in 0.2 M glycine pH 2.5 and dialyzed into PBS and stored frozen in BSA (0.1 mg/mL) with azide (0.02%).

Immunoblots of Endogenous A3B in Cancer Cell Lines

Figure 5:
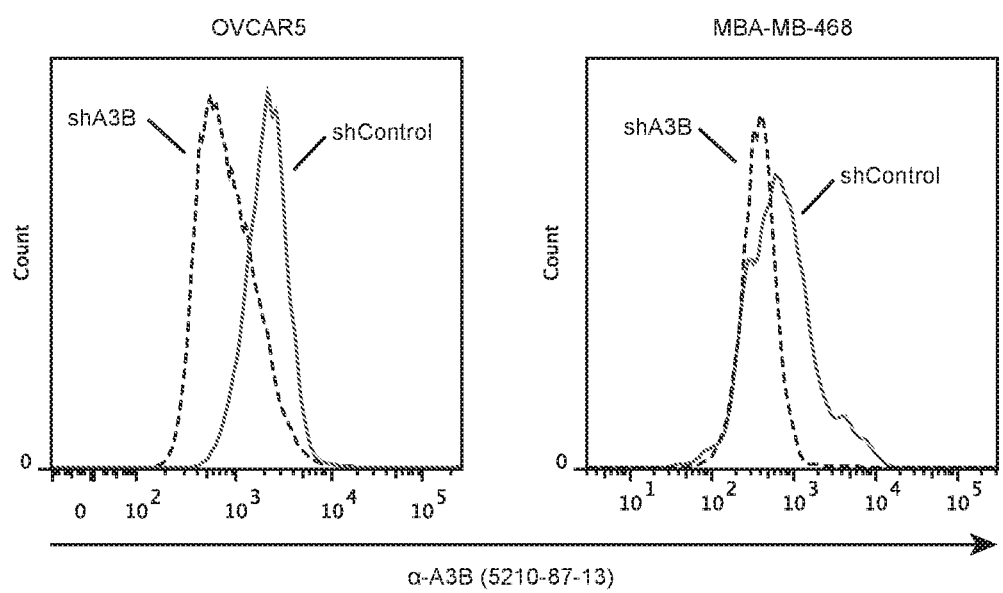
FIG. 5 shows intracellular staining of endogenous A3B in two cancer cell lines by flow cytometry (FLOW). OVCAR5 (Monks et al., 1991, J. Natl. Cancer Inst. 83:757-766) and MDA-MB-468 (ATCC HTB-132, ATCC, Manassas, Va.) cells were transduced with lentiviruses encoding either a control or A3B-specific shRNA. Following drug selection (puromycin), cells were fixed in 1% paraformaldehyde and permeabilized in cold methanol. Cells were then incubated with rabbit anti-A3B 5210-87-13 for one hour at room temperature, followed by an anti-rabbit PE-conjugated secondary antibody for 20 minutes at room temperature in the dark. After a single PBS wash to remove unbound antibody, cells were analyzed on a flow cytometer. Cells with endogenous A3B depleted by shRNA have significantly lower average fluorescence intensity.
Figure 6:
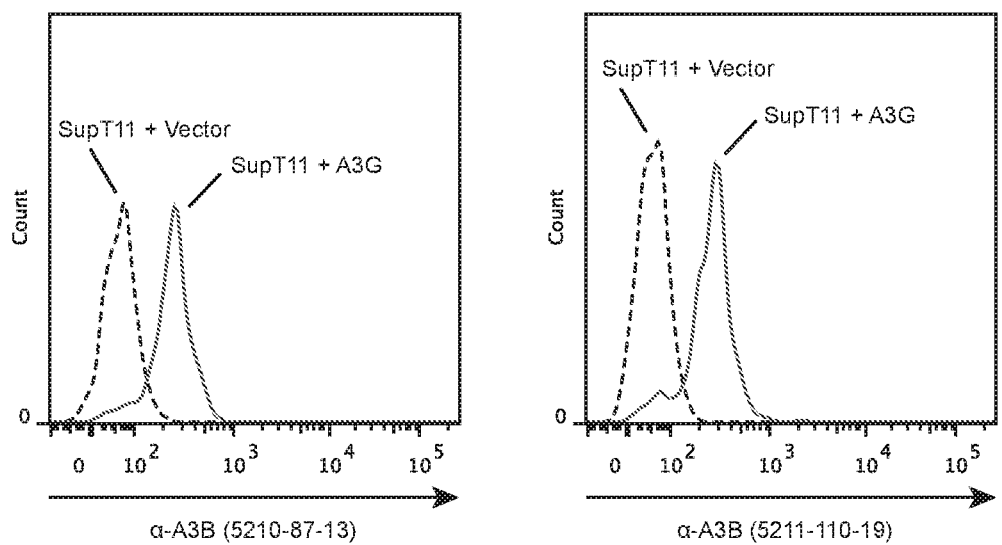
FIG. 6 shows intracellular staining of exogenous (transfected) A3G in a cancer cell line by flow cytometry (FLOW). The SupT11 cell line was stably transfected with pcDNA3.1 (SupT11+Vector) or pcDNA3.1 A3G-HA (SupT11+A3G-HA). Cells were fixed in 1% paraformaldehyde and permeabilized in cold methanol. Cells were then incubated with rabbit anti-A3B 5210-87-13 or rabbit anti-5211-10-19 for one hour at room temperature, followed by an anti-Rabbit FITC-conjugated secondary antibody for 20 minutes at room temperature in the dark. Cells were analyzed on a cytometer.
Figure 7:
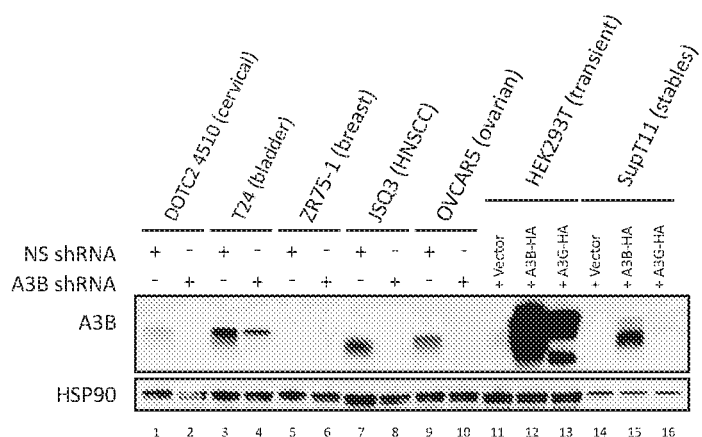
FIG. 7 shows detection of endogenous A3B in various cancer cell lines treated with A3B shRNA or control shRNA (Burns et al., 2013, Nature 494(7437):366-370). (A) Lysates from various cancer cell lines (cervical (DOTC2 4510, ATCC CRL-7920, ATCC, Manassas, Va.), bladder (T24, ATCC HTB-4, ATCC, Manassas, Va.), breast (ZR-75-1, ATCC CRL-1500, ATCC, Manassas, Va.), head and neck squamous cell carcinoma (JSQ3, Weichselbaum et al., 1988, Int. J. Radiat. Oncol. Biol. Phys. 15:575-579), and ovarian (OVCAR5, Monks et al., 1991, J. Natl. Cancer Inst. 83:757-766)) were resolved by SDS-PAGE, transferred to PVDF membrane, immunoblotted with anti-human A3B mAb (5210-87-13) (1:50) in 5% milk, 0.1% Tween 20 in PBS, and detected with anti-rabbit HRP secondary antibody. (B) Osteosarcoma (U-2 OS, ATCC HTB-96, ATCC, Manassas, Va.) cells were transduced with shControl or shA3B constructs (Burns et al., 2013, Nature 494(7437):366-370) and plated at 20,000 cells/chamber in eight-chamber slides. 24 hours after plating, cells were fixed in 4% PFA for 30 minutes. Slides were incubated in primary antibody (5210-87-13, diluted 1:5) overnight at room temperature. Following five washes with 1×PBS, cells were incubated at 37° C. for one hour in anti-rabbit (anti-Rb) TRITC (1:500) then cooled to room temperature for two hours. Following five washes with 1×PBS, nuclei were stained with Hoescht dye for 15 minutes. Dye was removed and cells were stored at 4° C. submerged in 1×PBS. Images were taken at 60× magnification, cropped to 900×900 pixels and scaled down to 10% size.
Figure 7:
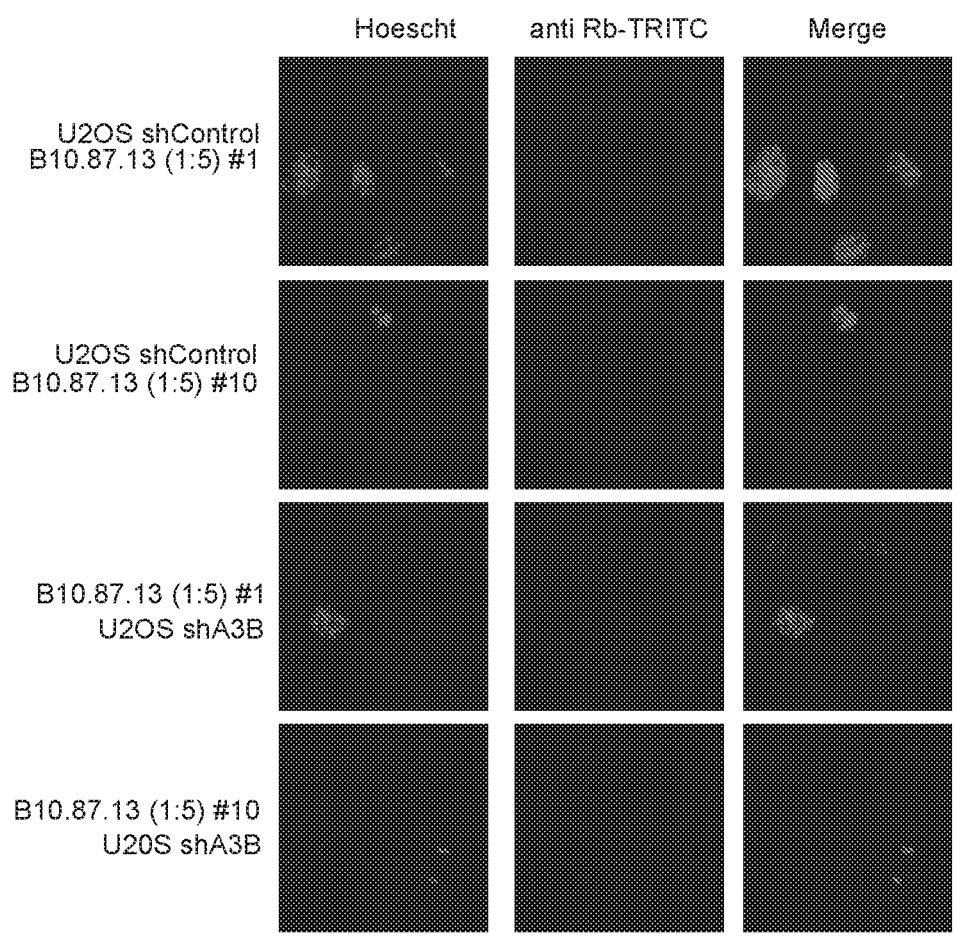

Anti-human A3B 5210-87-13 was immunoblotted against various human cancer cell lines that express A3B. Lysates from various cancer cell lines were resolved by SDS-PAGE, transferred to PVDF membrane and immunoblotted with anti-human A3B mAb (5210-87-13) (1:50) in 5% milk, 0.1% Tween 20 in PBS, detected with anti-rabbit HRP secondary antibody. Expression of A3B was reduced or eliminated when the cells had been treated with A3B shRNA (Burns et al., 2013, *Nature* 494(7437):366-370) to knockdown A3B expression, as shown in FIG. 5A, demonstrating the specificity of this mAb.

Immunofluorescent Microscopy of Endogenous A3B

Using the anti-human A3B mAb (5210-87-13) endogenous A3B was detected. U2OS cells were fixed in 4% paraformaldehyde, permeabilized with 0.01% Triton X-100 and then incubated in anti-human A3B mAb (5210-87-13) in 5% goat serum, 1% BSA, 0.2% Triton X-100 in 1×PBS. A3B binding was visualized with anti-rabbit-TRITC (1:500). Expression of A3B was reduced or eliminated when the cells had been treated with A3B shRNA to knockdown A3B expression as shown in FIG. 5B.

Heavy and Light Chain Sequencing

Rabbit Hybridoma lines derived from the 240E-W fusion partner express variable amounts of an endogenous Ig heavy chain (U.S. Pat. No. 7,429,487). This competes with the Ig heavy chain selected from the B lymphocyte for the Ig light chain, resulting in reduced titers and affinity of the desired mAb. To improve the efficacy of these anti-human A3B mAbs Ig heavy and light chain genes were sequenced as follows.

RNA Purification

Hybridoma cells (1×10$^7$ cells) were sheared by centrifugation through RNeasy columns (Qiagen N.V., Hilden, Germany) and RNA was purified using RNeasy columns (Qiagen N.V., Hilden, Germany).

cDNA Sequencing of the Ig Light Chain and the Constant Region of Heavy Chain Genes RNA purified from the rabbit hybridomas was used as a template for reverse transcription, primed from oligo-dT (3' RACE Adapter GCGAGCACAGAATTAATACGACT-CACTATAGGTTTTTTTTTTTTVN (SEQ ID NO:66)), to synthesize cDNA. The constant region of the rabbit immunoglobulin (Ig) heavy and light chain genes was amplified by polymerase chain reaction (PCR) using 5' primers to the rabbit Ig heavy or light chain gene constant regions (Hc constant 5' outer primer ATCAGTCTTCCCACTGGCC (SEQ ID NO:67), Hc constant 5' inner primer GGGACA-CACCCAGCTCC (SEQ ID NO:68), Ig Lc 5' outer primer CATGAGGGCCCCCACT (SEQ ID NO:69), Ig Lc 5' inner primer TCCTGCTGCTCTGGCTC (SEQ ID NO:70)) and a 3' RACE primer (3' RACE outer primer GCGAGCACA-GAATTAATACGACT (SEQ ID NO:71), 3' RACE inner primer CGCGGATCCGAATTAATACGACTCACTATAGG (SEQ ID NO:72)). The DNA product was ligated into pJET1.2/blunt vector (CloneJET PCR Cloning Kit, Thermo Fisher Scientific, Inc., Waltham, Mass.) and sequenced. The DNA and protein sequences of the light chain genes are shown in FIG. 8A and FIG. 8B. See Table 2 for an aggregate list of primer sequences.

Ch outer (rev) CCGGGAGGTAGCCTTTGACC (SEQ ID NO:78), Ig Ch inner (rev) GAGGGTGCCCGAGTTCCAG (SEQ ID NO:79), IgHc 3'-Jh3/5 Rev CRGTGACCAGGGT-GCCCTG (SEQ ID NO:80), IgHc 5'-Jh3/5 Rev CCCCA-

TABLE 2

Aggregate list of DNA primers.
Oligonucleotide primers used in PCR reactions to clone Ig cDNAs from rabbit hybridomas.

| Description | Number | Sequence | |
|---|---|---|---|
| 3' RACE Adapter | RSH7898 | GCGAGCACAGAATTAATACGACTCACTATAGGTTTTTTTTTTTVN | SEQ ID NO: 66 |
| 3' RACE outer primer | RSH9123 | GCGAGCACAGAATTAATACGACT | SEQ ID NO: 71 |
| 3' RACE inner primer | RSH9124 | CGCGGATCCGAATTAATACGACTCACTATAGG | SEQ ID NO: 72 |
| Ig Lc 5' outer | RSH8352 | CATGAGGGCCCCCACT | SEQ ID NO: 69 |
| Ig Lc 5' inner | RSH8353 | TCCTGCTGCTCTGGCTC | SEQ ID NO: 70 |
| Hc constant 5' outer | RSH8348 | ATCAGTCTTCCCACTGGCC | SEQ ID NO: 67 |
| Hc constant 5' inner | RSH8360 | GGGACACACCCAGCTCC | SEQ ID NO: 68 |
| RLM-RACE 5' RACE adaptor | RSH8512 | GCUGAUGGCGAUGAAUGAACACUGCGUUUGCUGGCUUUGAUGAAA | SEQ ID NO: 73 |
| 5' RACE outer primer | RSH9121 | GCTGATGGCGATGAATGAACACTG | SEQ ID NO: 74 |
| 5' RACE inner primer | RSH9122 | CGCGGATCCGAACACTGCGTTTGCTGGCTTTGATG | SEQ ID NO: 75 |
| Ig Hc 5' outer Rev | RSH8359 | GGCCAGTGGGAAGACTGAT | SEQ ID NO: 76 |
| Ig Hc 5' inner Rev | RSH8361 | GGAGCTGGGTGTGTCCC | SEQ ID NO: 77 |
| Ig Ch outer (rev) | RSH9011 | CCGGGAGGTAGCCTTTGACC | SEQ ID NO: 78 |
| Ig Ch inner (rev) | RSH9012 | GAGGGTGCCCGAGTTCCAG | SEQ ID NO: 79 |
| IgHc 3'-Jh3/5 Rev | RSH9046 | CRGTGACCAGGGTGCCCTG | SEQ ID NO: 80 |
| IgHc 5'-Hd3/5 Rev | RSH9045 | CCCCAGRGATCCAACCRRTC | SEQ ID NO: 81 |
| Kpn-5' Ig Kc | RSH8356 | gaggtaccATG GAC ATG AGG GCC CC | SEQ ID NO: 82 |
| Xho-3' Ig Kc | RSH8357 | AGAGCTTCAATAGGGGTGACTGTTAGctcgagacgc | SEQ ID NO: 83 |
| 5'-Nhe1 Ig Vh | RSH9119 | CAGgctagcaccATGGAGACTGGGCTGCGC | SEQ ID NO: 84 |
| 3'-Mlu1 Ig Hc | RSH8986 | tagacgcgtTCAtttaCCCGGAGAGCGGGAG | SEQ ID NO: 85 | cDNA Sequencing of the Variable Region of Heavy Chain Ig Genes

5' RLM-RACE was carried out using the FIRSTCHOICE RLM-RACE Kit (Ambion, Invitrogen Corp., Carlsbad, Calif.) (Maruyama et al. Gene. 1994; 138(1-2):171-4). RNA was treated with Calf Intestinal Phosphatase to remove phosphate molecules from degraded mRNA. Next, Tobacco Acid Phosphatase treatment removed the cap from full-length mRNA. Then the 5'RACE adaptor (RLM-RACE 5' RACE adaptor GCUGAUGGCGAUGAAUGAACACUG-CGUUUGCUGGCUUUGAUGAAA (SEQ ID NO:73)) was ligated onto the mRNA. Reverse transcription was carried out, primed from random hexamers, to synthesized cDNA. The variable region of the rabbit Ig heavy chain genes was amplified by two rounds of PCR, using 5' nested primers to the 5' RACE adaptor (5' RACE outer primer GCTGATG-GCGATGAATGAACACTG (SEQ ID NO:74), 5' RACE inner primer CGCGGATCCGAACACTGCGTTTGCTG-GCTTTGATG (SEQ ID NO:75)), and 3' nested primers to rabbit Ig heavy chain constant region (Ig Hc 5' outer Rev GGCCAGTGGGAAGACTGAT (SEQ ID NO:76), Ig Hc 5' inner Rev GGAGCTGGGTGTGTCCC (SEQ ID NO:77), Ig GRGATCCAACCRRTC (SEQ ID NO:81)). The DNA product was cloned into pJET1.2/blunt vector (CloneJET PCR Cloning Kit, Thermo Fisher Scientific, Inc., Waltham, Mass.) and sequenced. The DNA and protein sequences of the heavy chain genes are shown in FIG. 9A and FIG. 9B. See Table 2 for an aggregate list of primer sequences.

Heavy and Light Chain Subcloning

The rabbit hybridoma heavy and light chain Ig genes were amplified by PCR from pJET1.2 using gene-specific primers (Kpn-5' Ig Lc gaggtaccATG GAC ATG AGG GCC CC (SEQ ID NO:82), Xho-3' Ig Lc AGAGCTTCAATAGGGGT-GACTGTTAGctcgagacgc (SEQ ID NO:83), 5'-Nhe1 Ig Hc CAGgctagcaccATGGAGACTGGGCTGCGC (SEQ ID NO:84), 3'-Mlu1 Ig Hc tagacgcgtTCAtttaCCCGGA-GAGCGGGAG (SEQ ID NO:85)) and sub-cloned into the pcDNA3.1+eukaryotic expression vector (Life Technologies, Thermo Fisher Scientific, Inc., Waltham, Mass.). See Table 2 for an aggregate list of primer sequences.

Protocols to Express High-Titer Rabbit Anti-Human A3B mAbs

The heavy and light chain Ig genes, for rabbit hybridomas 5210-87-13 and 5211-110-19, were transfected into 293F cells (Life Technologies, Thermo Fisher Scientific, Inc., Waltham, Mass.) using polyethyleneimine (PEI) at a ratio of 3:1, PEI:DNA, in serum-free Freestyle media (Life Technologies, Thermo Fisher Scientific, Inc., Waltham, Mass.).

150 mL of culture media was collected, and monoclonal antibodies were purified by Protein A affinity chromatography (Boca Scientific Inc., Boca Raton, Fla.). The monoclonal antibodies were eluted in 0.2 M glycine pH 2.5 and dialyzed into PBS and stored frozen in BSA (0.1 mg/mL) with azide (0.02%). Monoclonal antibody 5210-87-13 concentration 13 µg/mL, 5211-110-19 36 µg/mL.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A monoclonal antibody that specifically binds to one or more APOBEC3 (A3) proteins, the monoclonal antibody comprising:
   a heavy chain comprising SEQ ID NO:44, SEQ ID NO:36, and SEQ ID NO:45; and
   a light chain comprising SEQ ID NO:55, SEQ ID NO:61, and SEQ ID NO:62.

2. The monoclonal antibody produced by hybridoma cell line 5210-87-13.

3. The monoclonal antibody of claim 1 comprising SEQ ID NO:14.

4. The monoclonal antibody of claim 1 comprising SEQ ID NO:28.

5. A method for detecting the expression of one or more APOBEC3 (A3) proteins by a subject, the method comprising:
   obtaining a biological sample from the subject;
   contacting at least a portion of the sample with the monoclonal antibody of claim 1 under conditions effective to allow the monoclonal antibody to bind to any APOBEC3 proteins in the biological sample;
   removing unbound monoclonal antibody; and
   detecting monoclonal antibody bound to an APOBEC3 protein.

6. The method of claim 5, wherein the APOBEC3 protein is APOBEC3B (A3B).

7. The method of claim 5, wherein detecting monoclonal antibody bound to an APOBEC3 protein comprises performing at least one of: enzyme-linked immunosorbent assays (ELISA), immunoblotting (IB), immunoprecipitation (IP), immunohistochemistry (IHC), immunofluorescent microscopy (IF), and flow cytometry (FLOW).

8. A device comprising the monoclonal antibody of claim 1 immobilized to a substrate.

9. A vector expressing a nucleic acid sequence encoding antibody produced by at least one of hybridoma cell line 5206-235-07, hybridoma cell line 5210-76-29, hybridoma cell line 5210-08-15, hybridoma cell line 5211-110-19, hybridoma cell line 5211-142-12, hybridoma cell line 5210-55-19, and hybridoma cell line 5210-87-13.

* * * * *

SEQUENCE LISTING

```
<160> NUMBER OF SEQ ID NOS: 84

<210> SEQ ID NO 1
<211> LENGTH: 711
<212> TYPE: DNA
<213> ORGANISM: Artificial
<220> FEATURE:
<223> OTHER INFORMATION: hybridoma

<400> SEQUENCE: 1
atgagggccc ccactcagct gctggggctc ctgctgctct ggctcccagg tgccacattt      60
gcagccgtgc tgacccagac accatcaccc gtgtctgcag ctgtgggagg cacagtcacc     120
atcacttgcc agtccagtca gagtgtttat aataataacg acttagcctg gtttcagcag     180
aaaccagggc agcctcctaa cctcctgatc tacagggcat ccaaactggc atctggggtc     240
ccaccacggt tcagcggcag tggatctggg acacagttca ctttcaccat tagcggcgtg     300
cagtgtgacg atgctgccac ttactactgt ctcggcagtt atgatgatga tgttgatact     360
tgtgctttcg gcggagggac cgaggtggtg gtcaaaggtg atccagttgc acctactgtc     420
ctcatcttcc caccagctgc tgatcaggtg gcaactggaa cagtcaccat cgtgtgtgtg     480
gcgaataaat actttcccga tgtcaccgtc acctgggagg tggatggcac cacccaaaca     540
actggcatcg agaacagtaa aacaccgcag aattctgcag attgtaccta caacctcagc     600
agcactctga cactgaccag cacacagtac aacagccaca agagtacac ctgcaaggtg      660 acccagggca cgacctcagt cgtccagagc ttcaataggg gtgactgtta g              711

<210> SEQ ID NO 2
<211> LENGTH: 714
<212> TYPE: DNA
<213> ORGANISM: Artificial
<220> FEATURE:
<223> OTHER INFORMATION: hybridoma

<400> SEQUENCE: 2
```

```
atgagggccc ccactcagct gctggggctc ctgctgctct ggctcccagg tgccacattt    60
gcccaagtgc tgacccagac tccatcctcc gtgtctgcag ctgtgggagg cacagtcacc   120
atcaactgcc aggccagtca gagtctttat aggaacaaaa atttagcctg gtatcaacag   180
aaaccagggc agcctcccaa actcctgatc tattatgcat ccactctggc atctggggtc   240
tcatcgcggt tcaaaggcag tggatctggg acacagttca ctctcaccat cagcggcgtg   300
cagtgtgacg atgctgccac ttactactgt caaggcgaat ttagttgtag tagtgctgat   360
tgttttgctt tcggcggagg gaccgaggtg gtcgtcaaag gtgatccagt tgcacctact   420
gtcctcatct tcccaccatc tgctgatctt gtggcaactg gaacagtcac catcgtgtgt   480
gtggcgaata atactttccc gatgtcacc  gtcacctggg aggtggatgg caccacccaa   540
acaactggca tcgagaacag taaaacaccg cagaattctg cagattgtac ctacaacctc   600
agcagcactc tgacactgac cagcacacag tacaacagcc acaaagagta cacctgcaag   660
gtgacccagg gcacgacctc agtcgtccag agcttcaata ggggtgactg ttag         714

<210> SEQ ID NO 3
<211> LENGTH: 708
<212> TYPE: DNA
<213> ORGANISM: Artificial
<220> FEATURE:
<223> OTHER INFORMATION: hybridoma

<400> SEQUENCE: 3
atgagggccc ccactcagct gctggggctc ctgctgctct ggctcccagg tgccagatgt    60
gccgtcgtgc tgacccagac tgcatccccc gtgtctgcac ctgtgggagg cacagtcacc   120
atcaattgcc aggccagtca gaacatttac agcaatttag cctggtatca gcagaaacca   180
gggcagcctc ccaagctcct gatctatggt gcatccactc tggcatctgg ggtctcatcg   240
cggttcaaag gcagtagatc tgggacagag ttcactctca ccatcagcga cctggagtgt   300
gccgatgctg ccacttatta ttgtcaaagc tatgtttata gtagtagtac tgctgatact   360
ttcggcggag ggaccaaggt ggtcgtcgaa gttgctacat ggcacctac tgtcctcatc    420 ttcccaccat ctcctgctga gctggcaact ggaacagcca ccatcgtgtg cgtggcaaac   480
aaatactttc ccgatggcac cgtcacctgg caggtggatg gcaagcccct aacaactggc   540
atcgagacca gtaaaacacc gcagaattct gatgattgta cctacaacct cagcagtact   600
ctgacactga aaagcgacga gtacaacagc cacgacgagt acacctgcca ggtggcccag   660
ggctcaggct caccggtcgt ccagagcttc agtaggaaga actgttag                708

<210> SEQ ID NO 4
<211> LENGTH: 714
<212> TYPE: DNA
<213> ORGANISM: Artificial
<220> FEATURE:
<223> OTHER INFORMATION: hybridoma

<400> SEQUENCE: 4
atgagggccc ccactcagct gctgggattc ctgctgctct ggctcccagg tgccacattt    60
tccatcgata tgacccagac ttcatcccct gtgtctgcag ctgtgggagg cacagtcacc   120
atcaactgcc aggccagtca gagtgtttat aataacaaaa atttagcctg gtatcagcag   180
aaacaagggc agcctcccaa acgcctaatc tatggtgcgt ccactctgga ttctggggtc   240
ccatcgcggt tcaaaggcag tggatctggg acacagttca ctctcaccat caacgacctg   300
gaatgtgacg atgctgccac ttactactgc ctaggcgaat tttattgtag cagtattgat   360
```

| | |
|---|---|
| tgtcttgttt tcggcggagg gaccgaggtg gtggtcaaag gtgatccagt tgcacctact | 420 |
| gtcctcatct tcccaccagc tgctgatcag gtggcaactg aacagtcac catcgtgtgt | 480 |
| gtggcgaata atactttcc cgatgtcacc gtcacctggg aggtggatgg caccacccaa | 540 |
| acaactggca tcgagaacag taaaacaccg cagaattctg cagattgtac ctacaacctc | 600 |
| agcagcactc tgacactgac cagcacacag tacaacagcc acaaagagta cacctgcaag | 660 |
| gtgacccagg gcacgacctc agtcatcttg agcttcaata ggggtgactg ttag | 714 |

<210> SEQ ID NO 5
<211> LENGTH: 708
<212> TYPE: DNA
<213> ORGANISM: Artificial
<220> FEATURE:
<223> OTHER INFORMATION: hybridoma

<400> SEQUENCE: 5

| | |
|---|---|
| atgagggccc ccactcagct gctggggctc ctgctgctct ggctcccagg tgccacattt | 60 |
| gcccaagtgc tgacccagac tccagcctcc gtgtctgcag ctgtgggagg cacagtcacc | 120 |
| atcaattgcc agtccagtca cagcgtttat aataacaatt ggttttcctg gtttcagcag | 180 |
| aaaccagggc agcctcccaa aatcctgatc tatggtgcat ccactctggc atctggggtc | 240 |
| ccatcgcggt tcaaaggcag tggatctggg acacagttca ctctcaccat cagcagcgtg | 300 |
| cagtgtgacg atgctgccac ttactactgt caaggcggtt atagtagtgg tgatggtata | 360 |
| gctttcggcg agggaccga ggtggtcgtc aaaggtgatc cagttgcacc tactgtcctc | 420 |
| atcttcccac catctgctga tcttgtggca actggaacag tcaccatcgt gtgtgtggcg | 480 |
| aataaatact ttcccgatgt caccgtcacc tgggaggtgg atggcaccac ccaaacaact | 540 |
| ggcatcgaga acagtaaaac accgcagaat tctgcagatt gtacctacaa cctcagcagc | 600 |
| actctgacac tgaccagcac acagtacaac agccacaaag agtacacctg caaggtgacc | 660 |
| cagggcacga cctcagtcgt ccagagcttc aatagggggtg actgttag | 708 |

<210> SEQ ID NO 6
<211> LENGTH: 714
<212> TYPE: DNA
<213> ORGANISM: Artificial
<220> FEATURE:
<223> OTHER INFORMATION: hybridoma

<400> SEQUENCE: 6

| | |
|---|---|
| atgagggccc ccactcagct gctggggctc ctgctgctct ggctcccagg tgccacattt | 60 |
| gcccaagtgc tgacccagac tccatcctcc gtgtctgcag ctgtgggagg cacagtcacc | 120 |
| atcaattgcc aggccagtca gagtgtttat aagaacaaaa atttagcctg gtttcagcag | 180 |
| aaaccagggc agcctcccaa acgcctaatc tatggtgcgt ccactctgga ttctggggtc | 240 |
| ccatcgcggt tcaaaggcag tggatctggg acacagttca ctctcaccat cagcgacctg | 300 |
| gagtgtgacg atgctgccac ttactactgc ctaggcgaat ttagttgtca tagtgttgat | 360 |
| tgtcttgctt tcggcggagg gaccgaggtg gtggtcaaag gtgatccagt tgcacctact | 420 |
| gtcctcatct tcccaccagc tgctgatcag gtggcaactg aacagtcac catcgtgtgt | 480 |
| gtggcgaata atactttcc cgatgtcacc gtcacctggg aggtggatgg caccacccaa | 540 |
| acaactggca tcgagaacag taaaacaccg cagaattctg cagattgtac ctacaacctc | 600 |
| agcagcactc tgacactgac cagcacacag tacaacagcc acaaagagta cacctgcaag | 660 |

```
gtgacccagg gcacgacctc agtcgtccag agcttcaata ggggtgactg ttag          714
```

<210> SEQ ID NO 7
<211> LENGTH: 705
<212> TYPE: DNA
<213> ORGANISM: Artificial
<220> FEATURE:
<223> OTHER INFORMATION: hybridoma

<400> SEQUENCE: 7

```
atgagggccc ccactcagct gctggggctc ctgctgctct ggctcccagg tgccatatgt    60
gaccctgtac tgacccagac tccatcgtcc gtgtctgcgg ctgtgggagg cacagtcacc   120
atcagttgcc agtccagtga gagtgttttt aagaagaact ggttagcctg gtatcaccag   180
aaaccagggc agtctcccaa cgcctgatc tatggtgcgt ctactctgga atctggggcc    240
ccatcgcggt tcagaggcag tggatctggg acacagttca ctctcaccat cagcgacctg   300
gagtgtggcg atgctgccac ttactactgt gcaggcgctt ttgatggtaa tatttatcct   360
tcggcggag ggaccgaggt ggtcgtcaaa ggtgatccag ttgcacctac tgtcctcatc     420
ttcccaccat ctgctgatct tgtggcaact ggaacagtca ccatcgtgtg tgtggcgaat   480
aaatactttc ccgatgtcac cgtcacctgg gaggtggatg gcaccaccca aacaactggc   540
atcgagaaca gtaaacacc gcagaattct gcagattgta cctacaacct cagcagcact    600
ctgacactga ccagcacaca gtacaacagc acaaagagt acacctgcaa ggtgacccag    660
ggcacgacct cagtcgtcca gagcttcaat aggggtgact gttag                   705
```

<210> SEQ ID NO 8
<211> LENGTH: 236
<212> TYPE: PRT
<213> ORGANISM: Artificial
<220> FEATURE:
<223> OTHER INFORMATION: hybridoma

<400> SEQUENCE: 8

```
Met Arg Ala Pro Thr Gln Leu Leu Gly Leu Leu Leu Leu Trp Leu Pro
 1               5                   10                  15

Gly Ala Thr Phe Ala Ala Val Leu Thr Gln Thr Pro Ser Pro Val Ser
            20                  25                  30

Ala Ala Val Gly Gly Thr Val Thr Ile Thr Cys Gln Ser Ser Gln Ser
        35                  40                  45

Val Tyr Asn Asn Asp Leu Ala Trp Phe Gln Gln Lys Pro Gly Gln
    50                  55                  60

Pro Pro Asn Leu Leu Ile Tyr Arg Ala Ser Lys Leu Ala Ser Gly Val
 65                  70                  75                  80

Pro Pro Arg Phe Ser Gly Ser Gly Ser Gly Thr Gln Phe Thr Phe Thr
                85                  90                  95

Ile Ser Gly Val Gln Cys Asp Asp Ala Ala Thr Tyr Tyr Cys Leu Gly
            100                 105                 110

Ser Tyr Asp Asp Asp Val Asp Thr Cys Ala Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175
```

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235

<210> SEQ ID NO 9
<211> LENGTH: 237
<212> TYPE: PRT
<213> ORGANISM: Artificial
<220> FEATURE:
<223> OTHER INFORMATION: hybridoma

<400> SEQUENCE: 9

Met Arg Ala Pro Thr Gln Leu Leu Gly Leu Leu Leu Trp Leu Pro
1               5                   10                  15

Gly Ala Thr Phe Ala Gln Val Leu Thr Gln Thr Pro Ser Ser Val Ser
            20                  25                  30

Ala Ala Val Gly Gly Thr Val Thr Ile Asn Cys Gln Ala Ser Gln Ser
        35                  40                  45

Leu Tyr Arg Asn Lys Asn Leu Ala Trp Tyr Gln Gln Lys Pro Gly Gln
    50                  55                  60

Pro Pro Lys Leu Leu Ile Tyr Tyr Ala Ser Thr Leu Ala Ser Gly Val
65                  70                  75                  80

Ser Ser Arg Phe Lys Gly Ser Gly Ser Gly Thr Gln Phe Thr Leu Thr
                85                  90                  95

Ile Ser Gly Val Gln Cys Asp Asp Ala Ala Thr Tyr Tyr Cys Gln Gly
            100                 105                 110

Glu Phe Ser Cys Ser Ser Ala Asp Cys Phe Ala Phe Gly Gly Gly Thr
        115                 120                 125

Glu Val Val Val Lys Gly Asp Pro Val Ala Pro Thr Val Leu Ile Phe
    130                 135                 140

Pro Pro Ser Ala Asp Leu Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 10
<211> LENGTH: 235
<212> TYPE: PRT
<213> ORGANISM: Artificial
<220> FEATURE:
<223> OTHER INFORMATION: hybridoma

<400> SEQUENCE: 10

Met Arg Ala Pro Thr Gln Leu Leu Gly Leu Leu Leu Leu Trp Leu Pro
1               5                   10                  15

Gly Ala Arg Cys Ala Val Val Leu Thr Gln Thr Ala Ser Pro Val Ser
            20                  25                  30

Ala Pro Val Gly Gly Thr Val Thr Ile Asn Cys Gln Ala Ser Gln Asn
            35                  40                  45

Ile Tyr Ser Asn Leu Ala Trp Tyr Gln Gln Lys Pro Gly Gln Pro Pro
 50                  55                  60

Lys Leu Leu Ile Tyr Gly Ala Ser Thr Leu Ala Ser Gly Val Ser Ser
65                  70                  75                  80

Arg Phe Lys Gly Ser Arg Ser Gly Thr Glu Phe Thr Leu Thr Ile Ser
                85                  90                  95

Asp Leu Glu Cys Ala Asp Ala Ala Thr Tyr Tyr Cys Gln Ser Tyr Val
            100                 105                 110

Tyr Ser Ser Ser Thr Ala Asp Thr Phe Gly Gly Gly Thr Lys Val Val
            115                 120                 125

Val Glu Val Ala Thr Leu Ala Pro Thr Val Leu Ile Phe Pro Pro Ser
130                 135                 140

Pro Ala Glu Leu Ala Thr Gly Thr Ala Thr Ile Val Cys Val Ala Asn
145                 150                 155                 160

Lys Tyr Phe Pro Asp Gly Thr Val Thr Trp Gln Val Asp Gly Lys Pro
                165                 170                 175

Leu Thr Thr Gly Ile Glu Thr Ser Lys Thr Pro Gln Asn Ser Asp Asp
            180                 185                 190

Cys Thr Tyr Asn Leu Ser Ser Thr Leu Thr Leu Lys Ser Asp Glu Tyr
            195                 200                 205

Asn Ser His Asp Glu Tyr Thr Cys Gln Val Ala Gln Gly Ser Gly Ser
            210                 215                 220

Pro Val Val Gln Ser Phe Ser Arg Lys Asn Cys
225                 230                 235

<210> SEQ ID NO 11
<211> LENGTH: 237
<212> TYPE: PRT
<213> ORGANISM: Artificial
<220> FEATURE:
<223> OTHER INFORMATION: hybridoma

<400> SEQUENCE: 11

Met Arg Ala Pro Thr Gln Leu Leu Gly Phe Leu Leu Leu Trp Leu Pro
1               5                   10                  15

Gly Ala Thr Phe Ser Ile Asp Met Thr Gln Thr Ser Ser Pro Val Ser
            20                  25                  30

Ala Ala Val Gly Gly Thr Val Thr Ile Asn Cys Gln Ala Ser Gln Ser
            35                  40                  45

Val Tyr Asn Asn Lys Asn Leu Ala Trp Tyr Gln Gln Lys Gln Gly Gln
 50                  55                  60

Pro Pro Lys Arg Leu Ile Tyr Gly Ala Ser Thr Leu Asp Ser Gly Val
65                  70                  75                  80

Pro Ser Arg Phe Lys Gly Ser Gly Ser Gly Thr Gln Phe Thr Leu Thr
                85                  90                  95

Ile Asn Asp Leu Glu Cys Asp Asp Ala Ala Thr Tyr Tyr Cys Leu Gly
            100                 105                 110

Glu Phe Tyr Cys Ser Ser Ile Asp Cys Leu Val Phe Gly Gly Gly Thr
            115                 120                 125

Glu Val Val Val Lys Gly Asp Pro Val Ala Pro Thr Val Leu Ile Phe
130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
            165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
            195                 200                 205

Thr Gln Tyr Asn Ser His Lys Glu Tyr Thr Cys Lys Val Thr Gln Gly
            210                 215                 220

Thr Thr Ser Val Ile Leu Ser Phe Asn Arg Gly Asp Cys
225                 230                 235

<210> SEQ ID NO 12
<211> LENGTH: 235
<212> TYPE: PRT
<213> ORGANISM: Artificial
<220> FEATURE:
<223> OTHER INFORMATION: hybridoma

<400> SEQUENCE: 12

Met Arg Ala Pro Thr Gln Leu Leu Gly Leu Leu Leu Trp Leu Pro
1               5                   10                  15

Gly Ala Thr Phe Ala Gln Val Leu Thr Gln Thr Pro Ala Ser Val Ser
            20                  25                  30

Ala Ala Val Gly Gly Thr Val Thr Ile Asn Cys Gln Ser Ser His Ser
            35                  40                  45

Val Tyr Asn Asn Asn Trp Phe Ser Trp Phe Gln Gln Lys Pro Gly Gln
50                  55                  60

Pro Pro Lys Ile Leu Ile Tyr Gly Ala Ser Thr Leu Ala Ser Gly Val
65                  70                  75                  80

Pro Ser Arg Phe Lys Gly Ser Gly Ser Gly Thr Gln Phe Thr Leu Thr
            85                  90                  95

Ile Ser Ser Val Gln Cys Asp Asp Ala Ala Thr Tyr Tyr Cys Gln Gly
            100                 105                 110

Gly Tyr Ser Ser Gly Asp Gly Ile Ala Phe Gly Gly Gly Thr Glu Val
            115                 120                 125

Val Val Lys Gly Asp Pro Val Ala Pro Thr Val Leu Ile Phe Pro Pro
            130                 135                 140

Ser Ala Asp Leu Val Ala Thr Gly Thr Val Thr Ile Val Cys Val Ala
145                 150                 155                 160

Asn Lys Tyr Phe Pro Asp Val Thr Val Thr Trp Glu Val Asp Gly Thr
            165                 170                 175

Thr Gln Thr Thr Gly Ile Glu Asn Ser Lys Thr Pro Gln Asn Ser Ala
            180                 185                 190

Asp Cys Thr Tyr Asn Leu Ser Ser Thr Leu Thr Leu Thr Ser Thr Gln
            195                 200                 205

Tyr Asn Ser His Lys Glu Tyr Thr Cys Lys Val Thr Gln Gly Thr Thr
            210                 215                 220

Ser Val Val Gln Ser Phe Asn Arg Gly Asp Cys
225                 230                 235

<210> SEQ ID NO 13
<211> LENGTH: 237
<212> TYPE: PRT
<213> ORGANISM: Artificial

<220> FEATURE:
<223> OTHER INFORMATION: hybridoma

<400> SEQUENCE: 13

Met Arg Ala Pro Thr Gln Leu Leu Gly Leu Leu Leu Trp Leu Pro
1               5                   10                  15

Gly Ala Thr Phe Ala Gln Val Leu Thr Gln Thr Pro Ser Ser Val Ser
            20                  25                  30

Ala Ala Val Gly Gly Thr Val Thr Ile Asn Cys Gln Ala Ser Gln Ser
            35                  40                  45

Val Tyr Lys Asn Lys Asn Leu Ala Trp Phe Gln Gln Lys Pro Gly Gln
    50                  55                  60

Pro Pro Lys Arg Leu Ile Tyr Gly Ala Ser Thr Leu Asp Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Asp Asp Ala Ala Thr Tyr Tyr Cys Leu Gly
            100                 105                 110

Glu Phe Ser Cys His Ser Val Asp Cys Leu Ala Phe Gly Gly Gly Thr
            115                 120                 125

Glu Val Val Val Lys Gly Asp Pro Val Ala Pro Thr Val Leu Ile Phe
130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
            195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 14
<211> LENGTH: 234
<212> TYPE: PRT
<213> ORGANISM: Artificial
<220> FEATURE:
<223> OTHER INFORMATION: hybridoma

<400> SEQUENCE: 14

Met Arg Ala Pro Thr Gln Leu Leu Gly Leu Leu Leu Trp Leu Pro
1               5                   10                  15

Gly Ala Ile Cys Asp Pro Val Leu Thr Gln Thr Pro Ser Ser Val Ser
            20                  25                  30

Ala Ala Val Gly Gly Thr Val Thr Ile Ser Cys Gln Ser Ser Glu Ser
            35                  40                  45

Val Phe Lys Lys Asn Trp Leu Ala Trp Tyr His Gln Lys Pro Gly Gln
    50                  55                  60

Ser Pro Lys Arg Leu Ile Tyr Gly Ala Ser Thr Leu Glu Ser Gly Ala
65                  70                  75                  80

Pro Ser Arg Phe Arg Gly Ser Gly Ser Gly Thr Gln Phe Thr Leu Thr
                85                  90                  95

Ile Ser Asp Leu Glu Cys Gly Asp Ala Ala Thr Tyr Tyr Cys Ala Gly

```
              100                 105                 110
Ala Phe Asp Gly Asn Ile Tyr Pro Phe Gly Gly Gly Thr Glu Val Val
            115                 120                 125

Val Lys Gly Asp Pro Val Ala Pro Thr Val Leu Ile Phe Pro Pro Ser
130                 135                 140

Ala Asp Leu Val Ala Thr Gly Thr Val Thr Ile Val Cys Val Ala Asn
145                 150                 155                 160

Lys Tyr Phe Pro Asp Val Thr Val Thr Trp Glu Val Asp Gly Thr Thr
            165                 170                 175

Gln Thr Thr Gly Ile Glu Asn Ser Lys Thr Pro Gln Asn Ser Ala Asp
            180                 185                 190

Cys Thr Tyr Asn Leu Ser Ser Thr Leu Thr Leu Thr Ser Thr Gln Tyr
            195                 200                 205

Asn Ser His Lys Glu Tyr Thr Cys Lys Val Thr Gln Gly Thr Thr Ser
            210                 215                 220

Val Val Gln Ser Phe Asn Arg Gly Asp Cys
225                 230
```

<210> SEQ ID NO 15
<211> LENGTH: 1380
<212> TYPE: DNA
<213> ORGANISM: Artificial
<220> FEATURE:
<223> OTHER INFORMATION: hybridoma

<400> SEQUENCE: 15

```
atggagactg gctgcgctg gcttctcctg gtcgctgtac tcaaaggtgt ccagtgtcag    60
gagcagctga aggagaccgg gggaggcctg gtccagcctg ggggatccct gacactctcc   120
tgcaaagcct ctggattcga cttcagtagc tactacatga gctgggtccg ccaggctcca   180
gggaaggggc tggagtggat cggatacatt gatcctgttt ttggtagcac atactacgcg   240
agctgggtga atgccgatt ctccatctcc agcacaacg cccagaacac gctgcatctg    300
caactgaaca gtctgacagc cgcggacacg ccacctatt tctgtgcgag atcgacgggg   360
ctgccttttc acttgtgggg cccaggcacc ctggtcagtg tctcctcagg caacctaag    420
gctccatcag tcttcccact ggcccctgc tgcgggaca cccagctc acggtgacc        480
ctgggctgcc tggtcaaagg ctacctcccg gagccagtga ccgtgacctg aactcgggc   540
accctcacca tggggtacg caccttcccg tccgtccggc agtcctcagg cctctactcg   600
ctgagcagcg tggtgagcgt gacctcaagc agccagcccg tcacctgcaa cgtggcccac   660
ccagccacca caccaaagt ggacaagacc gttgcgccct cgacatgcag caagcccatg   720
tgcccacccc ctgaactcct ggggggaccg tctgtcttca tcttcccccc aaaacccaag   780
gacaccctca tgatctcacg cacccccgag gtcacatgcg tggtggtgga cgtgagccag   840
gatgaccccg aggtgcagtt cacatggtac ataaacaacg agcaggtgcg caccgcccgg   900
ccgccgctac gggagcagca gttcaacagc acgatccgcg tggtcagcac cctccccatc   960
gcgcaccagg actggctgag gggcaaggag ttcaagtgca agtccacaa caaggcactc    1020
ccggccccca tcgagaaaac catctccaaa gccagggggc agcccctgga ccgaaggtc   1080
tacaccatgg gcctccccg ggaggagctg agcagcaggt cggtcagcct gacctgcatg   1140
atcaacggct ctaccccttc cgacatctcg gtggagtggg agaagaacgg gaaggcagag   1200
gacaactaca gaccacgcc gaccgtgctg gacagcgacg gctcctactt cctctacagc   1260
aagctctcag tgcccacgag tgagtggcag cggggcgacg tcttcacctg ctccgtgatg   1320
```

-continued

```
cacgaggcct tgcacaacca ctacacgcag aagtccatct cccgctctcc gggtaaatga    1380
```

<210> SEQ ID NO 16
<211> LENGTH: 1392
<212> TYPE: DNA
<213> ORGANISM: Artificial
<220> FEATURE:
<223> OTHER INFORMATION: hybridoma

<400> SEQUENCE: 16

```
atggagactg ggctgcgctg gcttctcctg gtcgctgtgc tcagaggtgt ccagtgtcag     60
gagcagctgg tggagtccgg gggaggcctg gtccagcctg agggatccct gacactcacc    120
tgcacagcct ctggattctc ctttagtagg ggtgttgtgt cctgggtccg ccaggctcca    180
gggaaagggc tggaattgat cgcagatatg aatattatag ccgatattac ttattacgcg    240
aactgggcga aaggccgatt caccctctcc agaacctcgt cgaccacggt gattctgcaa    300
atgaccagtc tggcagccgc ggacacggcc acctatttct gtgtgagcgg ctcatatatt    360
agtggtagtg gtcttactct ggaattgtgg ggcccaggca ccctggtcac cgtctcctca    420
gggcaaccta aggctccatc agtcttccca ctggccccct gctgcgggga cacacccagc    480
tccacggtga ccctgggctg cctggtcaaa ggctacctcc cggagccagt gaccgtgacc    540
tggaactcgg gcaccctcac caatgggtta cgcaccttcc cgtccgtccg gcagtcctca    600
ggcctctact cgctgagcag cgtggtgagc gtgacctcaa gcagccagcc cgtcacctgc    660
aacgtggccc acccagccac caacaccaaa gtggacaaga ccgttgcgcc ctcgacatgc    720
agcaagccca tgtgcccacc ccctgaactc ctggggggac cgtctgtctt catcttcccc    780
ccaaaaccca aggacaccct catgatctca cgcacccccg aggtcacatg cgtggtggtg    840
gacgtgagcc aggatgaccc cgaggtgcag ttcacatggt acataaacaa cgagcaggtg    900
cgcaccgccc ggccgccgct acgggagcag cagttcaaca gcacgatccg cgtggtcagc    960
accctcccca tcgcgcacca ggactggctg aggggcaagg agttcaagtg caaagtccac    1020
aacaaggcac tcccggcccc catcgagaaa accatctcca agccagaggg cagcccctg     1080 gagccgaagg tctacaccat gggccctccc cgggaggagc tgagcagcag gtcggtcagc    1140
ctgacctgca tgatcaacgg cttctaccct tccgacatct cggtggagtg ggagaagaac    1200
gggaaggcag aggacaacta caagaccacg ccgaccgtgc tggacagcga cggctcctac    1260
ttcctctaca gcaagctctc agtgcccacg agtgagtggc agcggggcga cgtcttcacc    1320
tgctccgtga tgcacgaggc cttgcacaac cactacacgc agaagtccat ctcccgctct    1380
ccgggtaaat ga                                                        1392
```

<210> SEQ ID NO 17
<211> LENGTH: 1380
<212> TYPE: DNA
<213> ORGANISM: Artificial
<220> FEATURE:
<223> OTHER INFORMATION: hybridoma

<400> SEQUENCE: 17

```
atggagactg ggctgcgctg gcttctcctg gtcgctgtgc tcaaaggtgt ccagtgtcag     60
gagcagctgg aggagtccgg gggaggcctg gtcaagcctg aggaaccct gacactcacc    120 tgcaaagcct ctggattctc cttcagtgac ggctattgga tgtgctggat cgccaggct    180 ccagggaagg ggctggagtg gatcggatgc atttatgatg ccagtggtgg cgcatacttc    240
```

-continued

| | | |
|---|---|---|
| ccgagctggg cgaaaggccg attcaccatc tccaaaacct cgtcgaccac ggtgactctg | 300 |
| gaaatgacca gtctgacaga cgcggacacg gccatatatt tctgtgtgaa aactgattat | 360 |
| ggtagttcga agttgtgggg cccaggcacc ctggtcaccg tctcctcagg gcaacctaag | 420 |
| gctccatcag tcttcccact ggccccctgc tgcggggaca cacccagctc cacggtgacc | 480 |
| ctgggctgcc tggtcaaagg ctacctcccg gagccagtga ccgtgacctg gaactcgggc | 540 |
| accctcacca tggggtacg caccttcccg tccgtccggc agtcctcagg cctctactcg | 600 |
| ctgagcagcg tggtgagcgt gacctcaagc agccagcccg tcacctgcaa cgtggcccac | 660 |
| ccagccacca acaccaaagt ggacaagacc gttgcgccct cgacatgcag caagcccatg | 720 |
| tgcccacccc ctgaactcct gggggaccg tctgtcttca tcttccccc aaaacccaag | 780 |
| gacaccctca tgatctcacg cacccccgag gtcacatgcg tggtggtgga cgtgagccag | 840 |
| gatgaccccg aggtgcagtt cacatggtac ataaacaacg agcaggtgcg caccgcccgg | 900 |
| ccgccgctac gggagcagca gttcaacagc acgatccgcg tggtcagcac cctcccatc | 960 |
| gcgcaccagg actggctgag gggcaaggag ttcaagtgca aagtccacaa caaggcactc | 1020 |
| ccggccccca tcgagaaaac catctccaaa gccagagggc agcccctgga gccgaaggtc | 1080 |
| tacaccatgg gccctccccg ggaggagctg agcagcaggt cggtcagcct gacctgcatg | 1140 |
| atcaacggct ctacccttc cgacatctcg gtggagtggg agaagaacgg gaaggcagag | 1200 |
| gacaactaca gaccacgcc gaccgtgctg acagcgacg gctcctactt cctctacagc | 1260 |
| aagctctcag tgcccacgag tgagtggcag cggggcgacg tcttcacctg ctccgtgatg | 1320 |
| cacgaggcct gcacaaccca ctacacgcag aagtccatct cccgctctcc gggtaaatga | 1380 |

<210> SEQ ID NO 18
<211> LENGTH: 1371
<212> TYPE: DNA
<213> ORGANISM: Artificial
<220> FEATURE:
<223> OTHER INFORMATION: hybridoma

<400> SEQUENCE: 18

| | | |
|---|---|---|
| atggagactg gctgcgctg gcttctcctg gtcgctgtgc tcaaaggtgt ccagtgtcag | 60 |
| gagcagctga aggagtccgg aggaggcctg gtaacgcctg gaggaaccct gacactcacc | 120 |
| tgcacagcct ctggattctc cctcagtagc taccacatgg gctgggtccg ccaggctcca | 180 |
| gggaaggggc tggaatacat cggattcatt aatagtgata atagcgcata ctacgcgagc | 240 |
| tggacaagag gccgattcac cgtctccaga acctcgacca cgttggatct gaaagtcacc | 300 |
| agtccgacaa ccgaggacac ggccacctat ttctgtgcca cctatcgtta tgctgctgcc | 360 |
| agtttgtggg gccaggcac cctggtcacc gtcgcctcag gcaacctaa gctccatca | 420 |
| gtcttcccac tggcccctg ctgcggggac acacccagct ccacggtgac cctgggctgc | 480 |
| ctggtcaaag gctacctccc ggagccagtg accgtgacct ggaactcggg caccctcacc | 540 |
| aatggggtac gcaccttccc gtccgtccgg cagtcctcag gcctctactc gctgagcagc | 600 |
| gtggtgagcg tgacctcaag cagccagccc gtcacctgca acgtggccca cccagccacc | 660 |
| aacaccaaag tggacaagac cgttgcgccc tcgacatgca gcaagcccac gtgcccaccc | 720 |
| cctgaactcc tgggggacc gtctgtcttc atcttccccc caaaacccaa ggacaccctc | 780 |
| atgatctcac gcaccccga ggtcacatgc gtggtggtgg acgtgagcca ggatgacccc | 840 |
| gaggtgcagt tcacatggta cataaacaac gagcaggtgc gcaccgcccg ccgccgcta | 900 |
| cgggagcagc agttcaacag cacgatccgc gtggtcagca ccctccccat cgcgcaccag | 960 |

| | |
|---|---|
| gactggctga ggggcaagga gttcaagtgc aaagtccaca acaaggcact cccggcccc | 1020 |
| atcgagaaaa ccatctccaa agccagaggg cagcccctgg agccgaaggt ctacaccatg | 1080 |
| ggccctcccc gggaggagct gagcagcagg tcggtcagcc tgacctgcat gatcaacggc | 1140 |
| ttctacccttt ccgacatctc ggtggagtgg gagaagaacg ggaaggcaga ggacaactac | 1200 |
| aagaccacgc cggccgtgct ggacagcgac ggctcctact tcctctacaa caagctctca | 1260 |
| gtgcccacga gtgagtggca gcggggcgac gtcttcacct gctccgtgat gcacgaggcc | 1320 |
| ttgcacaacc actacacgca gaagtccatc tcccgctctc cgggtaaatg a | 1371 |

<210> SEQ ID NO 19
<211> LENGTH: 1392
<212> TYPE: DNA
<213> ORGANISM: Artificial
<220> FEATURE:
<223> OTHER INFORMATION: hybridoma

<400> SEQUENCE: 19

| | |
|---|---|
| atggagactg gctgcgctg gcttctcctg gtcgctgtgc tcgaaggtgt ccggtgtcag | 60 |
| tcggtggagg agtccggggg tcgcctggtc acgcctggga caccctgac actcacctgc | 120 |
| acagtctctg gattctccct cagtagctat gcaatgagct gggtccgcca ggctccaggg | 180 |
| aaggggctgg aatggatcgg aatcattagt agtagtggtg acacatacta cgcgaactgg | 240 |
| gcggaaggcc gattcaccat ctccaaaacc tcgaccacgg tggatctgaa aatcatcagt | 300 |
| ccgacaaccg aggacacggc cacctatttc tgcgccagag agggggcta cgatgactat | 360 |
| ggggaacacc ttgatgtgct tgatccctgg ggcccaggca ccctggtcac cgtctcctca | 420 |
| gggcaaccta aggctccatc agtcttccca ctggcccct gctgcgggga cacacccagc | 480 |
| tccacggtga ccctgggctg cctggtcaaa ggctacctcc cggagccagt gaccgtgacc | 540 |
| tggaactcgg gcaccctcac caatgggta cgcaccttcc cgtccgtccg gcagtcctca | 600 |
| ggcctctact cgctgagcag cgtggtgagc gtgacctcaa gcagccagcc cgtcacctgc | 660 |
| aacgtggccc acccagccac caacaccaaa gtggacaaga ccgttgcgcc ctcgacatgc | 720 |
| agcaagccca cgtgcccacc ccctgaactc ctggggggac cgtctgtctt catcttcccc | 780 |
| ccaaaaccca aggacaccct catgatctca cgcacccccg aggtcacatg cgtggtggtg | 840 |
| gacgtgagcc aggatgaccc cgaggtgcag ttcacatggt acataaacaa cgagcaggtg | 900 |
| cgcaccgccc ggccgccgct acgggagcag cagttcaaca gcacgatccg cgtggtcagc | 960 |
| accctcccca tcgcgcacca ggactggctg aggggcaagg agttcaagtg caaagtccac | 1020 |
| aacaaggcac tcccggcccc catcgagaaa accatctcca agccagaggg cagcccctg | 1080 |
| gagccgaagg tctacaccat gggccctccc cggaggagc tgagcagcag gtcggtcagc | 1140 |
| ctgacctgca tgatcaacgg cttctaccct tccgacatct cggtggagtg ggagaagaac | 1200 |
| gggaaggcag aggacaacta caagaccacg ccggccgtgc tggacagcga cggctcctac | 1260 |
| ttcctctaca gcaagctctc agtgcccacg agtgagtggc agcggggcga cgtcttcacc | 1320 |
| tgctccgtga tgcacgaggc cttgcacaac cactacacgc agaagtccat ctcccgctct | 1380 |
| ccgggtaaat ga | 1392 |

<210> SEQ ID NO 20
<211> LENGTH: 1359
<212> TYPE: DNA
<213> ORGANISM: Artificial
<220> FEATURE:

<223> OTHER INFORMATION: hybridoma

<400> SEQUENCE: 20

```
atggagactg ggctgcgctg gcttctcctg gtcgctgtgc tcaaaggtgt ccagtgtcag      60
tcagtgaagg agtccgaggg aggtctcttc aagccaacgg acaccctgac actcacctgc     120
acagcctctg gattctccat cagtagctac agaatgcact gggtccgcca ggctccaggg     180
aacgggctgg agtggatcgg ctccattagt agtggtggta gtgctgccta cgcgagctgg     240
gcggatagcc gatccaccat ctccagaaac accaacctga cacggtgac tctgaaaatg      300
accagtctga cagccgcgga cacggccacc tacttctgtg ggagtaatgt catctggggc     360
ccaggcaccc tggtcaccgt ctcctcaggg caacctaagg ctccatcagt cttcccactg     420
gcccctgct gcggggacac acccagctcc acggtgaccc tgggctgcct ggtcaaaggc      480
tacctcccgg agccagtgac cgtgacctgg aactcgggca ccctcaccaa tggggtacgc     540
accttcccgt ccgtccggca gtcctcaggc ctctactcgc tgagcagcgt ggtgagcgtg     600
acctcaagca gccagcccgt cacctgcaac gtggcccacc cagccaccaa caccaaagtg     660
gacaagaccg ttgcgccctc gacatgcagc aagcccacgt gcccaccccc tgaactcctg     720
gggggaccgt ctgtcttcat cttccccca aaacccaagg acaccctcat gatctcacgc     780
acccccgagg tcacatgcgt ggtggtggac gtgagccagg atgaccccga ggtgcagttc     840
acatggtaca taaacaacga gcaggtgcgc accgcccggc cgccgctacg ggagcagcag     900
ttcaacagca cgatccgcgt ggtcagcacc ctccccatcg cgcaccagga ctggctgagg     960
ggcaaggagt tcaagtgcaa agtccacaac aaggcactcc cggcccccat cgagaaaacc    1020
atctccaaag ccagagggca gcccctggag ccgaaggtct acaccatggg ccctccccgg    1080
gaggagctga gcaggtc ggtcagcctg acctgcatga tcaacggctt ctaccccttcc       1140
gacatctcgg tggagtggga gaagaacggg aaggcagagg acaactacaa gaccacgccg    1200
gccgtgctgg acagcgacgg ctcctacttc ctctacagca gctctcagt gcccacgagt      1260
gagtggcagc ggggcgacgt cttcacctgc tccgtgatgc acgaggcctt gcacaaccac    1320
tacacgcaga gtccatctc ccgctctccg ggtaaatga                            1359
```

<210> SEQ ID NO 21
<211> LENGTH: 1359
<212> TYPE: DNA
<213> ORGANISM: Artificial
<220> FEATURE:
<223> OTHER INFORMATION: hybridoma

<400> SEQUENCE: 21

```
atggagactg ggctgcgctg gcttctcctg gtcgctgtgc tcaaaggtgt ccagtgtcag      60
tcagtgaagg agtccgaggg aggtctcttc aagccaacgg ataccctgac actcacctgc     120
acagtctctg gattctccct cagtagctac agaatgcact gggtccgcca ggctccaggg     180
aacgggctgg agtggatcgg atccattagt agtggtggta tgctgccta cgcgaggtgg      240
gcgaatacc gatccaccat caccagaaac accaacctga cacggtgac tctgaaaatg       300
accagcctga cagccgcgga cacggccacc tatttctgtg ggagtaatgt catctggggc     360
ccaggcaccc tggtcaccgt ctcctcaggg caacctaagg ctccatcagt cttcccactg     420
gcccctgct gcggggacac acccagctcc acggtgaccc tgggctgcct ggtcaaaggc      480
tacctcccgg agccagtgac cgtgacctgg aactcgggca ccctcaccaa tggggtacgc     540
accttcccgt ccgtccggca gtcctcaggc ctctactcgc tgagcagcgt ggtgagcgtg     600
```

```
acctcaagca gccagcccgt cacctgcaac gtggcccacc cagccaccaa caccaaagtg    660
gacaagaccg ttgcgccctc gacatgcagc aagcccacgt gcccaccccc tgaactcctg    720
gggggaccgt ctgtcttcat cttcccccca aaacccaagg acaccctcat gatctcacgc    780
acccccgagg tcacatgcgt ggtggtggac gtgagccagg atgaccccga ggtgcagttc    840
acatggtaca taaacaacga gcaggtgcgc accgcccggc cgccgctacg ggagcagcag    900
ttcaacagca cgatccgcgt ggtcagcacc ctccccatcg cgcaccagga ctggctgagg    960
ggcaaggagt tcaagtgcaa agtccacaac aaggcactcc cggcccccat cgagaaaacc   1020
atctccaaag ccagagggca gccccctgga gccgaaggtc tacaccatgg gcctcccccgg   1080 gaggagctga gcagcaggtc ggtcagcctg acctgcatga tcaacggctt ctaccttcc    1140 gacatctcgg tggagtggga agaacgggaa ggcagagg acaactacaa gaccacgccg    1200
gccgtgctgg acagcgacgg ctcctacttc ctctacaaca gctctcagt gcccacgagt    1260 gagtggcagc ggggcgacgt cttcacctgc tccgtgatgc acgaggcctt gcacaaccac   1320
tacacgcaga agtccatctc ccgctctccg ggtaaatga                          1359
```

<210> SEQ ID NO 22
<211> LENGTH: 459
<212> TYPE: PRT
<213> ORGANISM: Artificial
<220> FEATURE:
<223> OTHER INFORMATION: hybridoma

<400> SEQUENCE: 22

```
Met Glu Thr Gly Leu Arg Trp Leu Leu Leu Val Ala Val Leu Lys Gly
1               5                   10                  15

Val Gln Cys Gln Glu Gln Leu Lys Glu Thr Gly Gly Gly Leu Val Gln
            20                  25                  30

Pro Gly Gly Ser Leu Thr Leu Ser Cys Lys Ala Ser Gly Phe Asp Phe
        35                  40                  45

Ser Ser Tyr Tyr Met Ser Trp Val Arg Gln Ala Pro Gly Lys Gly Leu
    50                  55                  60

Glu Trp Ile Gly Tyr Ile Asp Pro Val Phe Gly Ser Thr Tyr Tyr Ala
65                  70                  75                  80

Ser Trp Val Asn Gly Arg Phe Ser Ile Ser Ser His Asn Ala Gln Asn
                85                  90                  95

Thr Leu His Leu Gln Leu Asn Ser Leu Thr Ala Ala Asp Thr Ala Thr
            100                 105                 110

Tyr Phe Cys Ala Arg Ser Thr Gly Leu Pro Phe His Leu Trp Gly Pro
        115                 120                 125

Gly Thr Leu Val Ser Val Ser Ser Gly Gln Pro Lys Ala Pro Ser Val
    130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
        195                 200                 205

Ser Ser Ser Gln Pro Val Thr Cys Asn Val Ala His Pro Ala Thr Asn
    210                 215                 220
```

-continued

```
Thr Lys Val Asp Lys Thr Val Ala Pro Ser Thr Cys Ser Lys Pro Met
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Pro Glu Val Gln Phe Thr
        275                 280                 285

Trp Tyr Ile Asn Asn Glu Gln Val Arg Thr Ala Arg Pro Pro Leu Arg
    290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
        355                 360                 365

Glu Leu Ser Ser Arg Ser Val Ser Leu Thr Cys Met Ile Asn Gly Phe
370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Thr Val Leu Asp Ser Asp Gly Ser Tyr
                405                 410                 415

Phe Leu Tyr Ser Lys Leu Ser Val Pro Thr Ser Glu Trp Gln Arg Gly
            420                 425                 430

Asp Val Phe Thr Cys Ser Val Met His Glu Ala Leu His Asn His Tyr
        435                 440                 445

Thr Gln Lys Ser Ile Ser Arg Ser Pro Gly Lys
    450                 455

<210> SEQ ID NO 23
<211> LENGTH: 463
<212> TYPE: PRT
<213> ORGANISM: Artificial
<220> FEATURE:
<223> OTHER INFORMATION: hybridoma

<400> SEQUENCE: 23

Met Glu Thr Gly Leu Arg Trp Leu Leu Leu Val Ala Val Leu Arg Gly
1               5                   10                  15

Val Gln Cys Gln Glu Gln Leu Val Glu Ser Gly Gly Gly Leu Val Gln
                20                  25                  30

Pro Glu Gly Ser Leu Thr Leu Thr Cys Thr Ala Ser Gly Phe Ser Phe
            35                  40                  45

Ser Arg Gly Val Val Ser Trp Val Arg Gln Ala Pro Gly Lys Gly Leu
        50                  55                  60

Glu Leu Ile Ala Asp Met Asn Ile Ile Ala Asp Ile Thr Tyr Tyr Ala
65                  70                  75                  80

Asn Trp Ala Lys Gly Arg Phe Thr Leu Ser Arg Thr Ser Ser Thr Thr
                85                  90                  95

Val Ile Leu Gln Met Thr Ser Leu Ala Ala Ala Asp Thr Ala Thr Tyr
            100                 105                 110

Phe Cys Val Ser Gly Ser Tyr Ile Ser Gly Ser Gly Leu Thr Leu Glu
        115                 120                 125
```

```
Leu Trp Gly Pro Gly Thr Leu Val Thr Val Ser Ser Gly Gln Pro Lys
130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
                180                 185                 190

Phe Pro Ser Val Arg Gln Ser Ser Gly Leu Tyr Ser Leu Ser Ser Val
                195                 200                 205

Val Ser Val Thr Ser Ser Gln Pro Val Thr Cys Asn Val Ala His
210                 215                 220

Pro Ala Thr Asn Thr Lys Val Asp Lys Thr Val Ala Pro Ser Thr Cys
225                 230                 235                 240

Ser Lys Pro Met Cys Pro Pro Glu Leu Leu Gly Gly Pro Ser Val
                245                 250                 255

Phe Ile Phe Pro Pro Lys Pro Lys Asp Thr Leu Met Ile Ser Arg Thr
                260                 265                 270

Pro Glu Val Thr Cys Val Val Val Asp Val Ser Gln Asp Asp Pro Glu
                275                 280                 285

Val Gln Phe Thr Trp Tyr Ile Asn Asn Glu Gln Val Arg Thr Ala Arg
290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
                340                 345                 350

Ser Lys Ala Arg Gly Gln Pro Leu Glu Pro Lys Val Tyr Thr Met Gly
                355                 360                 365

Pro Pro Arg Glu Glu Leu Ser Ser Arg Ser Val Ser Leu Thr Cys Met
370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Thr Val Leu Asp Ser
                405                 410                 415

Asp Gly Ser Tyr Phe Leu Tyr Ser Lys Leu Ser Val Pro Thr Ser Glu
                420                 425                 430

Trp Gln Arg Gly Asp Val Phe Thr Cys Ser Val Met His Glu Ala Leu
                435                 440                 445

His Asn His Tyr Thr Gln Lys Ser Ile Ser Arg Ser Pro Gly Lys
    450                 455                 460

<210> SEQ ID NO 24
<211> LENGTH: 459
<212> TYPE: PRT
<213> ORGANISM: Artificial
<220> FEATURE:
<223> OTHER INFORMATION: hybridoma

<400> SEQUENCE: 24

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Gly Leu Val Lys
            20                  25                  30
```

-continued

```
Pro Gly Gly Thr Leu Thr Leu Thr Cys Lys Ala Ser Gly Phe Ser Phe
            35                  40                  45
Ser Asp Gly Tyr Trp Met Cys Trp Ile Arg Gln Ala Pro Gly Lys Gly
 50                  55                  60
Leu Glu Trp Ile Gly Cys Ile Tyr Asp Ala Ser Gly Gly Ala Tyr Phe
 65                  70                  75                  80
Pro Ser Trp Ala Lys Gly Arg Phe Thr Ile Ser Lys Thr Ser Ser Thr
                 85                  90                  95
Thr Val Thr Leu Glu Met Thr Ser Leu Thr Asp Ala Asp Thr Ala Ile
                100                 105                 110
Tyr Phe Cys Val Lys Thr Asp Tyr Gly Ser Ser Lys Leu Trp Gly Pro
            115                 120                 125
Gly Thr Leu Val Thr Val Ser Ser Gly Gln Pro Lys Ala Pro Ser Val
        130                 135                 140
Phe Pro Leu Ala Pro Cys Cys Gly Asp Thr Pro Ser Ser Thr Val Thr
145                 150                 155                 160
Leu Gly Cys Leu Val Lys Gly Tyr Leu Pro Glu Pro Val Thr Val Thr
                165                 170                 175
Trp Asn Ser Gly Thr Leu Thr Asn Gly Val Arg Thr Phe Pro Ser Val
            180                 185                 190
Arg Gln Ser Ser Gly Leu Tyr Ser Leu Ser Ser Val Val Ser Val Thr
        195                 200                 205
Ser Ser Ser Gln Pro Val Thr Cys Asn Val Ala His Pro Ala Thr Asn
    210                 215                 220
Thr Lys Val Asp Lys Thr Val Ala Pro Ser Thr Cys Ser Lys Pro Met
225                 230                 235                 240
Cys Pro Pro Pro Glu Leu Leu Gly Gly Pro Ser Val Phe Ile Phe Pro
                245                 250                 255
Pro Lys Pro Lys Asp Thr Leu Met Ile Ser Arg Thr Pro Glu Val Thr
            260                 265                 270
Cys Val Val Val Asp Val Ser Gln Asp Asp Pro Glu Val Gln Phe Thr
        275                 280                 285
Trp Tyr Ile Asn Asn Glu Gln Val Arg Thr Ala Arg Pro Pro Leu Arg
    290                 295                 300
Glu Gln Gln Phe Asn Ser Thr Ile Arg Val Val Ser Thr Leu Pro Ile
305                 310                 315                 320
Ala His Gln Asp Trp Leu Arg Gly Lys Glu Phe Lys Cys Lys Val His
                325                 330                 335
Asn Lys Ala Leu Pro Ala Pro Ile Glu Lys Thr Ile Ser Lys Ala Arg
            340                 345                 350
Gly Gln Pro Leu Glu Pro Lys Val Tyr Thr Met Gly Pro Pro Arg Glu
        355                 360                 365
Glu Leu Ser Ser Arg Ser Val Ser Leu Thr Cys Met Ile Asn Gly Phe
    370                 375                 380
Tyr Pro Ser Asp Ile Ser Val Glu Trp Glu Lys Asn Gly Lys Ala Glu
385                 390                 395                 400
Asp Asn Tyr Lys Thr Thr Pro Thr Val Leu Asp Ser Asp Gly Ser Tyr
                405                 410                 415
Phe Leu Tyr Ser Lys Leu Ser Val Pro Thr Ser Glu Trp Gln Arg Gly
            420                 425                 430
Asp Val Phe Thr Cys Ser Val Met His Glu Ala Leu His Asn His Tyr
        435                 440                 445
Thr Gln Lys Ser Ile Ser Arg Ser Pro Gly Lys
```

<210> SEQ ID NO 25
<211> LENGTH: 456
<212> TYPE: PRT
<213> ORGANISM: Artificial
<220> FEATURE:
<223> OTHER INFORMATION: hybridoma

<400> SEQUENCE: 25

```
Met Glu Thr Gly Leu Arg Trp Leu Leu Leu Val Ala Val Leu Lys Gly
1               5                   10                  15

Val Gln Cys Gln Glu Gln Leu Lys Glu Ser Gly Gly Gly Leu Val Thr
            20                  25                  30

Pro Gly Gly Thr Leu Thr Leu Thr Cys Thr Ala Ser Gly Phe Ser Leu
        35                  40                  45

Ser Ser Tyr His Met Gly Trp Val Arg Gln Ala Pro Gly Lys Gly Leu
    50                  55                  60

Glu Tyr Ile Gly Phe Ile Asn Ser Asp Asn Ser Ala Tyr Tyr Ala Ser
65                  70                  75                  80

Trp Thr Arg Gly Arg Phe Thr Val Ser Arg Thr Ser Thr Thr Leu Asp
                85                  90                  95

Leu Lys Val Thr Ser Pro Thr Thr Glu Asp Thr Ala Thr Tyr Phe Cys
            100                 105                 110

Ala Thr Tyr Arg Tyr Ala Ala Ala Ser Leu Trp Gly Pro Gly Thr Leu
        115                 120                 125

Val Thr Val Ala Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Pro Leu Arg Glu Gln Gln
    290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
```

```
                355                 360                 365
Ser Arg Ser Val Ser Leu Thr Cys Met Ile Asn Gly Phe Tyr Pro Ser
370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Asn Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
450                 455

<210> SEQ ID NO 26
<211> LENGTH: 463
<212> TYPE: PRT
<213> ORGANISM: Artificial
<220> FEATURE:
<223> OTHER INFORMATION: hybridoma

<400> SEQUENCE: 26

Met Glu Thr Gly Leu Arg Trp Leu Leu Leu Val Ala Val Leu Glu Gly
1               5                   10                  15

Val Arg Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Ser Tyr Ala Met Ser Trp Val Arg Gln Ala Pro Gly Lys Gly Leu Glu
    50                  55                  60

Trp Ile Gly Ile Ile Ser Ser Gly Asp Thr Tyr Tyr Ala Asn Trp
65                  70                  75                  80

Ala Glu Gly Arg Phe Thr Ile Ser Lys Thr Ser Thr Thr Val Asp Leu
                85                  90                  95

Lys Ile Ile Ser Pro Thr Thr Glu Asp Thr Ala Thr Tyr Phe Cys Ala
            100                 105                 110

Arg Glu Gly Gly Tyr Asp Asp Tyr Gly Glu His Leu Asp Val Leu Asp
        115                 120                 125

Pro Trp Gly Pro Gly Thr Leu Val Thr Val Ser Ser Gly Gln Pro Lys
130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Ser Gln Pro Val Thr Cys Asn Val Ala His
    210                 215                 220

Pro Ala Thr Asn Thr Lys Val Asp Lys Thr Val Ala Pro Ser Thr Cys
225                 230                 235                 240

Ser Lys Pro Thr Cys Pro Pro Pro Glu Leu Leu Gly Gly Pro Ser Val
                245                 250                 255

Phe Ile Phe Pro Pro Lys Pro Lys Asp Thr Leu Met Ile Ser Arg Thr
```

-continued

```
                260                 265                 270
Pro Glu Val Thr Cys Val Val Asp Val Ser Gln Asp Asp Pro Glu
            275                 280                 285

Val Gln Phe Thr Trp Tyr Ile Asn Asn Glu Gln Val Arg Thr Ala Arg
        290                 295                 300

Pro Pro Leu Arg Glu Gln Gln Phe Asn Ser Thr Ile Arg Val Val Ser
305                 310                 315                 320

Thr Leu Pro Ile Ala His Gln Asp Trp Leu Arg Gly Lys Glu Phe Lys
                325                 330                 335

Cys Lys Val His Asn Lys Ala Leu Pro Ala Pro Ile Glu Lys Thr Ile
            340                 345                 350

Ser Lys Ala Arg Gly Gln Pro Leu Glu Pro Lys Val Tyr Thr Met Gly
        355                 360                 365

Pro Pro Arg Glu Glu Leu Ser Ser Arg Ser Val Ser Leu Thr Cys Met
    370                 375                 380

Ile Asn Gly Phe Tyr Pro Ser Asp Ile Ser Val Glu Trp Glu Lys Asn
385                 390                 395                 400

Gly Lys Ala Glu Asp Asn Tyr Lys Thr Thr Pro Ala Val Leu Asp Ser
                405                 410                 415

Asp Gly Ser Tyr Phe Leu Tyr Ser Lys Leu Ser Val Pro Thr Ser Glu
            420                 425                 430

Trp Gln Arg Gly Asp Val Phe Thr Cys Ser Val Met His Glu Ala Leu
        435                 440                 445

His Asn His Tyr Thr Gln Lys Ser Ile Ser Arg Ser Pro Gly Lys
    450                 455                 460

<210> SEQ ID NO 27
<211> LENGTH: 452
<212> TYPE: PRT
<213> ORGANISM: Artificial
<220> FEATURE:
<223> OTHER INFORMATION: hybridoma

<400> SEQUENCE: 27

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Ala Ser Gly Phe Ser Ile Ser
        35                  40                  45

Ser Tyr Arg Met His Trp Val Arg Gln Ala Pro Gly Asn Gly Leu Glu
    50                  55                  60

Trp Ile Gly Ser Ile Ser Ser Gly Gly Ser Ala Ala Tyr Ala Ser Trp
65                  70                  75                  80

Ala Asp Ser Arg Ser Thr Ile Ser Arg Asn Thr Asn Leu Asn Thr Val
                85                  90                  95

Thr Leu Lys Met Thr Ser Leu Thr Ala Ala Asp Thr Ala Thr Tyr Phe
            100                 105                 110

Cys Gly Ser Asn Val Ile Trp Gly Pro Gly Thr Leu Val Thr Val Ser
        115                 120                 125

Ser Gly Gln Pro Lys Ala Pro Ser Val Phe Pro Leu Ala Pro Cys Cys
    130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
```

```
            165                 170                 175
Asn Gly Val Arg Thr Phe Pro Ser Val Arg Gln Ser Ser Gly Leu Tyr
            180                 185                 190

Ser Leu Ser Ser Val Val Ser Val Thr Ser Ser Ser Gln Pro Val Thr
        195                 200                 205

Cys Asn Val Ala His Pro Ala Thr Asn Thr Lys Val Asp Lys Thr Val
210                 215                 220

Ala Pro Ser Thr Cys Ser Lys Pro Thr Cys Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Asp Asp Pro Glu Val Gln Phe Thr Trp Tyr Ile Asn Asn Glu Gln
        275                 280                 285

Val Arg Thr Ala Arg Pro Pro Leu Arg Glu Gln Gln Phe Asn Ser Thr
    290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
        355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Ser Lys Leu Ser
                405                 410                 415

Val Pro Thr Ser Glu Trp Gln Arg Gly Asp Val Phe Thr Cys Ser Val
            420                 425                 430

Met His Glu Ala Leu His Asn His Tyr Thr Gln Lys Ser Ile Ser Arg
        435                 440                 445

Ser Pro Gly Lys
    450

<210> SEQ ID NO 28
<211> LENGTH: 452
<212> TYPE: PRT
<213> ORGANISM: Artificial
<220> FEATURE:
<223> OTHER INFORMATION: hybridoma

<400> SEQUENCE: 28

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Leu Thr Cys Thr Val Ser Gly Phe Ser Leu Ser
        35                  40                  45

Ser Tyr Arg Met His Trp Val Arg Gln Ala Pro Gly Asn Gly Leu Glu
    50                  55                  60

Trp Ile Gly Ser Ile Ser Ser Gly Gly Asn Ala Ala Tyr Ala Arg Trp
```

```
            65                  70                  75                  80
Ala Asn Thr Arg Ser Thr Ile Thr Arg Asn Thr Asn Leu Asn Thr Val
                    85                  90                  95

Thr Leu Lys Met Thr Ser Leu Thr Ala Ala Asp Thr Ala Thr Tyr Phe
               100                 105                 110

Cys Gly Ser Asn Val Ile Trp Gly Pro Gly Thr Leu Val Thr Val Ser
               115                 120                 125

Ser Gly Gln Pro Lys Ala Pro Ser Val Phe Pro Leu Ala Pro Cys Cys
           130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
                180                 185                 190

Ser Leu Ser Ser Val Val Ser Val Thr Ser Ser Ser Gln Pro Val Thr
            195                 200                 205

Cys Asn Val Ala His Pro Ala Thr Asn Thr Lys Val Asp Lys Thr Val
        210                 215                 220

Ala Pro Ser Thr Cys Ser Lys Pro Thr Cys Pro Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Asp Asp Pro Glu Val Gln Phe Thr Trp Tyr Ile Asn Asn Glu Gln
            275                 280                 285

Val Arg Thr Ala Arg Pro Pro Leu Arg Glu Gln Gln Phe Asn Ser Thr
        290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
        355                 360                 365

Ser Leu Thr Cys Met Ile Asn Gly Phe Tyr Pro Ser Asp Ile Ser Val
    370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Asn Lys Leu Ser
                405                 410                 415

Val Pro Thr Ser Glu Trp Gln Arg Gly Asp Val Phe Thr Cys Ser Val
            420                 425                 430

Met His Glu Ala Leu His Asn His Tyr Thr Gln Lys Ser Ile Ser Arg
        435                 440                 445

Ser Pro Gly Lys
        450

<210> SEQ ID NO 29
<211> LENGTH: 8
<212> TYPE: PRT
<213> ORGANISM: Artificial
```

```
<220> FEATURE:
<223> OTHER INFORMATION: hybridoma

<400> SEQUENCE: 29

Gln Ser Val Tyr Asn Asn Asp
1               5

<210> SEQ ID NO 30
<211> LENGTH: 3
<212> TYPE: PRT
<213> ORGANISM: Artificial
<220> FEATURE:
<223> OTHER INFORMATION: hybridoma

<400> SEQUENCE: 30

Arg Ala Ser
1

<210> SEQ ID NO 31
<211> LENGTH: 12
<212> TYPE: PRT
<213> ORGANISM: Artificial
<220> FEATURE:
<223> OTHER INFORMATION: hybridoma

<400> SEQUENCE: 31

Leu Gly Ser Tyr Asp Asp Asp Val Asp Thr Cys Ala
1               5                   10

<210> SEQ ID NO 32
<211> LENGTH: 8
<212> TYPE: PRT
<213> ORGANISM: Artificial
<220> FEATURE:
<223> OTHER INFORMATION: hybridoma

<400> SEQUENCE: 32

Gln Ser Leu Tyr Arg Asn Lys Asn
1               5

<210> SEQ ID NO 33
<211> LENGTH: 3
<212> TYPE: PRT
<213> ORGANISM: Artificial
<220> FEATURE:
<223> OTHER INFORMATION: hybridoma

<400> SEQUENCE: 33

Tyr Ala Ser
1

<210> SEQ ID NO 34
<211> LENGTH: 13
<212> TYPE: PRT
<213> ORGANISM: Artificial
<220> FEATURE:
<223> OTHER INFORMATION: hybridoma

<400> SEQUENCE: 34

Gln Gly Glu Phe Ser Cys Ser Ser Ala Asp Cys Phe Ala
1               5                   10

<210> SEQ ID NO 35
<211> LENGTH: 6
<212> TYPE: PRT
<213> ORGANISM: Artificial
<220> FEATURE:
```

<223> OTHER INFORMATION: hybridoma

<400> SEQUENCE: 35

Gln Asn Ile Tyr Ser Asn
1               5

<210> SEQ ID NO 36
<211> LENGTH: 3
<212> TYPE: PRT
<213> ORGANISM: Artificial
<220> FEATURE:
<223> OTHER INFORMATION: hybridoma

<400> SEQUENCE: 36

Gly Ala Ser
1

<210> SEQ ID NO 37
<211> LENGTH: 12
<212> TYPE: PRT
<213> ORGANISM: Artificial
<220> FEATURE:
<223> OTHER INFORMATION: hybridoma

<400> SEQUENCE: 37

Gln Ser Tyr Val Tyr Ser Ser Thr Ala Asp Thr
1               5                   10

<210> SEQ ID NO 38
<211> LENGTH: 8
<212> TYPE: PRT
<213> ORGANISM: Artificial
<220> FEATURE:
<223> OTHER INFORMATION: hybridoma

<400> SEQUENCE: 38

Gln Ser Val Tyr Asn Asn Lys Asn
1               5

<210> SEQ ID NO 39
<211> LENGTH: 13
<212> TYPE: PRT
<213> ORGANISM: Artificial
<220> FEATURE:
<223> OTHER INFORMATION: hybridoma

<400> SEQUENCE: 39

Leu Gly Glu Phe Tyr Cys Ser Ser Ile Asp Cys Leu Val
1               5                   10

<210> SEQ ID NO 40
<211> LENGTH: 8
<212> TYPE: PRT
<213> ORGANISM: Artificial
<220> FEATURE:
<223> OTHER INFORMATION: hybridoma

<400> SEQUENCE: 40

His Ser Val Tyr Asn Asn Asn Trp
1               5

<210> SEQ ID NO 41
<211> LENGTH: 11
<212> TYPE: PRT
<213> ORGANISM: Artificial
<220> FEATURE:
<223> OTHER INFORMATION: hybridoma

```
<400> SEQUENCE: 41

Gln Gly Gly Tyr Ser Ser Gly Asp Gly Ile Ala
1               5                   10

<210> SEQ ID NO 42
<211> LENGTH: 8
<212> TYPE: PRT
<213> ORGANISM: Artificial
<220> FEATURE:
<223> OTHER INFORMATION: hybridoma

<400> SEQUENCE: 42

Gln Ser Val Tyr Lys Asn Lys Asn
1               5

<210> SEQ ID NO 43
<211> LENGTH: 13
<212> TYPE: PRT
<213> ORGANISM: Artificial
<220> FEATURE:
<223> OTHER INFORMATION: hybridoma

<400> SEQUENCE: 43

Leu Gly Glu Phe Ser Cys His Ser Val Asp Cys Leu Ala
1               5                   10

<210> SEQ ID NO 44
<211> LENGTH: 8
<212> TYPE: PRT
<213> ORGANISM: Artificial
<220> FEATURE:
<223> OTHER INFORMATION: hybridoma

<400> SEQUENCE: 44

Glu Ser Val Phe Lys Lys Asn Trp
1               5

<210> SEQ ID NO 45
<211> LENGTH: 10
<212> TYPE: PRT
<213> ORGANISM: Artificial
<220> FEATURE:
<223> OTHER INFORMATION: hybridoma

<400> SEQUENCE: 45

Ala Gly Ala Phe Asp Gly Asn Ile Tyr Pro
1               5                   10

<210> SEQ ID NO 46
<211> LENGTH: 6
<212> TYPE: PRT
<213> ORGANISM: Artificial
<220> FEATURE:
<223> OTHER INFORMATION: hybridoma

<400> SEQUENCE: 46

Gly Phe Asp Phe Ser Ser
1               5

<210> SEQ ID NO 47
<211> LENGTH: 7
<212> TYPE: PRT
<213> ORGANISM: Artificial
<220> FEATURE:
<223> OTHER INFORMATION: hybridoma
```

```
<400> SEQUENCE: 47

Tyr Ile Asp Pro Val Phe Gly
1               5

<210> SEQ ID NO 48
<211> LENGTH: 6
<212> TYPE: PRT
<213> ORGANISM: Artificial
<220> FEATURE:
<223> OTHER INFORMATION: hybridoma

<400> SEQUENCE: 48

Phe Cys Ala Arg Ser Thr
1               5

<210> SEQ ID NO 49
<211> LENGTH: 7
<212> TYPE: PRT
<213> ORGANISM: Artificial
<220> FEATURE:
<223> OTHER INFORMATION: hybridoma

<400> SEQUENCE: 49

Gly Phe Ser Phe Ser Arg Gly
1               5

<210> SEQ ID NO 50
<211> LENGTH: 7
<212> TYPE: PRT
<213> ORGANISM: Artificial
<220> FEATURE:
<223> OTHER INFORMATION: hybridoma

<400> SEQUENCE: 50

Asp Met Asn Ile Ile Ala Asp
1               5

<210> SEQ ID NO 51
<211> LENGTH: 6
<212> TYPE: PRT
<213> ORGANISM: Artificial
<220> FEATURE:
<223> OTHER INFORMATION: hybridoma

<400> SEQUENCE: 51

Phe Cys Val Ser Gly Ser
1               5

<210> SEQ ID NO 52
<211> LENGTH: 7
<212> TYPE: PRT
<213> ORGANISM: Artificial
<220> FEATURE:
<223> OTHER INFORMATION: hybridoma

<400> SEQUENCE: 52

Gly Phe Ser Phe Ser Asp Gly
1               5

<210> SEQ ID NO 53
<211> LENGTH: 7
<212> TYPE: PRT
<213> ORGANISM: Artificial
<220> FEATURE:
<223> OTHER INFORMATION: hybridoma

<400> SEQUENCE: 53
```

```
Cys Ile Tyr Asp Ala Ser Gly
1               5

<210> SEQ ID NO 54
<211> LENGTH: 6
<212> TYPE: PRT
<213> ORGANISM: Artificial
<220> FEATURE:
<223> OTHER INFORMATION: hybridoma

<400> SEQUENCE: 54

Phe Cys Val Lys Thr Asp
1               5

<210> SEQ ID NO 55
<211> LENGTH: 6
<212> TYPE: PRT
<213> ORGANISM: Artificial
<220> FEATURE:
<223> OTHER INFORMATION: hybridoma

<400> SEQUENCE: 55

Gly Phe Ser Leu Ser Ser
1               5

<210> SEQ ID NO 56
<211> LENGTH: 6
<212> TYPE: PRT
<213> ORGANISM: Artificial
<220> FEATURE:
<223> OTHER INFORMATION: hybridoma

<400> SEQUENCE: 56

Phe Ile Asn Ser Asp Asn
1               5

<210> SEQ ID NO 57
<211> LENGTH: 6
<212> TYPE: PRT
<213> ORGANISM: Artificial
<220> FEATURE:
<223> OTHER INFORMATION: hybridoma

<400> SEQUENCE: 57

Phe Cys Ala Thr Tyr Arg
1               5

<210> SEQ ID NO 58
<211> LENGTH: 6
<212> TYPE: PRT
<213> ORGANISM: Artificial
<220> FEATURE:
<223> OTHER INFORMATION: hybridoma

<400> SEQUENCE: 58

Ile Ile Ser Ser Ser Gly
1               5

<210> SEQ ID NO 59
<211> LENGTH: 6
<212> TYPE: PRT
<213> ORGANISM: Artificial
<220> FEATURE:
<223> OTHER INFORMATION: hybridoma

<400> SEQUENCE: 59
```

```
Phe Cys Ala Arg Glu Gly
1               5

<210> SEQ ID NO 60
<211> LENGTH: 6
<212> TYPE: PRT
<213> ORGANISM: Artificial
<220> FEATURE:
<223> OTHER INFORMATION: hybridoma

<400> SEQUENCE: 60

Gly Phe Ser Ile Ser Ser
1               5

<210> SEQ ID NO 61
<211> LENGTH: 6
<212> TYPE: PRT
<213> ORGANISM: Artificial
<220> FEATURE:
<223> OTHER INFORMATION: hybridoma

<400> SEQUENCE: 61

Ser Ile Ser Ser Gly Gly
1               5

<210> SEQ ID NO 62
<211> LENGTH: 4
<212> TYPE: PRT
<213> ORGANISM: Artificial
<220> FEATURE:
<223> OTHER INFORMATION: hybridoma

<400> SEQUENCE: 62

Phe Cys Gly Ser
1

<210> SEQ ID NO 63
<211> LENGTH: 24
<212> TYPE: PRT
<213> ORGANISM: Human

<400> SEQUENCE: 63

Trp Tyr Lys Phe Asp Glu Asn Tyr Ala Phe Leu His Arg Thr Leu Lys
1               5                   10                  15

Glu Ile Leu Arg Tyr Leu Met Asp
            20

<210> SEQ ID NO 64
<211> LENGTH: 28
<212> TYPE: PRT
<213> ORGANISM: Human

<400> SEQUENCE: 64

Pro Phe Gln Pro Trp Asp Gly Leu Glu Glu His Ser Gln Ala Leu Ser
1               5                   10                  15

Gly Arg Leu Arg Ala Ile Leu Gln Asn Gln Gly Asn
            20                  25

<210> SEQ ID NO 65
<211> LENGTH: 46
<212> TYPE: DNA
<213> ORGANISM: Artificial
<220> FEATURE:
<223> OTHER INFORMATION: adapter
<220> FEATURE:
<221> NAME/KEY: misc_feature
```

```
<222> LOCATION: (46)..(46)
<223> OTHER INFORMATION: n is a, c, g, or t

<400> SEQUENCE: 65
gcgagcacag aattaatacg actcactata ggttttttttt ttttvn            46

<210> SEQ ID NO 66
<211> LENGTH: 19
<212> TYPE: DNA
<213> ORGANISM: Artificial
<220> FEATURE:
<223> OTHER INFORMATION: primer

<400> SEQUENCE: 66
atcagtcttc ccactggcc                                            19

<210> SEQ ID NO 67
<211> LENGTH: 17
<212> TYPE: DNA
<213> ORGANISM: Artificial
<220> FEATURE:
<223> OTHER INFORMATION: primer

<400> SEQUENCE: 67
gggacacacc cagctcc                                              17

<210> SEQ ID NO 68
<211> LENGTH: 16
<212> TYPE: DNA
<213> ORGANISM: Artificial
<220> FEATURE:
<223> OTHER INFORMATION: primer

<400> SEQUENCE: 68
catgagggcc cccact                                               16

<210> SEQ ID NO 69
<211> LENGTH: 17
<212> TYPE: DNA
<213> ORGANISM: Artificial
<220> FEATURE:
<223> OTHER INFORMATION: primer

<400> SEQUENCE: 69
tcctgctgct ctggctc                                              17

<210> SEQ ID NO 70
<211> LENGTH: 23
<212> TYPE: DNA
<213> ORGANISM: Artificial
<220> FEATURE:
<223> OTHER INFORMATION: primer

<400> SEQUENCE: 70
gcgagcacag aattaatacg act                                       23

<210> SEQ ID NO 71
<211> LENGTH: 32
<212> TYPE: DNA
<213> ORGANISM: Artificial
<220> FEATURE:
<223> OTHER INFORMATION: primer

<400> SEQUENCE: 71
cgcggatccg aattaatacg actcactata gg                             32
```

```
<210> SEQ ID NO 72
<211> LENGTH: 32
<212> TYPE: DNA
<213> ORGANISM: Artificial
<220> FEATURE:
<223> OTHER INFORMATION: primer

<400> SEQUENCE: 72
gcgaggcgag aagaacacgc ggcggcgaga aa                              32

<210> SEQ ID NO 73
<211> LENGTH: 24
<212> TYPE: DNA
<213> ORGANISM: Artificial
<220> FEATURE:
<223> OTHER INFORMATION: primer

<400> SEQUENCE: 73
gctgatggcg atgaatgaac actg                                       24

<210> SEQ ID NO 74
<211> LENGTH: 35
<212> TYPE: DNA
<213> ORGANISM: Artificial
<220> FEATURE:
<223> OTHER INFORMATION: primer

<400> SEQUENCE: 74
cgcggatccg aacactgcgt ttgctggctt tgatg                           35

<210> SEQ ID NO 75
<211> LENGTH: 19
<212> TYPE: DNA
<213> ORGANISM: Artificial
<220> FEATURE:
<223> OTHER INFORMATION: primer

<400> SEQUENCE: 75
ggccagtggg aagactgat                                             19

<210> SEQ ID NO 76
<211> LENGTH: 17
<212> TYPE: DNA
<213> ORGANISM: Artificial
<220> FEATURE:
<223> OTHER INFORMATION: primer

<400> SEQUENCE: 76
ggagctgggt gtgtccc                                               17

<210> SEQ ID NO 77
<211> LENGTH: 20
<212> TYPE: DNA
<213> ORGANISM: Artificial
<220> FEATURE:
<223> OTHER INFORMATION: primer

<400> SEQUENCE: 77
ccgggaggta gcctttgacc                                            20

<210> SEQ ID NO 78
<211> LENGTH: 19
<212> TYPE: DNA
<213> ORGANISM: Artificial
<220> FEATURE:
<223> OTHER INFORMATION: primer
```

<400> SEQUENCE: 78
gagggtgccc gagttccag                                                19

<210> SEQ ID NO 79
<211> LENGTH: 19
<212> TYPE: DNA
<213> ORGANISM: Artificial
<220> FEATURE:
<223> OTHER INFORMATION: primer

<400> SEQUENCE: 79
crgtgaccag ggtgccctg                                                19

<210> SEQ ID NO 80
<211> LENGTH: 20
<212> TYPE: DNA
<213> ORGANISM: Artificial
<220> FEATURE:
<223> OTHER INFORMATION: primer

<400> SEQUENCE: 80
ccccagrgat ccaaccrrtc                                               20

<210> SEQ ID NO 81
<211> LENGTH: 25
<212> TYPE: DNA
<213> ORGANISM: Artificial
<220> FEATURE:
<223> OTHER INFORMATION: primer

<400> SEQUENCE: 81
gaggtaccat ggacatgagg gcccc                                         25

<210> SEQ ID NO 82
<211> LENGTH: 36
<212> TYPE: DNA
<213> ORGANISM: Artificial
<220> FEATURE:
<223> OTHER INFORMATION: primer

<400> SEQUENCE: 82
agagcttcaa tagggtgac tgttagctcg agacgc                              36

<210> SEQ ID NO 83
<211> LENGTH: 30
<212> TYPE: DNA
<213> ORGANISM: Artificial
<220> FEATURE:
<223> OTHER INFORMATION: primer

<400> SEQUENCE: 83
caggctagca ccatggagac tgggctgcgc                                    30

<210> SEQ ID NO 84
<211> LENGTH: 31
<212> TYPE: DNA
<213> ORGANISM: Artificial
<220> FEATURE:
<223> OTHER INFORMATION: primer

<400> SEQUENCE: 84
tagacgcgtt catttacccg gagagcggga g                                  31